US010934521B2

(12) United States Patent
Lee et al.

(10) Patent No.: US 10,934,521 B2
(45) Date of Patent: Mar. 2, 2021

(54) GENETICALLY MODIFIED MICROORGANISMS

(71) Applicant: University of Kent, Kent (GB)

(72) Inventors: Matthew John Lee, Kent (GB); Stefanie Frank, Kent (GB); Martin James Warren, Kent (GB)

(73) Assignee: UNIVERSITY OF KENT, Canterbury (GB)

( * ) Notice: Subject to any disclaimer, the term of this patent is extended or adjusted under 35 U.S.C. 154(b) by 0 days.

(21) Appl. No.: 15/773,596

(22) PCT Filed: Nov. 4, 2016

(86) PCT No.: PCT/GB2016/053435
§ 371 (c)(1),
(2) Date: May 4, 2018

(87) PCT Pub. No.: WO2017/077320
PCT Pub. Date: May 11, 2017

(65) Prior Publication Data
US 2019/0144814 A1    May 16, 2019

(30) Foreign Application Priority Data
Nov. 5, 2015  (GB) ........................... 1519554

(51) Int. Cl.
| | | |
|---|---|---|
| *C12N 15/52* | (2006.01) | |
| *C12N 1/20* | (2006.01) | |
| *C07K 14/195* | (2006.01) | |
| *C12N 9/04* | (2006.01) | |
| *C12N 9/12* | (2006.01) | |
| *C12N 9/88* | (2006.01) | |
| *C12N 15/62* | (2006.01) | |
| *C12P 1/04* | (2006.01) | |
| *C12P 7/18* | (2006.01) | |

(52) U.S. Cl.
CPC ............. *C12N 1/20* (2013.01); *C07K 14/195* (2013.01); *C12N 9/0006* (2013.01); *C12N 9/12* (2013.01); *C12N 9/88* (2013.01); *C12N 15/52* (2013.01); *C12N 15/62* (2013.01); *C12P 1/04* (2013.01); *C12P 7/18* (2013.01); *C07K 2319/01* (2013.01); *C12Y 101/01006* (2013.01); *C12Y 101/01077* (2013.01); *C12Y 207/01029* (2013.01); *C12Y 402/03003* (2013.01)

(58) Field of Classification Search
CPC ............... C12P 7/18; C12N 1/20; C12N 9/88
USPC ..................................................... 435/158
See application file for complete search history.

(56) References Cited

U.S. PATENT DOCUMENTS

| | | | | |
|---|---|---|---|---|
| 9,187,766 | B2 * | 11/2015 | Prentice ............... | C07K 14/195 |
| 2012/0210459 | A1 | 8/2012 | Kerfeld | |
| 2013/0133102 | A1 | 5/2013 | Kerfeld | |
| 2014/0328801 | A1 * | 11/2014 | Prentice ............... | C07K 14/195 |
| | | | | 424/93.2 |
| 2015/0026840 | A1 | 1/2015 | Kerfeld | |

FOREIGN PATENT DOCUMENTS

| | | |
|---|---|---|
| EP | 2574620 | 4/2013 |
| GB | 1519554 | 11/2015 |
| WO | WO 2011/094765 | 8/2011 |
| WO | WO 2013/063246 | 5/2013 |
| WO | WO 2017/077320 | 5/2017 |

OTHER PUBLICATIONS

Parsons et al. J. Biol. Chem. 283(21): 14366-143750 (2008). (Year: 2008).*
Combined Search and Examination Report under Sections 17 and 18(3) dated May 10, 2016 for GB Patent Application No. 1519554.8 filed Nov. 5, 2015 (Inventors—Matthew John Lee, et al. // Applicant University of Kent) (8 pages).
Written Opinion dated May 11, 2017 for International Patent Application No. PCT/GB2016/053435 filed Nov. 4, 2015, which published as WO 2017/0773230 on May 11, 2017 (Inventors—Matthew John Lee, et al. // Applicant University of Kent) (10 pages).
International Search Report dated May 11, 2017 for International Patent Application No. PCT/GB2016/053435 filed Nov. 4, 2015, which published as WO 2017/0773230 on May 11, 2017 (Inventors—Matthew John Lee, et al. // Applicant University of Kent) (8 pages).
International Preliminary Report on Patentability dated May 11, 2017 for International Patent Application No. PCT/GB2016/053435 filed Nov. 4, 2015, which published as WO 2017/0773230 on May 11, 2017 (Inventors—Matthew John Lee, et al. // Applicant University of Kent) (11 pages).

(Continued)

*Primary Examiner* — Tekchand Saidha
(74) *Attorney, Agent, or Firm* — Polsinelli PC

(57) ABSTRACT

The present invention relates to genetically modified microorganisms comprising one or more heterologous nucleic acid molecules together encoding at least three different proteins, each protein comprising an enzymatic domain and a bacterial microcompartment-targeting signal polypeptide, wherein said enzymatic domains each catalyse a different substrate to product conversion in the same metabolic pathway, and wherein said microorganisms are essentially free of bacterial microcompartments (BMCs); and to cell free systems comprising aggregates comprising at least three different proteins, each protein comprising an enzymatic domain and a bacterial microcompartment-targeting signal polypeptide, wherein said enzymatic domains each catalyse a different substrate to product conversion in the same metabolic pathway, and wherein said system does not comprise bacterial microcompartments; and to methods for the production of said microorganisms and cell free systems and their use in methods of producing a product of interest.

Figure 1:
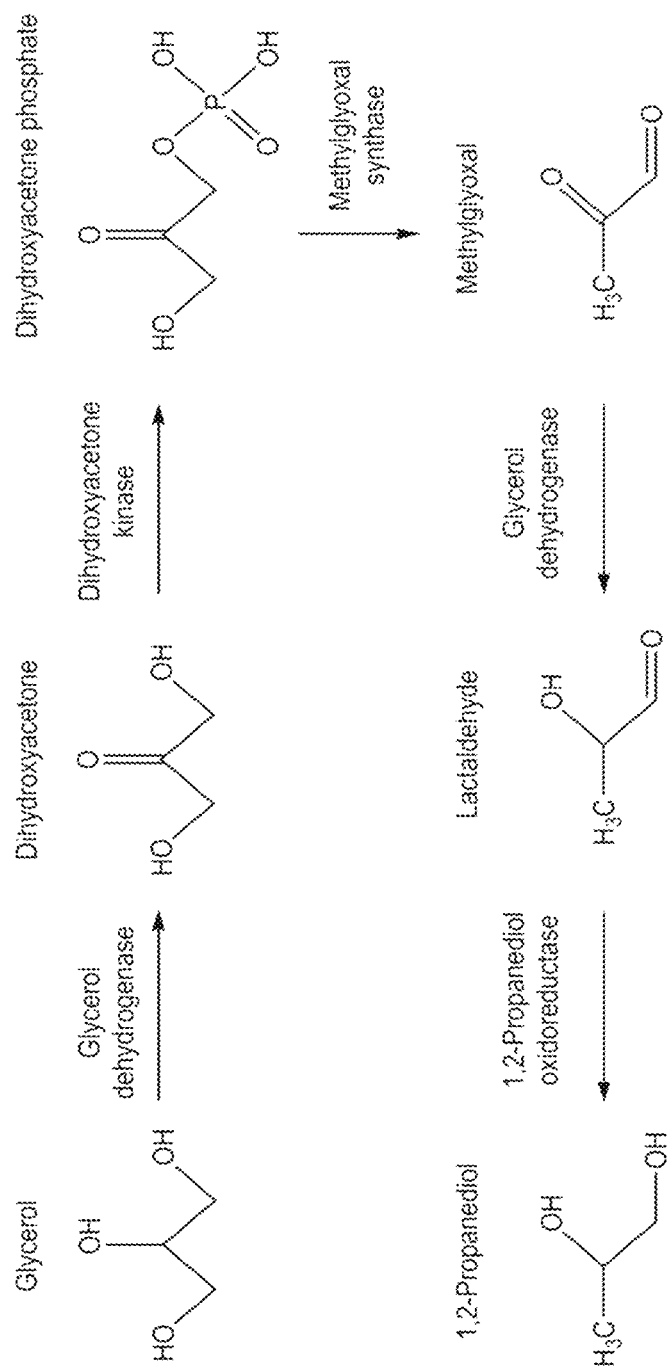

13 Claims, 7 Drawing Sheets
Specification includes a Sequence Listing.

(56) References Cited

OTHER PUBLICATIONS

Aussignargues C, et al. (2015) Bacterial microcompartment assembly: The key role of encapsulation peptides. Commun Integr Biol. 8(3):e1039755.

Axen SD, et al. (02014) A taxonomy of bacterial microcompartment loci constructed by a novel scoring method. PLoS Comput Biol. 10(10):e1003898.

Cheng S, et al. (2011) Genetic analysis of the protein shell of the microcompartments involved in coenzyme B12-dependent 1,2-propanediol degradation by *Salmonella*. J Bacteriol. 193(6):1385-1392.

Chowdhury C, et al. (2014) Diverse bacterial microcompartment organelles. Microbiol Mol Biol Rev. 78(3):438-468.

Fan C, et al. (2010). Short N-terminal sequences package proteins into bacterial microcompartments. Proc Natl Acad Sci USA. 107(16):7509-7514.

Jakobson CM, et al. (2015) Localization of proteins to the 1,2-propanediol utilization microcompartment by non-native signal sequences is mediated by a common hydrophobic motif. J Biol Chem. 290(40):24519-24533.

Jorda J, et al. (2013) Using comparative genomics to uncover new kinds of protein-based metabolic organelles in bacteria. Protein Sci. 22(2):179-195.

Kim EY, et al. (2014) A rapid flow cytometry assay for the relative quantification of protein encapsulation into bacterial microcompartments. Biotechnol J. 9(3):348-354.

Lawrence AD, et al. (2014) Solution structure of a bacterial microcompartment targeting peptide and its application in the construction of an ethanol bioreactor. ACS Synth Biol. 3(7):454-465.

Lee MJ, et al. (2016) Employing bacterial microcompartment technology to engineer a shell-free enzyme-aggregate for enhanced 1,2-propanediol production in *Escherichia coli*. Metab Eng. 36:48-56.

Lee MJ, et al. (2015) Poster titled "Enhancing Metabolic Activity Through the use of BMCs and Protein Scaffolds". Presented at Synthetic Biology Conference (Jun. 28, 2015-Jul. 3, 2015 at Sunday River in Newry, Maine).

Parsons JB, et al. (2008) Biochemical and structural insights into bacterial organelle form and biogenesis. J Biol Chem. 283(21):14366-14375.

Sampson EM, et al. (2008) Microcompartments for B12-dependent 1,2-propanediol degradation provide protection from DNA and cellular damage by a reactive metabolic intermediate. J Bacteriol. 190(8):2966-2971.

Sargent F, et al. (2013) A synthetic system for expression of components of a bacterial microcompartment. Microbiology. 159(Pt 11):2427-2436.

Yeates TO, et al. (2011) The protein shells of bacterial microcompartment organelles. Curr Opin Struct Biol. 21(2):223-231.

Juodeikis R, et al. (2020) Effect of metabolosome encapsulation peptides on enzyme activity, coaggregation, incorporation, and bacterial microcompartment formation. MicrobiologyOpen. 9(5):e1010. doi: 10.1002/mbo3.1010.

\* cited by examiner

GENETICALLY MODIFIED MICROORGANISMS

CROSS-REFERENCE TO RELATED APPLICATIONS

This application is a national phase application of International Application No. PCT/GB2016/053435 filed 4 Nov. 2016, which claims priority to GB Application No. 1519554.8 filed 5 Nov. 2015, each of which is incorporated in its entirety by reference herein.

REFERENCE TO SEQUENCE LISTING

The Sequence Listing submitted 4 May 2018 as a text file named "10981_9_SEQ LISTING.txt", created on 3 May 2018 and having a size of 44740 bytes, is hereby incorporated by reference pursuant to 37 C.F.R. § 1.52(e)(5).

The present invention relates to genetically modified microorganisms and their use in the production of desired products of metabolic pathways, and particularly in improving the levels of production of said products. In particular the microorganisms of the present invention are modified to comprise enzymes of a metabolic pathway for a product of interest, wherein the enzymes are each tagged with a bacterial microcompartment (BMC)-targeting signal peptide, and wherein the microorganism lacks bacterial microcompartments. The present invention also relates to cell-free systems comprising said (BMC)-targeting signal peptide tagged enzymes in the absence of BMCs.

BACKGROUND

Bacterial microcompartments (BMCs) are metabolosomes, i.e. discrete protein-based organelles in which steps of a particular metabolic pathway occur. BMCs are typically 40 to 200 nm in diameter and consist of a semipermeable proteinaceous outer layer that encases the enzymes that catalyse steps of a particular metabolic process. Thus, within a BMC, enzymatic activity of a particular metabolic pathway or part thereof is concentrated. The encapsulated environment is ideal for the channeling of toxic/volatile intermediates.

BMCs are thought to be involved in eight or more metabolic processes. BMCs are widely distributed (in approximately 17% of bacteria in 23 different phyla). Multiple BMC types can be found in a single genome. A particular BMC type is associated with a particular metabolic process. These include anabolic processes such as carbon dioxide fixation (in the carboxysome) and catabolic processes such as 1,2-propanediol utilisation (in the Pdu BMC) and ethanolamine utilisation (in the Eut BMC) and choline degradation (in the Cut BMC).

The first characterized BMC was the carboxysome, which is found in cyanobacteria and some chemoautotrophs. In the carboxysome, the enzymes carbonic anhydrase and RuBisCo are retained within the confines of the macromolecular complex to provide an environment for enhanced carbon dioxide fixation.

The propanediol utilization (pdu) operon is composed of 23 genes and encodes largely for proteins that form a BMC with a diameter of between 100 and 150 nm. Six of the genes (pduABJKUT) encode for shell proteins that comprise BMC domains as their structural core and form hexameric tiles, which align together to form the facets and edges of the outer casing of the capsule structure. The vertices of the BMCs are thought to be formed from the pentameric PduN.

The Pdu BMC shell proteins encapsulate the enzymes for 1,2-propanediol metabolism, including the diol dehydratase (PduCDE), and the alcohol and aldehyde dehydrogenases (PduP and Q). The metabolosome also houses enzymes for the repair and reactivation of the diol dehydratase (PduG, H) and its coenzyme adenosylcobalamin (PduO, S), The shell of the BMC allows the passage of its substrates, cofactors, and coenzymes into the BMC as well as the exit of the metabolic products. This is likely mediated through the central pores that are formed within the tiles of the shell structure. Other proteins are thought to interact with the shell proteins on the external surface of the structure, including PduV, which may help to localize the BMC within the cell.

Recent studies have also revealed targeting sequences that mediate protein encapsulation within BMCs. Enzymes located within BMCs comprise such BMC-targeting signal sequences. Previous studies have demonstrated that tagging proteins not found naturally within BMCs, e.g. GFP, with a BMC-targeting signal sequence results in the localisation of those proteins within BMCs.

In the field of metabolic engineering, a number of attempts have been made to target metabolic pathways of interest to BMCs. The reasoning for such attempts is that pathway encapsulation within a BMC would permit increased flux through the pathway, control of molecules that enter and exit the BMCs, sequestration of intermediates, concentration of reagents, optimisation of reaction environment, etc.

Through heterologous expression, empty Pdu BMCs have been successfully expressed in cells that lack them in wild-type form. It was found that six proteins PduA, B, B', J, K and N were necessary and sufficient for BMC formation in *E. coli*. The absence of PduU and PduT did not prevent shell formation, even though they are known to be shell proteins. In *Salmonella*, it has been found that PduM is required, but PduA is dispensable.

Other groups have successfully targeted non-native proteins to BMCs. The present inventors have previously demonstrated the usefulness of BMCs and targeting sequences in the formation of functional bioreactors for the production of ethanol.

The BMC-targeting sequence of PduP or PduD was fused to the enzymes of the ethanol production pathway: pyruvate decarboxylase and alcohol dehydrogenase, and the tagged enzymes were co-expressed with BMC shell proteins in a bacterial cell that does not naturally produce BMCs. Co-production of tagged-enzymes for ethanol formation and the BMC shell proteins resulted in significantly more ethanol in comparison to strains with cytoplasmic (untagged) enzymes.

US 2012/0210459 discloses various means for designing and implementing BMCs for customizing metabolism in various organisms. Various sequences comprising BMCs are disclosed and the application teaches the expression of said sequences in organisms that do not naturally comprise BMCs. This document teaches co-expression of said BMCs with enzymes of interest, optionally with a BMC targeting signal peptide linked thereto. US 2013/0133102 discloses a variety of known and predicted BMC-targeting sequences.

SUMMARY

Surprisingly, the present inventors have now found that increased levels of a product of interest can be obtained using microorganisms that comprise polypeptides having enzymatic domains and BMC-targeting signal sequences, wherein the enzymatic domains catalyse steps of the same metabolic pathway for the production of said product of interest, but wherein the cell lacks the ability to produce BMCs.

In one aspect, the present invention provides a genetically modified microorganism comprising one or more heterologous nucleic acid molecules together encoding at least three different proteins, each protein comprising an enzymatic domain and a bacterial microcompartment-targeting signal polypeptide, wherein said enzymatic domains each catalyse a different substrate to product conversion in the same metabolic pathway, and wherein said microorganism is essentially free of bacterial microcompartments.

Alternatively viewed, the present invention provides a genetically modified microorganism comprising at least three different recombinant proteins, each protein comprising an enzymatic domain and a bacterial microcompartment-targeting signal polypeptide, wherein said enzymatic domains each catalyse a different substrate to product conversion in the same metabolic pathway, and wherein said microorganism is essentially free of bacterial microcompartments.

Without wishing to be bound by theory, the inventors believe that the BMC-targeting signal polypeptides mediate aggregation of said proteins. The result of the proteins of the invention each comprising an enzymatic domain and a BMC-targeting signal polypeptide is the aggregation of proteins comprising said enzymatic domains. Although aggregation is typically an undesirable occurrence in protein expression systems, the inventors have determined that in the context of multi-step metabolic pathways, it is surprisingly advantageous. As a result of the aggregation, enzymatic activity is spatially concentrated and there can be rapid channeling of the product of one enzymatically catalysed metabolic step to the active site of a second enzymatic domain that catalyses a subsequent step in which said product is a necessary substrate.

The present inventors have determined that the advantages of performing a multi-step metabolic pathway in a BMC (concentration of enzymatic activity and reaction substrates) can in fact be achieved in the absence of a BMC. Furthermore, the present inventors have demonstrated that in cells expressing multiple recombinant proteins comprising an enzymatic domain and a BMC targeting signal polypeptide, increased product yield is achieved in cells lacking BMCs as compared to those comprising BMCs. This finding was very surprising, and counterintuitive, given that the consensus in the field prior to the present invention was that product yields would be increased by linking enzymes to BMC-targeting sequences with the specific purpose of recruiting said enzymes into co-expressed BMCs.

Furthermore, as shown in the present Examples, the addition of BMC-targeting sequences to most enzymes reduces the specific activity of the enzymes. In addition, aggregation is usually considered to have a detrimental effect on protein function, and is therefore considered undesirable. Therefore, the present inventors' finding that despite decreased enzyme activity as a result of fusing BMC-targeting signal polypeptides to said enzymes, and despite the absence of the BMCs, an increase in product yield is observed in the microorganisms of the invention, was very surprising.

The present invention is particularly advantageous in multi-step pathways, since a greater number of steps requires a greater number of enzymatic domains and a greater number of interactions between the product(s) of one step and the active site of a subsequent enzymatic domain. In such systems requiring numerous complex interactions, the spatial concentration of enzymatic domains and reaction substrates is particularly advantageous.

Preferably, the microorganism of the invention comprises at least four, five, six, seven, eight or nine of said different recombinant proteins. Alternatively viewed, preferably, the microorganism of the invention comprises one or more heterologous nucleic acid molecules together encoding at least four, five, six, seven, eight or nine of said different proteins. Throughout this application, disclosures relating to one or more polypeptides or proteins are to be considered as disclosures relating to one or more nucleic acid molecules encoding said polypeptides or proteins, and vice versa.

The enzymatic domains as referred to herein each catalyse a different substrate to product conversion in the same metabolic pathway. A "metabolic pathway" is a series of substrate to product conversions, each of which is catalysed by an enzyme, wherein the product of one enzyme acts as the substrate for the next enzyme. The enzymatic domains as referred to herein each catalyse a different substrate to product conversion in the same metabolic pathway for the production of a product of interest.

The microorganisms of the invention, also termed herein "microbes", "microbial host cells" or simply "host cells" or "cells", may be any microorganism in which recombinant proteins can be expressed. By "microorganism" is meant any unicellular prokaryotic or eukaryotic organism. Preferred microorganisms are bacteria, cyanobacteria, microalgae, filamentous fungi and yeasts. Most preferably, the microorganism is a bacterium.

As explained in more detail below, the invention provides methods of producing a product of interest comprising growing the microorganism of the invention in a culture medium and under conditions wherein the product is produced and optionally recovering the product. Depending on the product of interest, the product may be secreted by the microorganism and recovered from the culture medium, or the product may be sequestered by the microorganism, necessitating extraction therefrom. In either case, to maximise production of the product of interest, the microorganisms are preferably tolerant to the product of interest.

In some embodiments, the microorganisms have the ability to utilize carbohydrates. Optionally, the microorganisms of the invention are photosynthetic, preferably photosynthetic bacteria.

The microorganisms of the present invention comprise at least three recombinant proteins and in some embodiments the microorganisms are further genetically modified to remove the ability of the cell to form BMCs. The ability to genetically modify the microorganism is essential for the production of any recombinant microorganism. Thus, preferably the microorganisms are competent. "Competence" is the ability of a cell to take up extracellular nucleic acid molecules from its environment. The competence may be naturally occurring or induced, i.e. artificial competence, in which the microorganisms in culture are treated to make them transiently permeable to DNA.

Preferably, the microorganisms of the present invention have the ability to grow to high cell densities. It will be within the competencies of the person of ordinary skill in the art to determine the optimal cell density for a particular microorganism and pathway of interest. Preferably, the microorganisms are thermophilic. Preferably, the microorganisms are able to grow under anaerobic conditions. Alternatively preferably, the microorganisms are able to grow under aerobic conditions.

The above characteristics of the microorganism of the invention can be conferred by mutagenesis and selection, genetic engineering, or can be natural.

Preferably, the microorganism is selected from the group consisting of *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula*, or *Saccharomyces*.

Preferably, the microorganism is a bacterium, more preferably of the genus *Escherichia*, most preferably *E. coli*. *E. coli* is well established as an industrial microorganism used in the production of a variety of products (chemical compounds, amino acids, vitamins, recombinant proteins). The entire *E. coli* genome has also been sequenced, and the genetic systems are highly developed.

The preferred yeast organism is *Saccharomyces cerevisiae*. This organism has a long history of use in industrial processes and can be manipulated by both classical microbiological and genetic engineering techniques. It is well-characterized genetically; the entire genome of *S. cerevisiae* has been sequenced. The organism grows to high cell densities.

Preferred microalgae for use in the present invention include *Chlorella* and *Prototheca*.

As mentioned above, the microorganism of the invention is essentially free of BMCs, i.e. expresses essentially no BMCs. Preferably, the microorganism of the invention is free of BMCs, i.e. does not express BMCs. Preferably, the microorganism of the invention does not naturally express BMCs, i.e. does not naturally comprise the genes necessary for the expression of BMCs. By "naturally" in this context is meant "natively", i.e. prior to any modification according to the invention. In such microorganisms, no genetic modification is required to prevent the microorganism from expressing BMCs. Throughout the application, the terms "express" and "expresses" are interchangeable with the term "having the ability to express", i.e. comprising the genes necessary for expression.

Alternatively, preferably, the microorganism of the invention naturally expresses BMCs but has been modified to reduce essentially all, preferably all, of the ability to express BMCs. In other words, the microorganism of the invention is preferably of a species or strain that natively expresses BMCs but has been modified to reduce essentially all, preferably all, of the cell's ability to express BMCs. Suitable modifications to achieve this reduction are discussed in more detail elsewhere herein.

In nature, microorganisms that naturally express BMCs typically do so only under certain conditions, namely in the presence of inducer molecules, which for any given BMC is the substrate for the pathway that comprises steps catalysed by enzymes located within the BMCs. For instance, Pdu BMCs are only expressed by microorganisms comprising the necessary genes when said microorganisms are exposed to 1,2-propanediol. Similarly, Eut BMCs are only expressed by microorganisms comprising the necessary genes when said microorganisms are exposed to ethanolamine.

Thus, in an alternative embodiment, the microorganism of the invention is of a species or strain that naturally expresses BMCs, i.e. that comprises the genes necessary for the expression of BMCs, and wherein expression of said BMCs is inducible by the presence of one or more inducer molecules, but wherein said microorganism is in an environment, e.g. a culture medium, that does not permit expression of BMCs. In other words, preferably the genetically modified microorganism of the invention is present in a culture medium in which the level of said inducer molecule(s) is too low to induce the expression of said BMCs. Preferably the culture medium lacks said inducer molecule(s).

If the microorganism naturally expresses Pdu BMCs, then said molecule is 1,2-propanediol. If the microorganism expresses Eut BMCs, then said molecule is ethanolamine. Expression of other BMCs is known to be induced by the presence of choline, fucose or rhamnose.

Thus, the present invention provides a microorganism of the invention present in a culture medium in which the level of said inducer molecule(s) is too low to induce the expression of said BMCs. Preferably the culture medium lacks said inducer molecule(s). Alternatively viewed, the present invention provides a culture medium comprising a microorganism of the invention that naturally expresses BMCs, i.e. that comprises the genes necessary for the expression of BMCs, wherein in said culture medium the level of said inducer molecule(s) is too low to induce the expression of said BMCs. Preferably the culture medium lacks said inducer molecule(s). Preferably, the culture media lacks one or more, preferably all of propanediol, ethanolamine, choline, fucose and rhamnose.

Microorganisms that possess the ability to produce BMCs, i.e. naturally express, i.e. natively express one or more of Pdu, Eut and carboxysome BMCs, or less common BMCs, are known in the art, for instance from Axen et al., (2014) *PLOS Computational Biology* 10(10):e1003898, US 2012/0210459, and Jorda J, et al., (2013) *Protein Science: A Publication of the Protein Society.* 22(2):179-195. Dataset S1 of Axen et al. comprehensively lists bacterial strains that possess the ability to produce BMCs, i.e. naturally comprise the genes necessary for production of BMCs. The skilled person would be able to determine whether or not a particular microorganism possesses the ability to produce BMCs, i.e. comprises the genes necessary for the expression of BMCs.

The microorganisms of the present invention are genetically modified to increase the yield of the product of interest. As used herein, the term "wild type microorganism" or "wild type cell" encompasses the typical, i.e. most prevalent microorganism of a species or strain as it occurs in nature. Existing strains of a particular species are not necessarily "wild type" strains, however, existing strains lack the modifications of the invention described herein. The term "wild type" is used herein as shorthand to refer to microorganisms of the same strain as the microorganism of the invention but lacking the genetic modifications of the invention as described herein, even though such microorganisms may not be the most prevalent strain. This is how the term is typically used in the field.

The microorganisms of the invention are recombinant microorganisms, i.e. they comprise one or more recombinant nucleic acid molecules. Cells and/or microorganisms may be genetically modified by genetic engineering techniques (e.g., recombinant technology), classical microbiological techniques, or a combination of such techniques. Such techniques are generally disclosed, for example, in Sambrook et al., 1989, *Molecular Cloning: A Laboratory Manual*, Cold Spring Harbor Labs Press.

The genetically modified microorganisms of the invention can include a microorganism in which nucleic acid molecules have been inserted, deleted or modified (i.e., mutated; e.g., by insertion, deletion, substitution, and/or inversion of nucleotides), in such a manner that such modifications provide the desired effect of increased yields of the product of interest within the microorganism or in the culture medium.

As used herein, genetic modifications which result in a decrease in gene expression, in the function of the gene, or in the function of the gene product (i.e. the protein encoded by the gene) can be referred to as inactivation (complete or partial), deletion, interruption, blockage or down-regulation of a gene. They can be referred to as null mutations or loss of function mutations. For example, a genetic modification in a gene which results in a decrease in the function of the protein encoded by such gene, can be the result of a complete deletion of the gene (i.e., the gene does not exist, and therefore the protein is not produced), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity). Genetic modifications which result in an increase in gene expression or function can be referred to as amplification, overproduction, overexpression, activation, enhancement, addition, or up-regulation of a gene. The terms "gene expression" and "protein expression" are used interchangeably herein. Methods and types of mutation are well-known in the art and any suitable method or type can be present in the microorganisms of the present invention. Mutations include, for instance, missense mutations, nonsense mutations, insertions, deletions, duplications, frameshift mutations and repeat expansions, and any combination thereof.

Addition of recombinant genes to increase gene expression can include maintaining the recombinant gene(s) on replicating plasmids or integrating the recombinant gene(s) into the genome of the production organism. Furthermore, increasing the expression of desired recombinant genes can include operatively linking the recombinant gene(s) to native or heterologous transcriptional control elements.

The microorganisms of the invention comprise one or more heterologous nucleic acid molecules together encoding at least three different proteins (that are by definition recombinant proteins). Alternatively viewed, the microorganisms of the present invention comprise at least three different recombinant proteins. Preferably, each of said proteins is encoded by a different recombinant nucleic acid molecule. Alternatively viewed, preferably each of said heterologous nucleic acid molecules encodes only one of said proteins. Alternatively, two, three, or more of said proteins are encoded by the same recombinant nucleic acid molecule. Preferably, the microorganism of the invention comprises 3, 4, 5, 6, 7, 8 or 9 recombinant proteins as defined herein.

As used herein, the term "protein" means a polymer of amino acid residues. The terms "polypeptide" and "protein" are used interchangeably herein. The recombinant proteins of the invention each comprise a region having enzymatic activity and a BMC-targeting signal polypeptide. A mere oligopeptide comprising 2 (a dipeptide), 3 (a tripeptide) or up to about 25 amino acids is not sufficiently long to comprise a region with enzymatic activity and a BMC-targeting sequence. The proteins of the invention are preferably each a polypeptide comprising at least 75 amino acids, more preferably at least 100 amino acids, still more preferably at least 120 amino acids.

Both full length proteins and fragments thereof are contemplated by the term "protein" as used herein. "Fragments" in the context of the present invention are functional fragments, i.e. a fragment comprises the same enzymatic activity as the full length protein of which it is a fragment. The term "protein" also includes post-expression modifications to the protein, including, but not limited to, glycosylation, acetylation and phosphorylation. The term "protein" also applies to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or mixture of L- and D-amino acids.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, polypeptide-nucleic acids (PNAs). Unless otherwise indicated, a particular nucleic acid sequence also encompasses "conservatively modified variants" thereof (e.g., degenerate codon substitutions) and complementary sequences, as well as the sequence explicitly indicated.

As used herein, the term "heterologous" when applied to a nucleic acid molecule or protein means a nucleic acid molecule or protein that is not naturally, i.e. natively, present or encoded in the genome of that strain of microorganism. Thus, heterologous nucleic acid molecules are those that are introduced into the microorganism by recombinant techniques. The terms "non-native" and "heterologous" are used interchangeably. In the context of the present invention, the terms "heterologous" and "recombinant" are used interchangeably. As used herein, the term "native" when applied to a nucleic acid molecule or protein means a nucleic acid molecule or protein that is present or encoded in the genome of that strain of microorganism.

The microorganism of the present invention comprises one or more heterologous nucleic acid molecules that encode at least three proteins, each protein comprising an enzymatic domain and a bacterial microcompartment-targeting signal polypeptide. In such a heterologous nucleic acid molecule, the coding sequence for the enzymatic domain may be native to the microorganism and the coding sequence for the BMC-targeting signal polypeptide may be non-native, or vice versa. Alternatively, both the coding sequence for the enzymatic domain and the coding sequence for the BMC-targeting signal polypeptide may be non-native to the microorganism, and may be from the same or different non-native sources. Alternatively, the coding sequence for the enzymatic domain and the coding sequence for the BMC-targeting signal polypeptide may both be native to the microorganism but the nucleic acid molecule comprises one or more additional sequences that are non-native to the microorganism. These additional sequences may encode for other sequences within the encoded protein such as linker sequences between the enzymatic domain and the BMC-targeting signal polypeptide, or they may be regulatory sequences such as promoters. Alternatively, the coding sequence for the enzymatic domain and the coding sequence for the BMC-targeting signal polypeptide may be native to the microorganism but are not found natively in the same nucleic acid molecule, such that overall the nucleic acid molecule of the invention is heterologous to the microorganism of the invention.

The heterologous nucleic acid molecules of the present invention are recombinant nucleic acid molecules. Recombinant nucleic acid molecules, also known as "chimeric nucleic acid molecules" are nucleic acid molecules formed by laboratory methods of genetic recombination (such as molecular cloning) to combine nucleic acid sequences from two or more sources.

A "recombinant protein" is a protein that is encoded by a recombinant nucleic acid molecule, preferably by recombinant DNA (also termed "chimeric DNA"). A recombinant protein is encoded by a recombinant gene, i.e. by a chimeric gene, specifically by the coding region(s) of the chimeric gene. Thus, the recombinant nucleic acid molecules of the present invention comprise at least three different chimeric genes encoding the at least three different proteins defined herein. Recombinant protein expression is the expression of proteins within a cell from recombinant DNA. The at least three different proteins that the microorganisms of the invention comprise are recombinant proteins, and the terms "protein" and "recombinant protein" are used interchangeably in this context throughout the application.

"Chimeric gene" refers to any gene that is not a native gene. A chimeric gene as used herein comprises regulatory and coding sequences that are not found together in nature and/or a coding sequence comprising two or more sequence regions not found together in nature. Accordingly, a chimeric gene may comprise regulatory sequences and coding sequences that are derived from different sources, or regulatory sequences and coding sequences derived from the same source, but arranged in a manner different than that found in nature. A "foreign gene", "non-native" or "heterologous gene" refers to a gene not normally found in the host organism, but that is introduced into the host organism by gene transfer. Foreign genes can comprise genes native to one organism inserted into a different, i.e. non-native, organism, or they can comprise chimeric genes. A "transgene" is a gene that has been introduced into the genome by a transformation procedure.

As explained in more detail below, the enzymatic domain (also termed "the region with enzymatic activity" herein) and the BMC-targeting signal polypeptide of a recombinant protein of the invention preferably originate from different sources, i.e. from different organisms or from different proteins within a single organism. In these embodiments, the coding sequence within the recombinant nucleic acid molecule is a chimeric sequence.

In other embodiments, the enzymatic domain and the BMC-targeting signal polypeptide of a recombinant protein of the invention originate from the same source, preferably from a microorganism that naturally expresses a protein comprising said enzymatic domain and said BMC-targeting signal polypeptide. Optionally, this microorganism is a wild type organism of the same species as the microorganism of the invention, however, typically this is not the case. In these embodiments, the coding sequence within the recombinant nucleic acid molecule is not a chimeric sequence, however, the recombinant nucleic acid molecule as a whole is a chimeric sequence due to the coding sequence being operably linked to one or more regulatory sequences, wherein the coding sequence and the one or more regulatory sequences are from different sources. If two or more regulatory sequences are present, they are preferably from different sources from each other. Preferably, the regulatory sequence(s) is/are non-native to the microorganism of the invention.

As used herein, the term "gene" refers to a nucleic acid that is capable of being expressed as a specific polypeptide, optionally including regulatory sequences preceding (5' non-coding sequences) and following (3' non-coding sequences) the coding sequence. "Native gene" or "wild type gene" refers to a gene as found in nature with its own regulatory sequences. "Endogenous gene" refers to a native gene in its natural location in the genome of an organism.

As used herein, the term "coding sequence" refers to a nucleic acid sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a nucleic acid sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. The terms "gene expression" and "protein expression" are used interchangeably herein.

The microorganism of the invention is prepared by the transformation of a microorganism with the one or more heterologous nucleic acid molecules together encoding at least three different proteins, each protein comprising an enzymatic domain and a bacterial microcompartment-targeting signal polypeptide, wherein said enzymatic domains each catalyse a different substrate to product conversion in the same metabolic pathway.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The one or more heterologous nucleic acid molecules of the invention that encode the at least three different proteins are each preferably comprised within a plasmid, vector or cassette. The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter. The one or more heterologous nucleic acids of the invention are typically present in an expression vector, preferably a vector comprising a strong promoter.

Preferably, the at least three recombinant proteins are each over-expressed in the microorganism of the invention. As referred to herein, "over-expressed" means that expression of the gene encoding the protein is increased as compared to, i.e. relative to, the level of expression in a control microorganism, i.e. in a microorganism in the same strain which lacks said one or more heterologous nucleic acid molecules. The skilled person would appreciate that the comparison must be made between the level of expression of a protein in the microorganism of the invention and the level of expression of the same protein (i.e. a protein having the same amino acid sequence) occurring in the control microorganism.

A "control microorganism" is a microorganism of the same strain as the microorganism of the invention which has not been modified according to the invention. In this context of over-expression, a "control organism" has not been modified to over-express the gene in question. A control organism for instance may have been transformed with an "empty" vector or a vector with a control sequence. Preferably, the control microorganism is one that does not comprise the one or more heterologous nucleic acid molecules of the invention that encode a protein comprising an enzymatic domain and a bacterial microcompartment-targeting signal polypeptide. The skilled person will readily be able to determine the appropriate control with which to make the comparison of expression levels.

Gene expression is to be considered in terms of the amount of protein product produced, which may be determined by any convenient method known in the art. The terms "gene expression" and "protein expression" are used interchangeably herein. Methods for the direct and indirect determination of protein expression levels are well-known in the art and any such technique could be used by the skilled person in this regard. For example, expression can be determined by measuring protein activity. Alternatively, the amount of protein produced can be measured to determine the level of expression, for example by Western Blotting or other antibody detection systems, or indeed by any method of assessing or quantifying protein. The assay may be an in vivo or in vitro assay.

In some embodiments, the microorganism of the invention comprises a recombinant protein that is not also expressed by the control microorganism, in which case the level of expression of said protein in the control microorganism is zero. This is the situation, for instance, when the control microorganism is the same strain as the microorganism of the invention and wherein said strain does not naturally express said protein. In other embodiments, the microorganism of the invention comprises a recombinant protein that is also expressed by the control microorganism, in which case the level of expression of the protein in the microorganism of the invention nevertheless exceeds that in the control microorganism.

Thus, the microorganisms of the present invention preferably comprise at least three different recombinant proteins that are each over-expressed relative to the expression level of said protein in a control microorganism as defined above.

Preferably, the one or more heterologous nucleic acid molecules of the present invention together comprise at least three different chimeric genes, each comprising a coding sequence that encodes a different protein comprising an enzymatic domain and a BMC-targeting signal polypeptide as defined anywhere herein operably linked to one or more regulatory elements for the over-expression of said protein. Preferably, said regulatory element is a promoter, more preferably a strong promoter. Thus, preferably each of the heterologous nucleic acid molecules comprises a region encoding one or more of said proteins operably linked to a strong promoter.

Alternatively viewed, the present invention provides a genetically modified microorganism comprising one or more heterologous nucleic acid molecules together encoding at least three different proteins, each protein comprising an enzymatic domain and a bacterial microcompartment-targeting signal polypeptide, wherein said enzymatic domains each catalyse a different substrate to product conversion in the same metabolic pathway, wherein each of said proteins is over-expressed, and wherein said microorganism is essentially free of bacterial microcompartments.

Alternatively viewed, the present invention provides a genetically modified microorganism comprising at least three different proteins, each protein comprising an enzymatic domain and a bacterial microcompartment-targeting signal polypeptide, wherein said enzymatic domains each catalyse a different substrate to product conversion in the same metabolic pathway, wherein each of said proteins is over-expressed and wherein said microorganism is essentially free of bacterial microcompartments.

Preferably, "over-expressed" or "over-expression" means that the level of expression is at least 10%, preferably at least 20%, even more preferably at least 50%, yet more preferably at least 75%, still more preferably at least 90%, and most preferably at least 100% greater in the microorganism of the invention as compared to the level of expression in the control microorganism as defined above. Alternatively, expression may be 2-, 3- or 4-fold or more higher in the microorganism of the invention as compared to the level in the control microorganism defined above.

Over-expression of a protein of interest can be achieved by any technique known in the art, and such techniques would be well known to one of ordinary skill in the art. According to the present invention "overexpressing" may mean simply that an additional gene is expressed in the microorganism beyond the native gene endogenously present in that microorganism but is not limited to such a mechanism. It may include expressing a gene in a microorganism which does not naturally contain such a gene.

Preferably, the microorganism of the invention comprises aggregates comprising said at least three different proteins.

Over-expression is preferably achieved by introducing into the microorganism a recombinant nucleic acid molecule encoding the protein, for example expressed from a stronger or unregulated promoter relative to the gene in the control microorganism, and/or by introducing multiple copies of a protein-encoding nucleic acid molecule.

Preferably, the introduced nucleic acid molecule is modified as compared to a naturally occurring gene encoding the same protein to render it relieved of transcriptional repression, e.g. by mutating or deleting recognition elements for transcriptional repressors or by using expression control elements (e.g. promoters) which are not subject to transcriptional regulation by the transcriptional regulator(s) which normally control expression of the gene. The endogenous gene may alternatively or additionally be modified in this way, or by addition of a stronger promoter. Thus, mutagenesis (including both random and targeted) may for example be used to mutate the endogenous control or regulatory elements so as to increase expression of the endogenous gene (e.g. increase transcription and/or translation). Alternatively, the organism may be engineered to introduce additional or alternative regulatory elements.

In a particular embodiment, a gene may be expressed from a non-native or heterologous promoter (that is a promoter which is heterologous to the encoding gene, i.e. is not the native gene promoter) and particularly a strong, non-native or heterologous promoter. Thus, in this embodiment the gene is not used with its native promoter. A gene may be introduced which is under the control of a non-native promoter. As referred to herein, a strong promoter is one which expresses a gene at a high level, or at least at a higher level than effected by its native promoter. The term "strong promoter" is a term well known and widely used in the art and many strong promoters are known in the art, or can be identified by routine experimentation. The use of a non-native promoter may advantageously have the effect of relieving the gene of transcriptional repression, as at least some of any repressive elements will be located in the native promoter region. By replacing the native promoter with a non-native promoter devoid of repressive elements responsive to the effects of pathway products, the gene will be at least partly relieved of transcriptional repression.

Suitable promoters and expression vectors comprising such promoters for achieving over-expression of a protein of interest are well-known in the art, and the one or more nucleic acid molecules of the invention may comprise any such promoter or may be comprised within any such expression vector to achieve over-expression of the at least three proteins of the invention. Examples include the *E. coli* expression vector pGEX in which protein expression is under the control of the tac promoter, and the pET series of vectors which uses a T7 promoter.

As used herein, the term "enzymatic domain" means the region of the protein that performs and is necessary for the catalysis of a substrate to product conversion. The terms "region having enzymatic activity" and "enzymatic domain" are used interchangeably herein. The enzymatic domain may be a complete enzyme or a function fragment thereof, i.e. a fragment that catalyses the same substrate to product conversion as the complete enzyme. The enzymatic domain comprises a catalytic domain, i.e. an active site, and any other amino acids necessary for the domain to have a conformation that permits said active site to be functional, i.e. to perform catalysis in the presence of the relevant substrates.

In one or more of the recombinant proteins of the invention, the BMC-targeting signal polypeptide may be fully comprised within or may be partially comprised within, i.e. may overlap with, the enzymatic domain. Alternatively viewed, the enzymatic domain may comprise all or part of the BMC-targeting signal polypeptide. In such embodiments, the presence of part or all of the BMC-targeting signal polypeptide is necessary for the function of the enzymatic domain. In such embodiments, the sequences of the BMC-targeting signal polypeptide and the enzymatic domain overlap, at least partially.

Preferably, however, the enzymatic domain and the BMC-targeting signal polypeptide are distinct domains. By distinct in this context is meant that the sequences of the BMC-targeting signal polypeptide and the enzymatic domain do not overlap, i.e. the domains are structurally distinct, i.e. have distinct amino acid sequences. In such embodiments, the BMC-targeting signal polypeptide is not comprised fully or partially within the enzymatic domain, i.e. the enzymatic domain does not comprise all or part of the BMC-targeting signal polypeptide. In these embodiments, the sequence of the enzymatic domain and the BMC-targeting signal polypeptide may be directly adjacent, i.e. the C-terminal amino acid of the BMC-targeting signal polypeptide may be adjacent in sequence to the N-terminal amino acid of the enzymatic domain, or the C-terminal amino acid of the enzymatic domain may be adjacent in sequence to the N-terminal amino acid of the BMC-targeting signal polypeptide.

Optionally, the enzymatic domain and the BMC-targeting signal polypeptide are linked by an amino acid linker. The amino acid linker may comprise any number of amino acids. Preferably, the amino acid linker is 1 to 60 amino acids in length, more preferably 2 to 40 amino acids in length, most preferably 4 to 30 amino acids in length. The amino acid linker sequence may itself be a protein or polypeptide with stable secondary structure, i.e. a rigid linker, such as an alpha helical or beta sheet structure, and optionally with tertiary structure. Preferably, however, the amino acid linker sequence lacks stable secondary structure. Instead, it is preferably a random coil. A random coil is a sequence of amino acids with a conformation in which the amino acids are oriented randomly while still being bonded to adjacent amino acids.

Optionally, the linker comprises one or more sequences that assist with protein purification. In this regard, preferably, the amino acid linker comprises a sequence of 2 to 15, more preferably 2 to 12 or 3 to 12, still more preferably 2 to 6 or 3 to 6 consecutive histidine residues. Optionally, the linker comprises one or more cleavage sites.

Preferably, the BMC-targeting signal polypeptide is N-terminal to the enzymatic domain, optionally separated by a linker sequence as described above.

Preferably, the BMC-targeting signal peptide is located at the N-terminus of the protein. However, it is possible for the protein to comprise amino acids N-terminal to the BMC-targeting signal peptide.

Alternatively preferably, the BMC-targeting signal polypeptide is C-terminal to the enzymatic domain, optionally separated by a linker sequence as described above.

Preferably, the BMC-targeting signal peptide is located at the C-terminus of the protein. However, it is possible for the protein to comprise amino acids C-terminal to the BMC-targeting signal peptide.

As used herein, the term "distinct" also requires the domains to be functionally distinct. "Functionally distinct" as used herein means that the function of one of the domains does not require the presence of the other domain. In the context of the present invention, the two domains are the enzymatic domain and the BMC-targeting signal polypeptide. Thus, in these embodiments, the presence of the BMC-targeting signal polypeptide is not necessary for the function of the enzymatic domain, and vice versa. In such embodiments, cleavage of the BMC-targeting signal polypeptide does not remove the catalytic ability of the enzymatic domain. If the BMC-targeting signal polypeptide was necessary for the catalytic function of the enzymatic domain, then the domains would not be considered "distinct" as the term is used herein, since the enzymatic domain is the region of the protein that performs and is necessary for the catalysis of a substrate to product conversion and so would include the BMC-targeting signal polypeptide.

Preferably one or more, more preferably all, of the recombinant proteins of the invention are "bipartite proteins". A bipartite protein is a protein with at least two functionally distinct domains. A bipartite protein of the present invention may comprise more than two functionally distinct domains but as a minimum it must contain an enzymatic domain and a BMC-targeting signal polypeptide that are functionally distinct.

Optionally, one or more of the recombinant proteins is "native" to the microorganism of the invention. By "native" is meant that the microorganism of the invention is of a strain that naturally expresses a protein with the same amino acid sequence. A recombinant protein is by definition not endogenously expressed by a microorganism because it is expressed from a recombinant nucleic acid molecule, however, the amino acid sequence of a recombinant protein may be identical to a protein expressed endogenously by the microorganism, in which case the recombinant protein is said to be native to the microorganism.

One or more of the recombinant proteins may comprise an enzymatic domain that is native and a BMC-targeting signal polypeptide that is non-native to the microorganism of the invention. Alternatively, one or more of the recombinant proteins may comprise a BMC-targeting signal polypeptide that is native and an enzymatic domain that is non-native to the microorganism of the invention. In these embodiments, the non-native components of the one or more recombinant proteins are preferably native to a different species of microorganism, i.e. a microorganism of a species other than the species of the microorganism of the invention. Alternatively, the non-native components are artificial, i.e. have a sequence not found in nature.

Optionally, the enzymatic domain and the BMC-targeting signal polypeptide of a recombinant protein are both native to the microorganism of the invention but are expressed as parts of different native proteins. In this latter embodiment, the recombinant protein is, overall, non-native to the microorganism of the invention because the strain does not naturally express a protein with the same overall sequence.

If present, amino acid linker(s) between the enzymatic domain and the BMC-targeting signal polypeptide may be native or non-native to the microorganism of the invention. Similarly, any other region of the recombinant protein may be native or non-native to the microorganism of the invention.

Preferably, one or more, more preferably all of the recombinant proteins are non-native to the microorganism of the invention. By "non-native" is meant "heterologous", i.e. that the microorganism is of a strain that does not naturally express a protein with the same sequence. The equivalent definition of "non-native" applies in the context of the non-native enzymatic domains, non-native BMC-targeting signal polypeptides and non-native nucleic acid molecules disclosed herein.

Non-native proteins, parts/regions of proteins, polypeptides, domains and nucleic acid molecules as referred to herein may each occur in nature, i.e. within a different organism from that of the invention, or may be artificial, i.e. not found anywhere in nature.

In a preferred embodiment, one or more of the recombinant proteins is non-native to the microorganism of the invention but is native to, i.e. expressed naturally by, another microorganism. Many bipartite proteins that comprise an enzymatic domain and a BMC-targeting signal sequence are known in the art. Examples of such enzymes include the diol dehydratase (PduDE), the propionaldehyde dehydrogenase (PduP), the phosphotransacylase (PduL) and the 1-propanol dehydrogenase (PduQ) of microorganisms naturally expressing Pdu BMCs, the aldehyde dehydrogenase (EutE) and the ethanolamine deaminase (EutC) of microorganisms naturally expressing Eut BMCs, and the gamma-carbonic anhydrase (CcmM) of microorganims naturally expressing carboxysomes.

If the recombinant protein comprises an enzymatic domain and a BMC-targeting polypeptide, both of which are non-native to the microorganism of the invention, then optionally said enzymatic domain and said BMC-targeting domain are expressed within different proteins by a single other microorganism species, or within proteins expressed by two different other microorganism species. Alternatively, one or more of said domains and polypeptides may be artificial.

Optionally, the enzymatic domain and/or the BMC-targeting sequence, any portion of the recombinant protein, or the entire recombinant protein is artificial, i.e. has an amino acid sequence not found in nature.

Preferably, one or more, more preferably all, of the recombinant proteins of the present invention are fusion proteins. As used herein, a fusion protein is a single protein having at least two domains that are not present in the same protein in nature. Naturally occurring proteins are thus not "fusion proteins" as the term is used herein. In the preferred fusion proteins of the present invention, the enzymatic domain and the BMC-targeting signal polypeptide are not present in the same protein in nature. Optionally, the enzymatic domain and the BMC-targeting signal polypeptide of a fusion protein of the invention are expressed within different naturally occurring proteins in the same organism, which is optionally the wild type organism of the same species as the microorganism of the invention, but preferably an organism of a different species. Alternatively, the two domains are expressed naturally within different organisms. Fusion proteins are preferred bipartite proteins of the invention. The fusion proteins of the invention may also comprise or consist of artificial sequences.

As used herein, a "fusion protein construct" is a nucleic acid construct that is composed of different genes or portions thereof in operable linkage. The components include a nucleic acid molecule encoding at least an enzymatic domain as defined herein and a nucleic acid molecule encoding at least a BMC targeting signal polypeptide as defined herein.

Thus, typically the microorganisms of the invention comprise at least three different recombinant proteins that are not expressed naturally by that strain of microorganism. In some embodiments, however, one or more of the recombinant proteins is identical in amino acid sequence to a protein expressed naturally by that strain of microorganism.

The disclosure herein relating to proteins and parts thereof applies mutatis mutandis to nucleic acid molecules encoding said proteins and parts thereof.

The microorganisms of the invention comprise at least three different recombinant proteins that each comprise an enzymatic domain, wherein the enzymatic domains each catalyse a different substrate to product conversion in the same metabolic pathway. In the presence of suitable substrates, the microorganism of the invention produces the product of the metabolic pathway.

The product produced by the microorganism of the present invention, i.e. the product of interest, may be any product of a metabolic pathway that comprises at least three enzyme catalysed reactions. Preferably, the metabolic pathway for the product of interest comprises the formation of one or more toxic intermediates, and preferably one or more of the recombinant proteins of the invention catalyses a step in which said toxic intermediate is a substrate or product. Preferred products are organic compounds, preferably alcohols. Preferred alcohols are $C_1$ to $C_{12}$ alcohols, more preferably $C_2$ to $C_6$ alcohols. Preferred alcohols are selected from the group consisting of ethanol, 1-propanol, 2-propanol, 1-butanol, 2-butanol, isobutanol, tert-butanol, 1,2-propanediol, 1,3-propanediol, 1,2-butanediol, 1,3-butanediol, 1,4-butanediol and 2,3-butanediol.

If the product of interest is 1,2-propanediol, then the enzymatic domains each catalyse a different substrate to product conversion selected from:
  i) glycerol to dihydroxyacetone
  ii) dihydroxyacetone to dihydroxyacetone phosphate
  iii) dihydroxyacetone phosphate to methylglyoxal
  iv) methylglyoxal to lactaldehyde
  v) lactaldehyde to 1,2-propanediol Preferably, the microorganism comprises at least three different recombinant proteins comprising enzymatic domains that each catalyse a different substrate to product conversion selected from those listed above. More preferably, the microorganism comprises four recombinant proteins comprising enzymatic domains that each catalyse a different substrate to product conversion selected from those listed above.

Preferably said enzymatic domains are present in the form of complete enzymes. Preferably, the enzyme that catalyses the conversion of glycerol to dihydroxyacetone is of the class EC 1.1.1.6, and is preferably glycerol dehydrogenase. Preferably the enzyme that catalyses the conversion of dihydroxyacetone to dihydroxyacetone phosphate is of the class EC 2.7.1.29, and is preferably dihydroxyacetone kinase. Preferably, the enzyme that catalyses the conversion of dihydroxyacetone phosphate to methylglyoxal is of the class EC 4.2.3.3, and is preferably methylgloxal synthase. Preferably, the enzyme that catalyses the conversion of methylglyoxal to lactaldehyde is of the class EC 1.1.1.6, and is preferably glycerol dehydrogenase. Preferably, the enzyme that catalyses the conversion of lactaldehyde to 1,2-propanediol is of the class EC 1.1.1.77, and is preferably 1,2-propanediol oxidoreductase.

Thus, preferably, the microorganism of the invention comprises at least three different recombinant proteins, each protein comprising a different enzyme and a bacterial microcompartment-targeting signal polypeptide, wherein each of said enzymes is selected from those listed above, and wherein said microorganism is essentially free of bacterial microcompartments. Such organisms produce 1,2-propanediol in the presence of a suitable substrate, such as glycerol. Preferably, the microorganism comprises all four of the above enzymes.

Each of the at least three proteins of the invention comprises a BMC-targeting signal polypeptide. A BMC-targeting signal polypeptide is a polypeptide that, when present within a protein, mediates the encapsulation of said protein within a BMC, if present. Such polypeptides are known in the art and the proteins of the invention can comprise any such polypeptide. Two, three or more of the at least three proteins of the invention may comprise the same BMC-targeting signal polypeptide. Alternatively, each protein may comprise a different BMC-targeting signal polypeptide.

In nature, BMC proteins are typically expressed from the same operon as the proteins, e.g. enzymes, that comprise BMC-targeting polypeptides and that localise within the BMCs. Thus, in nature, BMC-targeting signal polypeptides tend to localise within a particular type of BMC, i.e. are directed to a particular type of BMC. For example, in the Pdu operon, the Pdu BMC capsule proteins are expressed from the same operon as the Pdu enzymes, and the BMC-targeting signal sequences within said Pdu enzymes are localise to, i.e. are directed to, the Pdu BMCs. The terms "BMC-targeting signal polypeptide" and "BMC-targeting signal sequence" are used interchangeable herein.

US 2013/0133102 discloses known BMC-targeting signal polypeptides and the types of BMCs to which they are directed. The BMC-targeting signal polypeptides disclosed in this document may be used as BMC-targeting signal polypeptides according to the present invention and US2013/0133102 is incorporated herein by reference. Optionally, the BMC-targeting signal polypeptide of the present invention is a BMC-targeting polypeptide disclosed as such in US 2013/0133102.

The BMC-targeting signal polypeptides of the invention each preferably comprise a region with alpha-helical conformation. Preferably the BMC-targeting signal polypeptides of the invention each comprise an amphipathic alpha helix. Preferably, the BMC-targeting signal polypeptide is adjacent to an N-terminal and/or a C-terminal region without stable secondary structure, i.e. a random coil. Methods of predicting the secondary structure of a given amino acid sequence are well-known in the art, as are methods of designing a synthetic amino acid sequence with a desired secondary structure.

The term "amphipathic alpha helix" or "amphipathic α-helix" refers to a polypeptide sequence that can adopt a secondary structure that is helical with one surface, i.e., face, being polar and the other surface being a nonpolar face. Typically, the polar face comprises primarily polar and/or charged amino acids and the non-polar face comprises primarily hydrophobic amino acids. Methods of predicting the hydrophobicity of peptide sequences and secondary structure conformations such as alpha helices are well-known in the art, for instance Pepfold and Pepwheel.

As used herein, hydrophobic amino acids are considered primarily to include amino acid residues, such as Ile (I), Leu (L), Val (V), Met (M), Phe (F), Tyr (Y), Ala (A), Trp (W). Polar uncharged amino acids are considered primarily to include amino acids such as Gln (Q), Asn (N), Thr (T), Ser (S), and Cys (C). Charged amino acids are considered primarily to include amino acids such as Asp (D), Glu (E), Arg (R), Lys (K), and His (H). Proline and glycine are considered neutral amino acids and are not assigned to a specific group.

Proline tends to break or kink helices because it cannot donate an amide hydrogen bond (having no amide hydrogen), and because its side chain interferes sterically. Its ring structure also restricts its backbone dihedral angle to the vicinity of −70°, which is less common in α-helices. One of skill understands that although proline may be present at certain positions in the BMC-targeting signal polypeptides described herein, the presence of more than three prolines within the sequence would be expected to disrupt the helical structure. Accordingly, the BMC-targeting signal polypeptides of the invention preferably do not comprise more than three prolines, more preferably do not comprise more than two prolines within the alpha-helix forming sequence thereof.

Preferably, the BMC-targeting signal polypeptides are capable of forming coiled coils in solution. Coiled coils are a well-known structural conformation comprising two or more alpha helices coiled together in a manner akin to the strands of a rope. Preferably, the BMC-targeting signal polypeptides are capable of forming coiled coil dimers in solution. The alpha helices within a coiled coil may be arranged in a parallel or anti-parallel conformation. Preferably, the coiled coil has a left-handed conformation, although it may instead have a right-handed conformation. Method of determining the existence of coiled coil conformations are well-known in the art, for instance CCBuilder v1.0 available at http://coiledcoils.chm.bris.ac.uk/app/cc_builder/.

The BMC-targeting polypeptide may be of any length. Preferably, the BMC-targeting signal polypeptide is 5 to 70 amino acids in length, more preferably 10 to 22 amino acids in length, most preferably 14 to 20 amino acids in length. Preferably, the BMC-targeting polypeptide comprises an alpha-helical region that is at least 7 amino acids in length.

As discussed above, naturally occurring BMC-targeting signal polypeptides are found within proteins, typically enzymes, that localise to BMCs. Typically, they are N-terminal sequences; they may however be C-terminal sequences, and in rare instances they are not N- or C-terminal sequences but rather are located within the interior of the naturally occurring protein sequence.

Preferably, the BMC-targeting signal polypeptide of the present invention comprises the N-terminal 70, more preferably 60, more preferably 50, 40, 30, 25, 20, 19, 18, 17, or 16 amino acids of a naturally occurring protein that comprises an N-terminal BMC-targeting signal polypeptide. Alternatively preferably, the BMC-targeting signal polypeptide of the present invention comprises the C-terminal 70, more preferably 60, more preferably 50, 40, 30, 25, 20, 19, 18, 17, or 16 amino acids of a naturally occurring protein that comprises a C-terminal BMC-targeting signal polypeptide.

Preferred naturally occurring proteins that include BMC-targeting signal polypeptides are PduD and PduP preferably from *Citrobacter freundii*, *Propionibacterium acnes*, *Fusobacterium ulcerans*, *Escherichia coli*, *Pectobacterium wasabiae*, *Listeria monocytogenes*, *Shewanella* sp, *Tolumonas aurensis*, *Yersinia frederiksenii*, *Klebsiella pneumoniae*, *Salmonella typhimurium*, *Salmonella enterica Paratyphi* B str. and *Citrobacter koseri*, more preferably from *Citrobacter freundii*. In all of these proteins, the BMC-targeting signal polypeptide is an N-terminal sequence.

Preferably, the BMC-targeting signal polypeptide of the present invention comprises the N-terminal 70, more preferably 60, more preferably 50, 40, 30, 25, 20, 19, 18, 17, or 16 amino acids of a naturally occurring PduP or PduD protein from an organism that naturally expresses Pdu BMCs, preferably from those microorganisms listed above, more preferably from *Citrobacter freundii*.

Preferably, the BMC-targeting signal polypeptide of the present invention comprises residues 1 to 16, more preferably residues 1 to 18 of PduP from an organism that naturally expresses Pdu BMCs, preferably from those microorganisms listed above, more preferably from *Citrobacter freundii*, or residues 1 to 18 of PduD from an organism that naturally expresses Pdu BMCs, preferably from those microorganisms listed above, more preferably from *Citrobacter freundii*.

Preferably, the BMC-targeting signal polypeptide comprises the following sequence:

$X_1X_2X_3X_4X_5X_6X_7X_8X_9$ wherein:

$X_1$, $X_4$, $X_5$, $X_8$, and $X_9$ are hydrophobic amino acids;

$X_2$, $X_3$ and $X_6$ are each independently polar or charged amino acids; and $X_7$ is any amino acid. (SEQ ID NO: 76)

Preferably, $X_1$, $X_4$, $X_5$, $X_8$, and $X_9$ are each independently hydrophobic amino acids selected from the group consisting of I, L, V, M, F, Y, A and W;

$X_2$, $X_3$ and $X_6$ are each independently polar or charged amino acids selected from the group consisting of Q, N, T, S, C, D, E, R, K and H; and $X_7$ is any amino acid. (SEQ ID NO: 77)

Preferably, $X_1$, $X_4$, $X_5$, $X_8$, and $X_9$ are each independently hydrophobic amino acids selected from the group consisting of I, L, V, M, and A;

$X_2$, $X_3$ and $X_6$ are each independently polar or charged amino acids selected from the group consisting of Q, T, E, R, S, D and K; and $X_7$ is any amino acid. (SEQ ID NO: 78)

Preferably, $X_1$ is a hydrophobic amino acid selected from the group consisting of I, L, V and A;

$X_2$ is a polar or charged amino acid selected from the group consisting of E, R and Q;

$X_3$ is a polar or charged amino acid selected from the group consisting of T, Q, E, S, D and K;

$X_4$ is a hydrophobic amino acid selected from the group consisting of I, L, V and M;

$X_5$ is a hydrophobic amino acid selected from the group consisting of I, L and V;

$X_6$ is a polar or charged amino acid selected from the group consisting of R, K, Q and E;

$X_7$ is any amino acid;

$X_8$ is a hydrophobic amino acid selected from the group consisting of I, L, V and A; and $X_9$ is a hydrophobic amino acid selected from the group consisting of I, V, L and M (SEQ ID NO: 79).

Preferably, the BMC-targeting signal polypeptide comprises a sequence selected from the group consisting of LEQIIRDVL (SEQ ID NO:1), LETLIRTIL (SEQ ID NO:2), LETLIRNIL (SEQ ID NO:3), LRQIIEDVL (SEQ ID NO:4), IEEIVRSVM (SEQ ID NO:5), IEQWKAVL (SEQ ID NO:6), VEKLVRQAI (SEQ ID NO:7), IQEIVRTLI (SEQ ID NO:8), VEEIVKRIM (SEQ ID NO:9), IESMVRDVL (SEQ ID NO:10), VQDIIKNW (SEQ ID NO:11), IRQWQEVL (SEQ ID NO:12), VRSWEEW (SEQ ID NO:13) and ARDLLKQIL (SEQ ID NO:14) or a variant thereof, more preferably LEQIIRDVL (SEQ ID NO: 1) or a variant thereof, or LETLIRNIL (SEQ ID NO: 3) or LRQIIEDVL (SEQ ID NO: 4) or a variant thereof, most preferably LETLIRNIL (SEQ ID NO:3) or LRQIIEDVL (SEQ ID NO: 4) or a variant thereof.

Preferably, the BMC-targeting signal polypeptide comprises a sequence selected from the group consisting of the sequences shown in the table below:

| SEQ ID NO: | Sequence |
|---|---|
| 15 | (V/I)(V/Y)G(Q/K)(V/A/G/E)(Y/S/Q)(I/V/L/F) (N/Q/S/L)(K/Q/R)(M/L)(L/M/R)(V/L/C/Q) (T/S)(L/M)FP(H/D/E)(R/N/Q) |
| 16 | (L/F)(S/P/A)(P/V)(E/Q)Q(A/S/Q/W)(Q/E/R) RIY(R/Q)G(S/N) |
| 17 | M(D/N)(E/Q)(K/Q)(Q/E)(L/I)(K/R/E)(E/D) (I/M)(V/I)(R/E)(S/Q)(V/I)(L/M)A(E/Q/S) |
| 18 | (A/K/S)(E/D)(A/E)L(I/V)(E/D/N)(L/E/S) (I/L)(V/I)(R/K/E/Q)(K/R)VL(E/A)(E/K)L |
| 19 | MEI(N/D/T)E(K/E)(L/V)(L/V)(R/E)Q(I/V) (I/V)(E/K/A)(D/E)VL(K/S/R/A)(E/D) |
| 20 | (M/I)(N/D)(T/E)(D/K)(A/L)(I/L)E(S/E)(M/I) V(R/K)(D/E/Q)VL(S,N)(M/L)(N/E/G)S |
| 21 | M(N/D/E)(T/S/E)(S/L)E(L/V)E(T/Q/K/D)(L/I) (I/V)(R/K)(T/N/K)(I/V)(L/I)(S/L/R/N)E |
| 22 | (A/P)(K/G)(S/Q)(S/D)(L/A)(T/N)E(E/Q)(D/Q) (I/V)Y(D/E)AVK(K/R)(V/I)(L/I)(E/G)(Q/E/S) (H/S)G(A/S)LD(P/V) |
| 23 | MN(D/T)(I/T)(E/Q)(I/L)(A/E)(Q/N)(A/M) (V/I)(S/R/A)(T/K/N)IL(S/A/E/R)(D/K) (N/F/Y)(T/L/G)K |
| 24 | LD(A/E)ES(A/V)(A/G)D(M/I)(T/A)E(M/Q)I (A/L)K(E/G)(L/M)(K/Q)(E/D)AG |
| 25 | (D/P)(D/N)(A/E)(D/E/A)L(V/I)A(E/A/S)IT (K/R)(K/R/Q)V(M/L)(A/E)QL(G/K) |
| 26 | VNEQ(L/M)VQDIV(Q/R/K)EVVA(K/R)MQI(S/T) |
| 27 | DQE(A/Q)LV(K/Q)(A/L)IT(D/E)(Q/R/E)VMA (A/E)L(K/S)K |
| 28 | MQ(I/A)(D/T)EE(L/A)IRSVV(A/Q)(Q/E)VL(A/S) (E/Q)(V/L)(G/N) |
| 29 | (E/Q/D)(N/E/D)(V/I/L)(E/Q)(R/Q/D)(I/L/V) (I/L/V)(K/R/N)(E/Q/K)(V/I/L)(L/I/V)(E/Q/G) (Q/R/A)(L/M)(K/G/S) |
| 30 | M(A/D)(K/I/N/L)(R/Y)(E/N/S/L/F)(T/S)(P/N) (R/K)(V/L/F)(K/A)(E/V/M)(L/A)(A/T)(E/K) (R/N)(L/M) |
| 31 | I(E/D/G)ALR(A/E/D)ELR(A/R)L(V/I)(V/A)EEL (A/R)(Q/E)L(I/N/G)(K/R)(R/Q) |

More preferably, the BMC-targeting signal polypeptide comprises a sequence selected from the group consisting of SEQ ID NO: 15, 17, 18, 19, 20, 21, 22, 23, 26, 28 and 29.

More preferably, the BMC-targeting signal polypeptide comprises a sequence selected from the group consisting of SEQ ID NO:19, SEQ ID NO:20 and SEQ ID NO:21. Still more preferably, the BMC-targeting signal polypeptide comprises a sequence selected from SEQ ID NO: 19 and SEQ ID NO:21.

Preferably, the BMC-targeting signal polypeptide comprises a sequence selected from the group consisting of the sequences shown in the table below:

| SEQ ID NO: | Sequence |
|---|---|
| 32 | (V/I)(V/Y)G(Q/K)(V/A/G/E)(Y/S/Q)(I/V/L/F) (N/Q/S)(K/Q/R)(M/L)(L/M)(C/Q)(T/S)(L/M)FP (H/D/E)(R/N/Q) |
| 17 | M(D/N)(E/Q)(K/Q)(Q/E)(L/I)(K/R/E)(E/D) (I/M)(V/I)(R/E)(S/Q)(V/I)(L/M)A(E/Q/S) |
| 33 | (A/K/S)(E/D)(A/E)L(I/V)(E/D/N)(E/S)(I/L) (V/I)(R/K/E/Q)(K/R)VL(E/A)(E/K)L |
| 34 | MEI(N/D/T)E(K/E)(L/V)(L/V)(R/E)Q(I/V) (I/V)(E/K)(D/E)VL(K/S/R/A)(E/D)(M/L) |
| 20 | (M/I)(N/D)(T/E)(D/K)(A/L)(I/L)E(S/E)(M/I) V(R/K)(D/E/Q)VL(S,N)(M/L)(N/E/G)S |
| 21 | M(N/D/E)(T/S/E)(S/L)E(L/V)E(T/Q/K/D)(L/I) (I/V)(R/K)(T/N/K)(I/V)(L/I)(S/L/R/N)E |
| 22 | (A/P)(K/G)(S/Q)(S/D)(L/A)(T/N)E(E/Q)(D/Q) (I/V)Y(D/E)AVK(K/R)(V/I)(L/I)(E/G)(Q/E/S) (H/S)G(A/S)LD(P/V) |
| 35 | MN(D/T)(I/T)(E/Q)(I/L)(E)(Q/N)(A/M)(V/I) (S/R)(T/K/N)IL(S/A/E/R)(D/K)(N/F/Y) (T/L/G)K |
| 26 | VNEQ(L/M)VQDIV(Q/R/K)EVVA(K/R)MQI(S/T) |
| 36 | MQ(I/A)(D/T)EE(L/A)IRSVVQ(Q/E)VL(A/S) (E/Q)(V/L)(G/N) |
| 37 | (E/Q/D)(N/E/D)(V/I/L)(E/Q)(R/Q/D)(I/L/V) (I/L/V)(K/R/N)(E/Q/K)(V/I/L)(L/I/V)(E/Q/G) (Q/R/A)(L/M)(K/G/S) |

More preferably, the BMC-targeting signal polypeptide comprises a sequence selected from the group consisting of SEQ ID NO: 34, SEQ ID NO:20 and SEQ ID NO:21. Still more preferably, the BMC-targeting signal polypeptide comprises a sequence selected from SEQ ID NO: 34 and SEQ ID NO:21.

Preferably, the BMC-targeting signal polypeptide comprises a sequence selected from the group consisting of the sequences shown in the table below, or a variant thereof:

| SEQ ID NO: | Sequence |
|---|---|
| 38 | VYGKEQFLRMRQSMFPDR |
| 39 | LAPEQQQRIYRGN |
| 40 | MDQKQIEEIVRSVMAS |
| 41 | MNQQDIEQVVKAVLLKM |
| 42 | NTELVEEIVKRIMKQL |
| 43 | MEINEKLLRQIIEDVLRDM |
| 44 | MEINEKLLRQIIEDVLRD |
| 45 | MEINEKLLRQIIEDVLSE |
| 46 | MNTDAIESMVRDVLSRMNS |
| 47 | MNTSELETLIRTILSE |
| 48 | MNTSELETLIRNILSE |
| 49 | MNTSELETLIRNILSEQL |
| 50 | AGTNYTEEQVFAAVKKVLNSSGSTDV |

-continued

| SEQ ID NO: | Sequence |
|---|---|
| 51 | MVAKAIRDHAGTAQPSGNA |
| 52 | IDIILAQQITVQIVKELKERG |
| 53 | DNADLVASITRKVMEQLG |
| 54 | VNEQLVQDIIKNVVASMQLT |
| 55 | EPEDNEDVQAIVKAIMAKLNL |
| 56 | DTEMLVKMITEQVMAALKK |
| 57 | MQATEQAIRQVVQEVLAQLN |
| 58 | EVEALVQRLTEEILRQLQ |
| 59 | IDETLVRSVVEEVVRAF |
| 60 | EDARDLLKQILQALS |
| 61 | MDIREFSNKFVEATKNM |
| 62 | LDALRAELRALVVEELAQLIKR |
| 63 | MALREDRIAEIVERVLARL |

Preferably, the BMC-targeting signal polypeptide comprises a sequence selected from the group consisting of SEQ ID Nos: 40, 41, 42, 43, 44, 45, 46, 47, 48, 49, 54, 57, 59 and 60 or a variant thereof.

Preferably, the BMC-targeting signal polypeptide comprises a sequence selected from the group consisting of SEQ ID NOs: 43, 44, 45, 47, 48 and 49 or a variant thereof. More preferably, the BMC-targeting signal polypeptide comprises a sequence selected from the group consisting of 45, 48 or 49 or a variant thereof.

The microorganisms of the invention may comprise variants of any nucleic acid or polypeptide sequence disclosed herein, e.g. variants of the disclosed BMC-targeting signal polypeptides. By "variant" is meant a sequence with at least 75% identity (sequence identity) to the sequence disclosed herein. e.g. to the sequence of a disclosed BMC-targeting signal polypeptide. As used herein, variants retain the same function as the nucleic acid or polypeptide of which they are a variant. Variant BMC-targeting signal polypeptides have the function of directing the polypeptide to which they are attached to a BMC, if present.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. To determine the percent sequence identity of two amino acid sequences, the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence is occupied by the same amino acid residue as the corresponding position in the other sequence, then the molecules are identical at that position. "Identity" and "similarity" can be readily calculated by known methods, such as but not limited to Clustal and BLAST.

Preferably, a variant sequence has at least 80%, 81%, 82%, 83%, 84%, 85%, 86%, 87%, 88%, 89%, 90%, 91%, 92%, 93%, 94%, 95%, 96%, 97%, 98% or 99% identity to the sequence to which it is compared, e.g. to the BMC-targeting signal polypeptides disclosed herein.

Preferably, a variant amino acid sequence as referred to herein comprises no more than 6, more preferably no more than 5, more preferably no more than 4, more preferably no more than 3, more preferably no more than 2, most preferably no more than 1 mismatch(es) with the sequence to which it is compared, e.g. to a BMC-targeting signal polypeptide disclosed herein. A mismatch is a non-identical amino acid in the same position.

Preferably the variant sequences comprise only conservative substitutions as compared to the original amino acid sequence. A "conservative amino acid substitution" is one in which the amino acid residue is replaced with an amino acid residue having a similar side chain. In the context of the present invention, a conservative amino acid substitution is the replacement of a hydrophobic amino acid with another hydrophobic amino acid, the replacement of a polar amino acid with another polar amino acid or the replacement of a charged amino acid with another charged amino acid.

The microorganism of the present invention is essentially free of BMCs. As used herein, the term "essentially free of BMCs" means essentially free of functional BMCs. A functional BMC is a BMC with the morphology as seen in a microorganism that naturally expresses the BMC. Such organisms are well-known in the art and the morphology of naturally occurring functional BMCs is well-characterised.

BMCs are functional when they have an intact capsule, i.e. a closed shell. Such a morphology is termed a closed capsule morphology herein. Disruptions in BMC formation can lead to improperly formed BMCs that are not fully closed. Functional and non-functional BMCs, i.e. those with and without the correct closed capsule morphology can be readily identified by a number of techniques known in the art, e.g. by transmission electron microscopy. Preferably, the microorganism of the invention is essentially free of closed BMCs. Preferably the microorganism of the invention is essentially free of functional and improperly formed BMCs, i.e. those with and without a closed capsule morphology, i.e. closed and un-closed shells.

Preferably, the microorganism is essentially free of one or more, preferably all of Pdu, Eut and carboxysome BMCs. As mentioned above, preferably, the microorganism of the invention does not naturally express, i.e. comprise, BMCs. Preferably, the microorganism of the invention does not naturally express any BMCs.

Preferably, the microorganism is of a species or strain that does not naturally express BMCs. Alternatively viewed, the microorganism of the invention is preferably of a species or strain that lacks the genes necessary for the formation of BMCs. Such microorganisms are entirely free of BMCs, i.e. they lack BMCs. In the case of microorganism species or strains that do not produce BMCs naturally, the microorganisms of the present invention of the same species or strains are entirely free of said BMCs, and this is achieved simply by not genetically engineering the microorganisms to provide BMC production capability. Clearly, microorganisms that are not bacteria lack any BMCs. Furthermore, the vast majority of sequenced bacterial species lack BMCs.

In an alternative preferred embodiment, the microorganism of the invention is of a species or strain that naturally expresses BMCs but has been modified to reduce, i.e. it comprises modifications that reduce, essentially all of the cell's ability to express BMCs. In other words, the microorganism of the invention is preferably of a species or strain that naturally expresses BMCs but has been modified to reduce essentially all of the ability to express BMCs. Thus, in such microorganisms, the native ability of the cell to express (i.e. produce) BMCs is interrupted, inhibited, or deleted, i.e. such that it expresses no more than de minimis level of BMCs.

Alternatively viewed, preferably the microorganism of the invention is of a species or strain that naturally comprises BMCs but has been genetically modified to inhibit essentially all BMC formation. In other words, the microorganism is of a species or strain that possesses the genes necessary for the formation of BMCs but has been modified such that essentially all BMC formation is inhibited, interrupted or deleted, i.e. such that it produces no more than de minimis level of BMCs.

In the embodiments in which the microorganism of the invention is of a strain that naturally comprises the genes necessary for the expression of BMCs, the microorganism of the invention preferably comprises a loss of function mutation in one or more of said genes. Preferably, the microorganism comprises loss of function mutations in at least one gene encoding a protein comprising a BMC domain and at least one gene encoding a protein comprising a bacterial microcompartment vertex domain. Preferably, the microorganism comprises a loss of function mutation in the regulatory region of the BMC operon(s) that are present in the naturally occurring microorganism strain, preferably in the operon's promoter.

In the embodiments in which the microorganism of the invention is of a strain that naturally comprises the genes necessary for the expression of BMCs, the microorganism of the invention preferably comprises a disruption in one or more of said genes. Preferably, the microorganism comprises a disruption in at least one gene encoding a protein comprising a BMC domain and at least one gene encoding a protein comprising a bacterial microcompartment vertex domain. Preferably, the microorganism comprises a disruption in the regulatory region of the BMC operon(s) that are present in the naturally occurring microorganism strain, preferably in the operon's promoter.

As mentioned above, a loss of function mutation is a disruption of a gene. A loss of function mutation, i.e. disruption, may comprise complete or partial inactivation of the gene, for instance by missense mutations, nonsense mutations, insertions, deletions, duplications, frameshift mutations, repeat expansions and any combination thereof.

Thorough analyses of bacterial genomes have been performed to identify species that comprise BMC genes (US 2012/0210459, Axen et al., (2014) *PLOS Computational Biology* 10(10):e1003898 and Jorda J, et al., (2013) *Protein Science: A Publication of the Protein Society.* 22(2):179-195). It was determined that 23 different types of BMCs were encoded in 30 distinct locus (sub)types found in 23 bacterial phyla. Dataset S1 of Axen et al. comprehensively lists sequenced bacterial species that naturally comprise BMCs.

By "essentially free of BMCs" is meant that the microorganism is in essence free of BMCs but it does not mean that there is a strict requirement for the microorganism to lack BMCs entirely. There is potential for a de minimis level of BMC production even after steps have been taken to inhibit the production of BMCs. This is because microorganisms are biological systems that cannot be as precisely controlled as, for instance, mechanical or chemical systems. For instance, random genetic mutation could, in rare instances, lead to the expression of BMC capsule proteins. While a detailed inspection may reveal that some BMCs are present, they are present in such small quantities that for the purposes intended they can be considered absent. The microorganism of the invention is essentially free of BMCs if it has been genetically modified to inhibit essentially all BMC formation. Preferably, the microorganism is free, i.e. entirely free of BMCs.

In any case, the level of BMC production in the microorganisms of the present invention is essentially zero. In embodiments in which the microorganism is of a strain that naturally produces BMCs, the level of BMC production in the microorganism of the present invention is preferably at most 10%, more preferably at most 5%, still more preferably at most 1% of the level of BMC production in the same strain that has not been modified according to the invention. The person of ordinary skill in the art will readily be able to determine the extent of BMC production in a cell or population of cells, for instance by transmission electron microscopy of sectioned cells, and quantifying relative protein levels by SDS gel electrophoresis.

Genetically engineering a microorganism to be essentially free of one or more types of BMC would be within the competencies of one of ordinary skill in the art and any suitable approach may be used. The genes required for BMC formation are well characterised, for instance in US 2012/0210459, Chowdhury et al., (2014) *Microbiol. Mol. Biol. Rev.* 78(3): 438, and Axen et al., (2014) *PLOS Computational Biology* 10(10):e1003898.

Preferably, one or more of the proteins required for BMC formation are down-regulated in the microorganism of the present invention. By down-regulated is meant that the level of expression of said protein is in the microorganism of the invention is at most 10%, preferably at most 5%, more preferably at most 1% of the level of expression of said protein in a microorganism of the same strain that has not been modified according to the invention. As used herein, down-regulation of a protein is equivalent to down-regulation of a gene encoding that protein, and vice versa. Most preferably, the microorganism of the invention lacks the one or more proteins required for BMC formation, i.e. the microorganism is one in which the protein or the gene encoding said protein has been eliminated. Most preferably, the microorganism of the invention lacks the one or more genes required for BMC formation, i.e. the microorganism is one in which the one or more genes required for BMC formation have been eliminated.

Genetic engineering techniques for down-regulating and eliminating the expression of a gene/protein of interest are well-known in the art and any such technique may be used in the context of the present invention. Preferably, the microorganism of the invention comprises a deletion, interruption or deleterious mutation in one or more of the genes encoding a protein required for BMC formation that results in the reduction or elimination of expression of said protein. Alternatively, the relevant gene may be silenced using a short DNA or RNA oligonucleotide that has a sequence complementary to either gene or an mRNA transcript, e.g. antisense oligonucleotides.

The down-regulated protein required for formation of functional BMCs (i.e. BMCs having an intact, closed capsule) is preferably either:

i) a protein comprising a BMC-domain. A BMC domain is a domain common to the majority of known BMC shell proteins. The BMC domains are typically flat hexamers that tile edge to edge to form extended protein sheets; or ii) a pentameric bacterial microcompartment vertex (BMV) protein. These proteins are non-BMC-domain shell proteins that form the vertices of the BMC capsule.

Both BMC-domain containing proteins and BMV proteins are required for the formation of intact, closed BMCs. Preferably, the microorganism of the present invention is essentially free of closed BMCs.

Preferably, the expression of one or more proteins comprising a BMC domain is down-regulated in the microorganism of the present invention. Preferably the expression of one or more BMV proteins is down-regulated in the microorganism of the present invention. Preferably, the expression of at least one protein comprising a BMC domain and at least one protein comprising a BMV domain is down-regulated in the microorganism of the invention.

As mentioned above, a number of types of BMCs are known in the art, including Pdu BMCs, Eut BMCs, and carboxysomes. Throughout, "Pdu" stands for "propanediol utilization" and Eut" stands for "ethanolamine utilization". In nature, BMC proteins are typically expressed from the same operon as the proteins, e.g. enzymes, that comprise BMC-targeting polypeptides and that localise within the BMCs. For example, in the Pdu operon, the Pdu BMC proteins are expressed from the same operon as the Pdu enzymes. Some naturally occurring microorganisms express more than one type of BMC. For instance, *Salmonella* possesses the genes necessary for expression of both Pdu and Eut BMCs.

In bacteria that naturally express Pdu BMCs, it is known that the formation of functional BMCs with closed capsules requires at least the expression of the BMC shell proteins PduA, B, B', J, K, M, N, T and U. Preferably, the expression of PduA, B, B', J, K, M, N, T or U or any combination thereof is down-regulated in the microorganisms of the present invention. Preferably, the expression of PduN is down-regulated. PduN is known to be the BMV protein of the closed Pdu BMC and it has been shown previously that PduN deletion mutants form grossly abnormal, non-functional BMCs. Preferably the expression of PduB and PduB' are down-regulated. PduBB' deletion mutants have been shown previously to be unable to form BMCs. Preferably the expression of PduJ is down-regulated. PduJ deletion mutants have been shown previously to be unable to form functional BMCs.

Preferably, the expression of PduN, B, B', J, M or A or any combination thereof is down-regulated. Preferably, the expression of PduN, B, B', J or A or any combination thereof is down-regulated, particularly preferably when the microorganism is *Salmonella*. Preferably, the expression of PduN and any one or more of Pdu B, B', J, M and A is down-regulated. Preferably, the expression of PduN, B, B', J, M and A is down-regulated. Preferably, the expression of PduA, B, B', J, K, N, T and U is down-regulated. Preferably, the expression of PduN, B, B', J and A is down-regulated, particularly preferably when the microorganism is *Salmonella*. Preferably, the expression of PduA, B, B', J, K, M, N, T and U is down-regulated.

Preferably, the expression of pduB, pduB', pduJ, or pduN or any combination thereof is down-regulated, most preferably the expression of pduB, pduB', pduJ, and pduN is down-regulated.

In bacteria that naturally express Eut BMCs, it is known that the formation of functional, closed BMCs requires at least the expression of the BMC shell proteins EutK, M, S, L and N. Preferably, the expression of EutK, M, S, L or N or any combination thereof is down-regulated in the microorganisms of the present invention. Preferably, the expression of EutN is down-regulated. EutN is known to be the BMV protein of the closed Eut BMC. Preferably, the expression of EutN and any one or more of EutK, M, S and L is down-regulated. Preferably, the expression of EutN, EutM, Eut S and EutL are down-regulated. Preferably, the expression of EutK, M, S, L and N are down-regulated.

In bacteria that naturally express the alpha-carboxysome, it is known that the formation of functional, closed BMCs requires at least the expression of the proteins CsoS1 A-D, CsoS2 and CsoS4. Preferably, the expression of CsoS1 A-D, CsoS2 or CsoS4 is down-regulated. Preferably, the expression of CsoS1 A-D and CsoS2 is down-regulated. Preferably, the expression of CsoS1 A-D and CsoS4 is down-regulated. Preferably, the expression of CsoS2 and CsoS4 is down-regulated. Preferably, the expression of CsoS1 A-D, CsoS2 and CsoS4 is down-regulated.

In bacteria that naturally express the beta-carboxysome, it is known that the formation of functional, closed BMCs requires at least the expression of the proteins CcmK2, CcmO and CcmL. Preferably, the expression of CcmK2, CcmO or CcmL is down-regulated. Preferably the expression of CcmK2 and CcmO is down-regulated. Preferably the expression of CcmK2 and CcmL is down-regulated. Preferably the expression of CcmO and CcmL is down-regulated. Preferably the expression of CcmK2, CcmO and CcmL is down-regulated. Preferably the expression of CcmK1, 3 and 4 are also down-regulated.

The glycyl radical enzyme(GRM)-associated bacterial microcompartments can vary in the number and type of shell proteins in the operon. These shell proteins are homologues to the shell proteins of the other BMC systems and belong to the same protein families. Like the Pdu BMC, the GRM BMC comprise s hexamers and pentamers, and the pentamers form the vertices of the BMC capsule. In bacteria that naturally express the GRM BMC, preferably the pentameric protein (Pfam03319) is down-regulated.

Preferably, if a microorganism of the invention is of a species that naturally expresses a particular BMCs type or types, then the microorganism of the invention comprises a deletion or deleterious mutation in a regulatory region of the operon for the production of said BMC type or types, preferably in the promoter. Preferably, if a microorganism of the invention is of a species that naturally expresses a particular BMCs type or types, then the microorganism of the invention comprises a deletion of the operon for the production of said BMC type or types. In other words, if a microorganism of the invention is of a species that naturally expresses a particular BMCs type or types, then the microorganism of the invention is preferably a BMC null mutant. A BMC null mutant is a microorganism that has been modified such that it is devoid of any endogenous genes for the production of BMCs.

As mentioned above, in nature, microorganisms that naturally express BMCs typically do so only under certain conditions, namely in the presence of the substrate for the pathway that comprises steps catalysed by enzymes located within the BMCs. For instance, Pdu BMCs are only expressed by microorganisms comprising the necessary genes when said microorganisms are exposed to 1,2-propanediol. Similarly, Eut BMCs are only expressed by microorganisms comprising the necessary genes when said microorganisms are exposed to ethanolamine.

Thus, in an alternative embodiment, the microorganism of the invention is of a species or strain that naturally expresses BMCs, i.e. that comprises the genes necessary for the expression of BMCs, but wherein said microorganism is in an environment, e.g. a culture medium, that does not permit expression of BMCs. In other words, preferably the microorganism is present in a culture medium that lacks the molecule(s) that induce(s) the expression of BMCs in the microorganism. If the microorganism naturally expresses Pdu BMCs, then said molecule is 1,2-propanediol. If the microorganism expresses Eut BMCs, then said molecule is ethanolamine. The use of such limited culture media may remove the need for genetic modification of a microorganism to ensure lack of BMC expression.

In another aspect, the present invention provides a method of producing a genetically modified microorganism as described herein, said method comprising transforming a microorganism with one or more heterologous nucleic acid molecules together encoding at least three different proteins, each protein comprising an enzymatic domain and a bacterial microcompartment-targeting signal polypeptide, wherein said enzymatic domains catalyse different substrate to product conversions in the same metabolic pathway, and wherein said microorganism is essentially free of BMCs The features and embodiments described above in relation to the genetically modified microorganisms of the invention apply mutatis mutandis to the methods of producing a genetically modified microorganism disclosed herein. The microorganisms, one or more heterologous nucleic acid molecules, at least three proteins, enzymatic domains, BMC-targeting signal polypeptides, substrate to product conversions, products of interest, and BMCs are as defined above.

In said method, preferably the microorganism is transformed with one or more plasmids, vectors or transformation cassettes comprising said one or more nucleic acid molecules. Preferably, said vector is an expression vector, preferably also comprising a strong heterologous promoter operatively linked to said one or more nucleic acid molecules.

If the microorganism is of a species or strain that naturally expresses BMCs, then the method comprises the step of genetically modifying the microorganism to inhibit essentially all BMC formation. Such steps are as described above. Alternatively, the method comprises culturing the microorganism only in an environment, e.g. a culture medium, that does not permit expression of BMCs, i.e. that lacks the molecule(s) that induce(s) the expression of BMCs in the microorganism.

Alternatively viewed, the present invention provides a method of producing a genetically modified microorganism as described herein, said method comprising over-expressing in a microorganism one or more heterologous nucleic acid molecules together encoding at least three different proteins, each protein comprising an enzymatic domain and a bacterial microcompartment-targeting signal polypeptide, wherein said enzymatic domains catalyse different substrate to product conversions in the same metabolic pathway, and wherein said microorganism is essentially free of BMCs As explained above, preferably said microorganism is naturally free of BMCs, i.e. is of a strain that does not naturally express BMCs. In an alternative preferred embodiment however, the microorganism of the invention is of a strain that naturally expresses BMCs, therefore, the above methods preferably comprise a step of modifying the microorganism or its environment to inhibit its ability to produce said BMCs, as described above. Said inhibitions are preferably complete inhibitions.

Preferably, the step of modifying the microorganism to inhibit its ability to produce said BMCs comprises the step of down-regulating one or more of the proteins required for BMC formation. Preferably, the step of modifying the microorganism to inhibit its ability to produce said BMCs comprises the step of eliminating one or more of the proteins required for BMC formation. Preferably, said steps comprise deleting, interruption or deleteriously mutating one or more of the genes encoding a protein required for BMC formation that results in the reduction or elimination of expression of said protein. Alternatively, the method comprises silencing the one or more genes using a short DNA or RNA oligonucleotide that has a sequence complementary to either gene or an mRNA transcript, e.g. antisense oligonucleotides.

Preferably, if a microorganism of the invention is of a species that naturally expresses a particular BMCs type or types, then the microorganism of the invention comprises a deletion or deleterious mutation in a regulatory region of the operon for the production of said BMC type or types, preferably in the promoter. Preferably, if a microorganism of the invention is of a species that naturally expresses a particular BMCs type or types, then the microorganism of the invention comprises a deletion of the operon for the production of said BMC type or types. In other words, if a microorganism of the invention is of a species that naturally expresses a particular BMCs type or types, then the microorganism of the invention is preferably a BMC null mutant. A BMC null mutant is a microorganism that has been modified such that it is devoid of any endogenous genes for the production of BMCs.

The discussion of preferred down-regulated proteins in the context of the microorganisms of the invention applies mutatis mutandis to the methods of producing the microorganisms of the invention.

In another aspect, the present invention provides a method of producing a product of interest, said method comprising growing a genetically modified microorganism described herein under conditions wherein the product is produced and optionally recovering the product. Said methods comprise growing the genetically modified microorganism under conditions in which said at least three different proteins are expressed, and preferably wherein said proteins together form aggregates.

The methods of the present invention comprise growing, i.e. culturing, a microorganism of the present invention under conditions that produce the product of interest. Any such conditions can be used and the person of ordinary skill in the art will readily be able to select and optimise the conditions for their specific purposes. Typically, the microorganism will be grown in a culture medium. If the microorganism of the invention is a strain that naturally expresses BMCs, then preferably the method does not comprise the step of applying to the culture medium any inducer molecule(s) that induce the expression of said BMCs in said microorganism. Preferably, the method does not comprise the step of applying propanediol, ethanolamine, choline, fucose or rhamnose.

The methods of the present invention thus comprise fermentation. "Fermentation" as used herein is the bulk growth of microorganisms on a growth medium, with the aim of producing a specific product by a metabolic process. Although fermentation is optionally a process that converts sugar to acids, gases or alcohols, it is not limited to these substrates or products as used herein.

Typically, the microorganisms of the present invention are grown in fermentation media for production of a product of interest. Defined or synthetic growth media may also be used and the appropriate medium for growth of a particular microorganism will be known by one skilled in the art of microbiology or fermentation science.

Fermentation media for production of the products of interest are well-known in the art and the skilled person will readily be able to determine a suitable fermentation media for their specific purpose. An appropriate, or effective, fermentation medium refers to any medium in which a genetically modified microorganism of the present invention, when cultured, is capable of producing the product of interest. Such a medium is typically an aqueous medium comprising assimilable carbon, nitrogen and phosphate sources. Such a medium can also include appropriate salts, minerals, metals and other nutrients.

Carbon sources are well-known in the art and the skilled person will readily be able to determine the appropriate carbon source for the microorganism species being used and the product of interest. It is contemplated that the source of carbon utilized can encompass a wide variety of carbon containing substrates and will only be limited by the choice of organism. Sources of assimilable carbon which can be used in a suitable fermentation medium include, but are not limited to, sugars and their polymers, including, dextrin, sucrose, maltose, lactose, glucose, fructose, mannose, sorbose, arabinose and xylose; fatty acids; organic acids such as acetate; primary alcohols such as ethanol and n-propanol; and polyalcohols such as glycerol. Preferred carbon sources include monosaccharides, disaccharides, and trisaccharides. The most preferred carbon source is glucose or glycerol. The concentration of a carbon source in the fermentation medium should promote cell growth, but not be so high as to repress growth of the microorganism used.

Sources of assimilable nitrogen which can be used in a suitable fermentation medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids.

The fermentation medium can contain other compounds such as inorganic salts, vitamins, trace metals or growth promoters. Such other compounds can also be present in carbon, nitrogen or mineral sources in the effective medium or can be added specifically to the medium. The fermentation medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. A suitable fermentation medium can also include a source of magnesium, preferably in the form of a physiologically acceptable salt, such as magnesium sulfate heptahydrate, although other magnesium sources in concentrations which contribute similar amounts of magnesium can be used.

The fermentation medium can also include a biologically acceptable chelating agent, such as the dihydrate of trisodium citrate. The fermentation medium can also include a biologically acceptable calcium source, including, but not limited to, calcium chloride. The fermentation medium can also include sodium chloride. Preferably, the culture medium lacks the molecule(s) that induce(s) the expression of BMCs in the microorganism. Alternatively viewed, the present invention provides a culture medium comprising a microorganism of the invention, wherein said culture medium lacks the molecule(s) that induce(s) the expression of BMCs in the microorganism. Such molecules are described above. Preferably, the culture media lacks one or more, preferably all of propanediol, ethanolamine, choline, fucose and rhamnose.

The microorganisms of the invention described herein can be cultured using standard laboratory or industrial techniques known in the art. The growth of the microorganisms described herein can be measured by methods known in the art, for instance by measuring the optical density (OD) of cell cultures over time.

The temperature of the fermentation medium can be any temperature suitable for growth and production of the product of interest. For example, prior to inoculation of the fermentation medium with an inoculum, the fermentation medium can be brought to and maintained at a temperature in the range of from about 20° C. to about 45° C., preferably to a temperature in the range of from about 25° C. to about 40° C.

The pH of the fermentation medium can be controlled by the addition of acid or base to the fermentation medium. In such cases when ammonia is used to control pH, it also conveniently serves as a nitrogen source in the fermentation medium. Preferably, the pH is maintained from about 3.0 to about 9.0, more preferably from about 4 to about 8.0, still more preferably from about 6.5 to about 7.5, most preferably about 7.4.

Fermentations can be performed under aerobic or anaerobic conditions. The fermentation medium can also be maintained to have a dissolved oxygen content during the course of fermentation to maintain cell growth and to maintain cell metabolism for production of the product of interest. The oxygen concentration of the fermentation medium can be monitored using known methods, such as through the use of an oxygen electrode. Oxygen can be added to the fermentation medium using methods known in the art, for example through agitation and aeration of the medium by stirring or shaking. Preferably, the oxygen concentration in the fermentation medium is in the range of from about 20% to about 100% of the saturation value of oxygen in the medium based upon the solubility of oxygen in the fermentation medium at atmospheric pressure and at a temperature in the range of from about 20° C. to about 40° C. Periodic drops in the oxygen concentration below this range may occur during fermentation, however, without adversely affecting the fermentation.

Although aeration of the medium has been described herein in relation to the use of air, other sources of oxygen can be used. Particularly useful is the use of an aerating gas which contains a volume fraction of oxygen greater than the volume fraction of oxygen in ambient air. In addition, such aerating gases can include other gases which do not negatively affect the fermentation.

Although the carbon source concentration can be maintained within desired levels by addition of, for example, a substantially pure glucose solution, it is acceptable, and may be preferred, to maintain the carbon source concentration of the fermentation medium by addition of aliquots of the original fermentation medium. The use of aliquots of the original fermentation medium may be desirable because the concentrations of other nutrients in the medium (e.g. the nitrogen and phosphate sources) can be maintained simultaneously.

The amount of product in the fermentation medium can be determined using a number of methods known in the art, for example, high performance liquid chromatography (HPLC) or gas chromatography (GC).

A batch method of fermentation can be used with the microorganisms described herein. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells progress through a static lag phase to a high growth log phase and finally to a stationary phase where growth rate is diminished or halted. If untreated, cells in the stationary phase will eventually die. Cells in log phase generally are responsible for the bulk of production of end product or intermediate.

A Fed Batch system can also be used with the microorganisms described herein. A Fed Batch system is similar to a typical batch system with the exception that the carbon source substrate is added in increments as the fermentation progresses. Fed Batch systems are useful when catabolite repression (e.g. glucose repression) is apt to inhibit the metabolism of the cells and where it is desirable to have limited amounts of substrate in the media. Measurement of the actual substrate concentration in Fed Batch systems is difficult and is therefore estimated on the basis of the changes of measurable factors such as pH, dissolved oxygen and the partial pressure of waste gases such as $CO_2$. Batch and Fed Batch fermentations are common and well known in the art.

Although a batch mode can be performed, it is also contemplated that continuous fermentation methods could also be performed with the microorganisms described herein. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to vary. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology.

It is contemplated that the present invention can be practiced using either batch, fed batch or continuous processes and that any known mode of fermentation would be suitable. Additionally, it is contemplated that cells can be immobilized on a substrate as whole cell catalysts and subjected to fermentation conditions for production.

Products can be isolated from the fermentation medium by methods known to one skilled in the art. For instance, solids may be removed from the fermentation medium by centrifugation, filtration, decantation, or the like. Products of interest in solution may be isolated from the fermentation medium using methods such as distillation, azeotropic distillation, liquid-liquid extraction, adsorption, gas stripping, membrane evaporation, pervaporation or vacuum flash fermentation.

In another aspect, the present invention comprises a cell free system, said system comprising aggregates comprising at least three different proteins, each protein comprising an enzymatic domain and a bacterial microcompartment-targeting signal polypeptide, wherein said enzymatic domains each catalyse a different substrate to product conversion in the same metabolic pathway, and wherein said system does not comprise bacterial microcompartments.

The system is suitable for the production of a product of interest, wherein said enzymatic domains each catalyse a different substrate to product conversion in the same metabolic pathway for the production of said product of interest.

The features and embodiments described above in relation to the genetically modified microorganisms of the invention apply mutatis mutandis to the cell free systems disclosed herein. The microorganisms, one or more heterologous nucleic acid molecules, at least three proteins, enzymatic domains, BMC-targeting signal polypeptides, substrate to product conversions, products of interest, and BMCs are as defined above.

The conditions of the cell free system preferably mimic in vivo conditions. It would be within the competencies of one of ordinary skill in the art to modify the conditions in the cell free system to suit their particular purposes and the particular proteins employed. Preferably the pH of the system is one at which the enzymatic domains can function and the proteins remain aggregated. Preferably, the system comprises a buffer. Preferably, the pH of the system is between 5 and 9. Suitable buffers are well-known in the art. For example, a potassium phosphate buffer (pH 8) may be used, for instance at a concentration of about 100 mM.

Depending on the proteins, particularly the enzymatic domains present in the system, the system may or may not comprise a salt solution. Preferably, the cell free system comprises said aggregates and an aqueous solution, preferably a salt solution, for instance comprising NaCl and/or $MgCl_2$. Optionally, the NaCl is present at a concentration of about 100 mM. Optionally the $MgCl_2$ is present at a concentration of about 2.5 mM. If present, the solution is preferably an aqueous solution.

Preferably, the system comprises the co-factors necessary for the catalytic activity of the enzymatic domains of the at least three proteins in the system, for instance NADH, for instance at a concentration of about 0.1 mM. The skilled person will be aware of the appropriate cofactors for any particular enzymatic domain. Preferably, the system comprises ATP, for instance at a concentration of about 1 mM.

Preferably, the system comprises potassium phosphate buffer (pH 8), NaCl, NADH, MgCl2, McCl2 and ATP. Preferably, the system comprises about 100 mM potassium phosphate buffer (pH 8), about 100 mM NaCl, about 0.1 mM NADH, about 2.5 mM MgCl2, about 0.1 mM McCl2 and about 1 mM ATP.

Preferably, the system comprises cell lysate obtained from a population of microorganisms of the present invention. Preferably, the cell free system is prepared by culturing the microorganism of the invention, suspending the cultured cells in an aqueous solution and lysing them to result in a cell lysate. The cell lysate will comprise the desired protein aggregates since the aggregates will have formed in the microorganism during the culturing step.

Optionally, one or more purification steps can be performed to remove unwanted cellular fractions and/or to selectively isolate the aggregates. For instance, exclusion fractionation/chromatography may be used and the aggregates isolated by centrifugation. Various methods of cellular fractionation are well known in the art, as are methods for the isolation of proteins of interest including those in aggregated form. Suitable methods are disclosed, for instance, in Principles and Techniques of Practical Biochemistry (Wilson, K. & Walker, J) Cambridge University Press 5$^{th}$ Ed. Purification methods are disclosed, for instance, in Rodriguez-Carmona et al. (2010) *Microbial Cell Factories* 9:71.

It will be within the competencies of one of ordinary skill in the art to adjust the composition and conditions of the cell free system for his/her intended purpose and depending on the nature of the at least three proteins therein. For instance, the skilled person will be aware of how the pH of a cell free system can be adjusted to ensure that the aggregated proteins remain aggregated and the enzymatic domains remain functional. Similar considerations will be given to the temperature and salt concentration of the system.

The enzymatic domains present within the aggregated proteins in the cell free system each catalyse a different substrate to product conversion in the same metabolic pathway, i.e. in a pathway for the production of a product of interest. Preferably, the cell free system therefore comprises a suitable level of substrate(s) for the production of the product of interest.

In another aspect, the present invention provides a method of producing a product of interest, said method comprising:
i) providing a cell free system comprising aggregates comprising at least three different proteins, each protein comprising an enzymatic domain and a bacterial microcompartment-targeting signal polypeptide, wherein said enzymatic domains each catalyse a different substrate to product conversion in the same metabolic pathway for the production of the product of interest, and wherein said system does not comprise bacterial microcompartments;
ii) applying to said system the substrate of the first substrate to product conversion in the metabolic pathway that is catalysed by one of said enzymatic domains; and
iii) optionally recovering the product of interest.

The present invention provides a method of producing a product of interest, said method comprising:
i) growing a genetically modified microorganism described herein under conditions wherein said at least three proteins are expressed, preferably over-expressed, and wherein said proteins together form aggregates,
ii) obtaining said aggregates from said microorganisms, and
iii) using said aggregates in a cell free system for the production of said product of interest, under conditions wherein the product is produced;
and optionally recovering the product.

The cell free system is as described herein. Preferably, the step of obtaining said aggregates comprises lysing the microorganisms and obtaining the cell lysate, as described above.

As used herein, the singular forms "a," "an" and "the" include plural references unless the content clearly dictates otherwise. Thus, for example, reference to "a cell" includes a mixture of two or more cells.

The invention will now be further described in the following non-limiting Examples and the Figures in which:

FIG. 1 illustrates a pathway for the synthesis of 1,2-propanediol from glycerol. Glycerol dehydrogenase and dihydroxyacetone kinase catalyse the conversion of glycerol to dihydroxyacetone phosphate, via the intermedia dihydroxyacetone. Methylglyoxal synthase catalyses the conversion of dihydroxyacetone phosphate to methylglyoxal. Glycerol dehydrogenase and 1,2-propanediol oxidoreductase catalyse the conversion of methylglyoxal to 1,2-propanediol, via the intermediate lactaldehyde.

Figure 2:
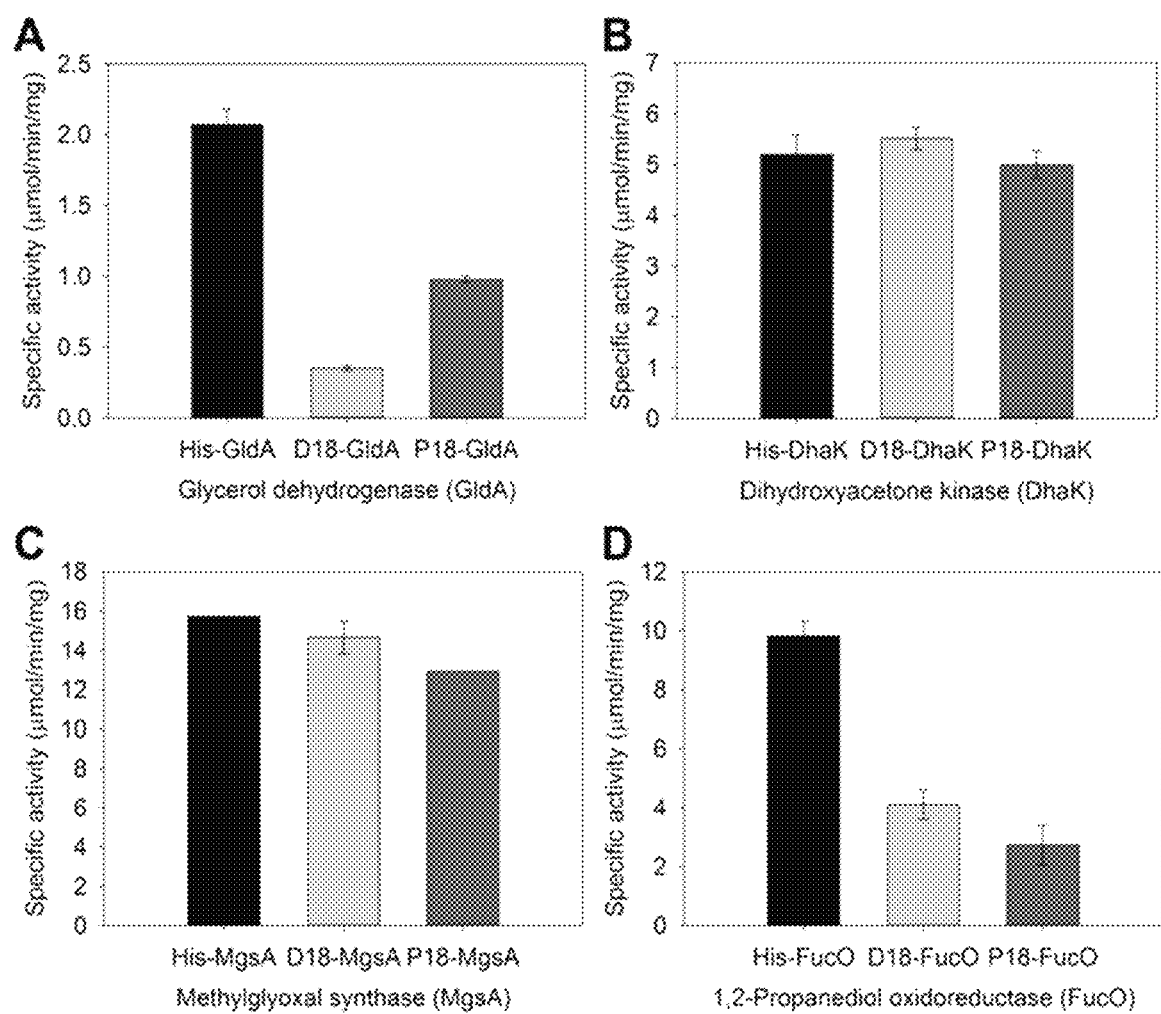

FIG. 2 shows the specific activity of the enzymes involved in the microbial synthesis of 1,2-propanediol: (a) glycerol dehydrogenase (b) dihydroxyacetone kinase (c) methylglyoxal synthase (d) 1,2-propanediol oxidoreductase, when untagged (i.e. not linked to a BMC-targeting signal sequence), when tagged with the BMC-targeting signal sequence D18 and when tagged with the BMC-targeting signal sequence P18.

Figure 3:
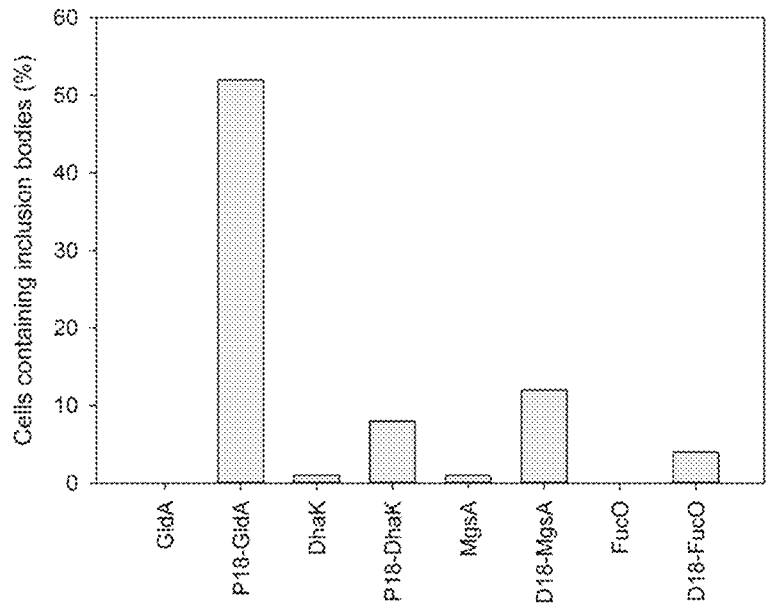

FIG. 3 provides a statistical analysis showing the percentage of cells that contan inclusion bodies when said cells express either untagged GldA, DhaK, MgsA or FucO, or P18- or D18-tagged versions of said proteins.

Figure 4:
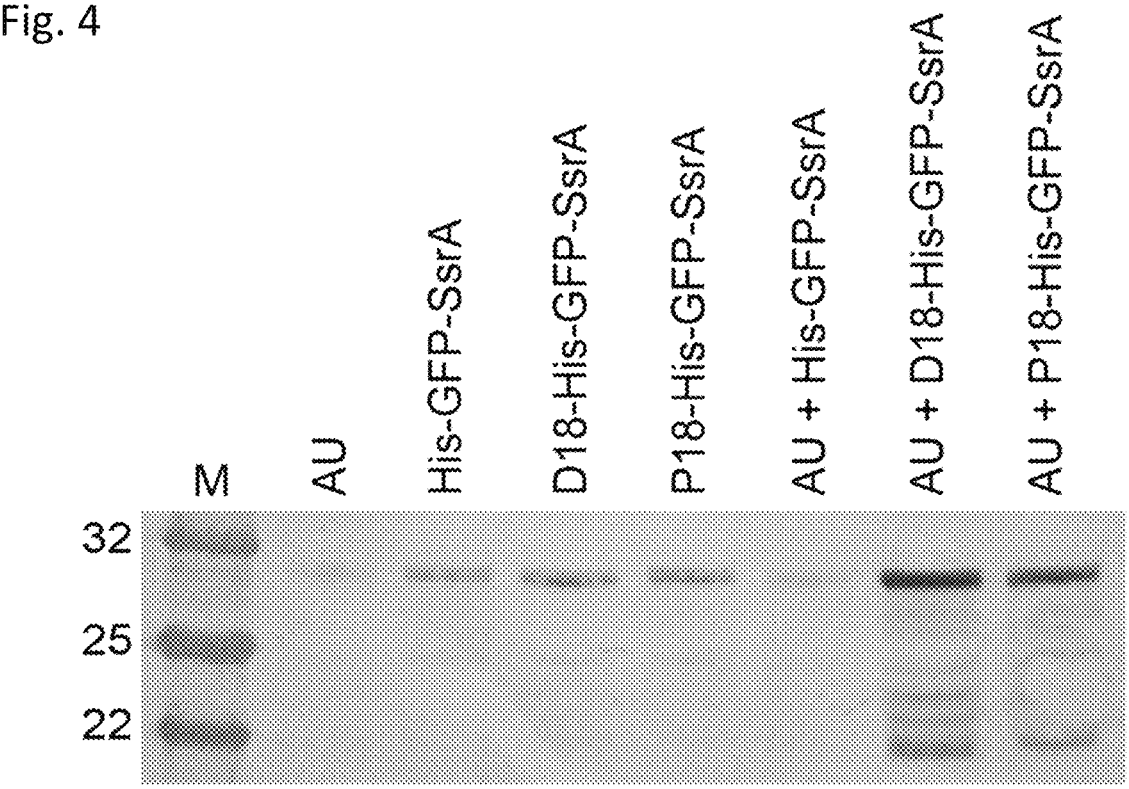

FIG. 4 shows the results of a protease protection assay of GFP fused to a C-terminal proteolysis tag (SsrA) and an N-terminal tag being either a BMC targeting signal peptide (P18 or D18) or a non-targeting His-tag, in the presence and absence of BMCs (AU). *E. coli* competent cells were transformed with plasmids encoding the protein fusions with and without shell proteins and the resulting strains were cultured for 24 hours, samples were taken and run on a 15% denaturing polyacrylamide gel. Gels were subsequently submitted to Western blotting using an anti-GFP primary antibody. Total lysates were analysed by SDS-PAGE and subsequently western blotted with an anti-GFP primary antibody. Cell densities were normalised to an $OD_{600}$=2.5 for loading of samples.

Figure 5:
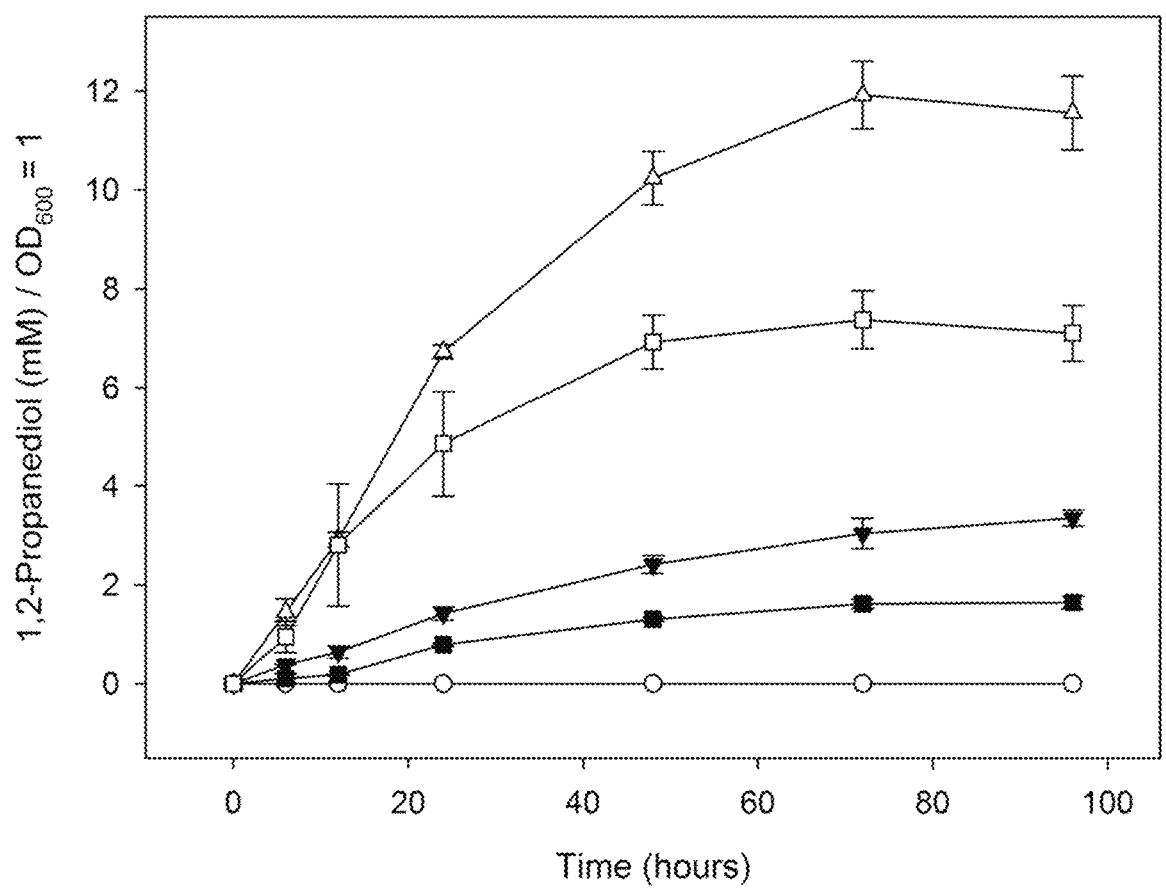

FIG. 5 shows in vivo 1,2-propanediol production. The graph shows the 1,2-propanediol content (normalised to $OD_{600}$=1) over 96 h in the growth medium of strains that lack shell proteins and 1,2-propanediol producing enzymes (●), Shell proteins only (○), un-tagged 1,2-propanediol producing enzymes (▼), 1,2-propanediol producing enzymes tagged with targeting sequences (Δ), un-tagged 1,2-propanediol producing enzymes and shell proteins (■), 1,2-propanediol producing enzymes tagged with targeting sequences and shell proteins (□). Data points represent an average of three independent experiments; standard deviations are represented by error bars.

Figure 6:
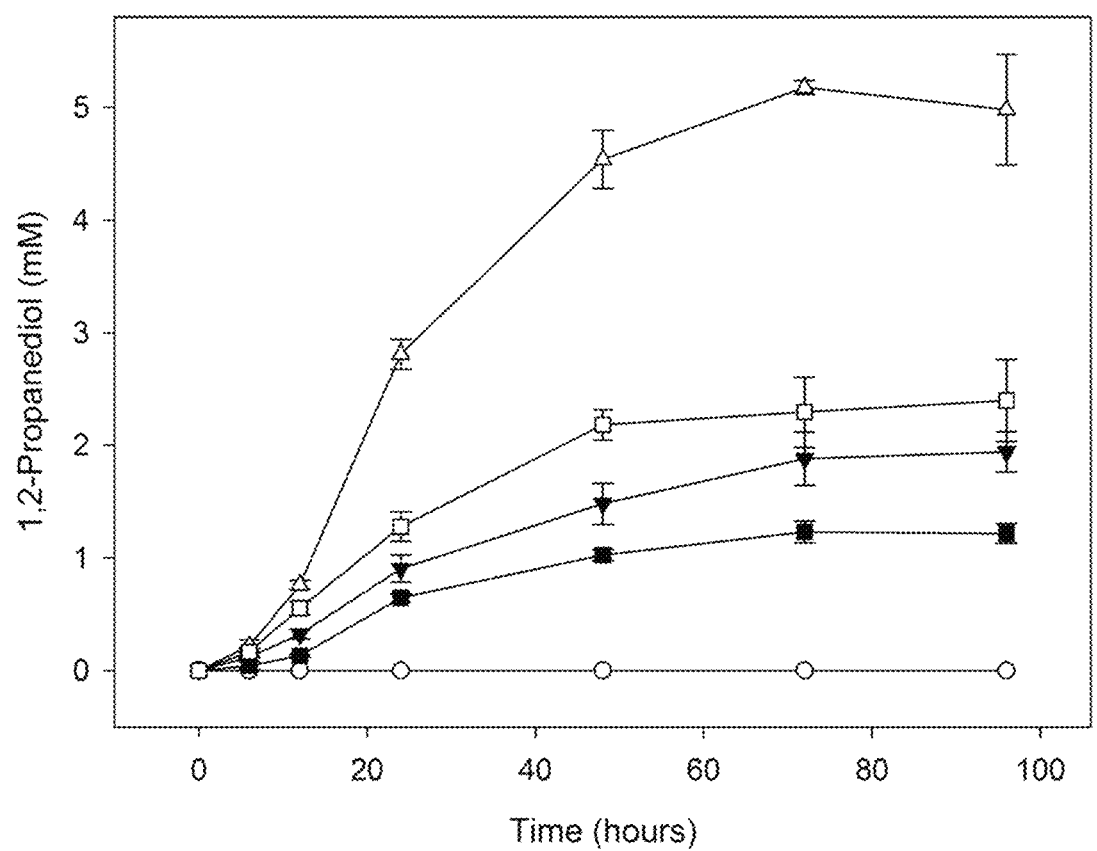

FIG. 6 shows in vivo 1,2-propanediol production. The graph shows the 1,2-propanediol content (not normalised to $OD_{600}$=1) over 96 h in the growth medium in of strains that lack shell proteins and 1,2-propanediol producing enzymes (●), Shell proteins only (○), un-tagged 1,2-propanediol producing enzymes (▼), 1,2-propanediol producing enzymes tagged with targeting sequences (Δ), un-tagged 1,2-propanediol producing enzymes and shell proteins (■), 1,2-propanediol producing enzymes tagged with targeting sequences and shell proteins (□). Data points represent an average of three independent experiments; standard deviations are represented by error bars.

Figure 7:
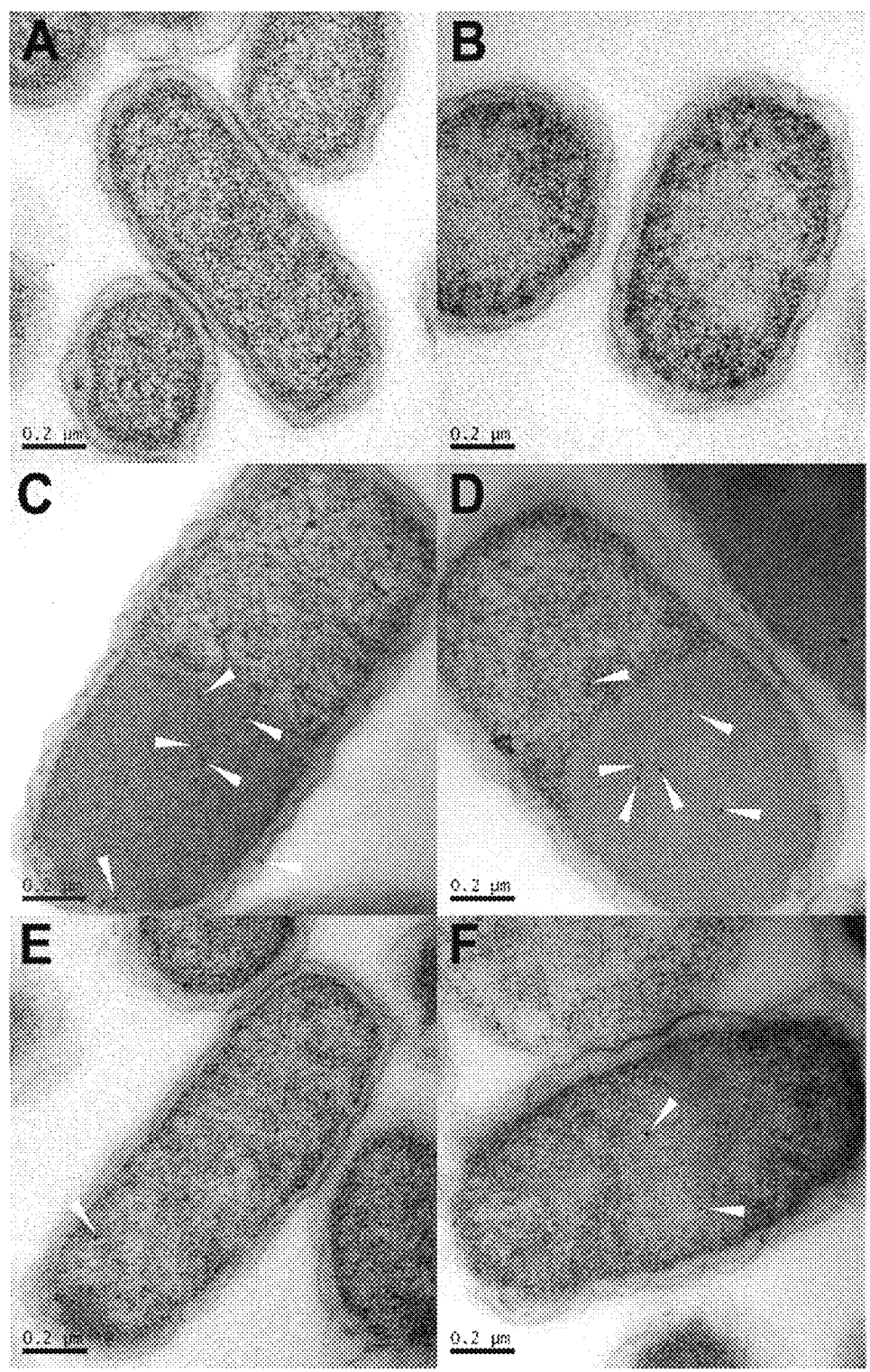

FIG. 7 shows thin sections of *E. coli* strains labelled with an anti-his antibody and then with a secondary antibody conjugated to 10 nm gold particles viewed under TEM (a) Wild type (b) Shell proteins only (c) 1,2-propanediol producing enzymes tagged with targeting sequences (d) 1,2-propanediol producing enzymes tagged with targeting sequences and shell proteins (e) un-tagged 1,2-propanediol producing enzymes (f) un-tagged 1,2-propanediol producing enzymes and shell proteins.

Figure 8:
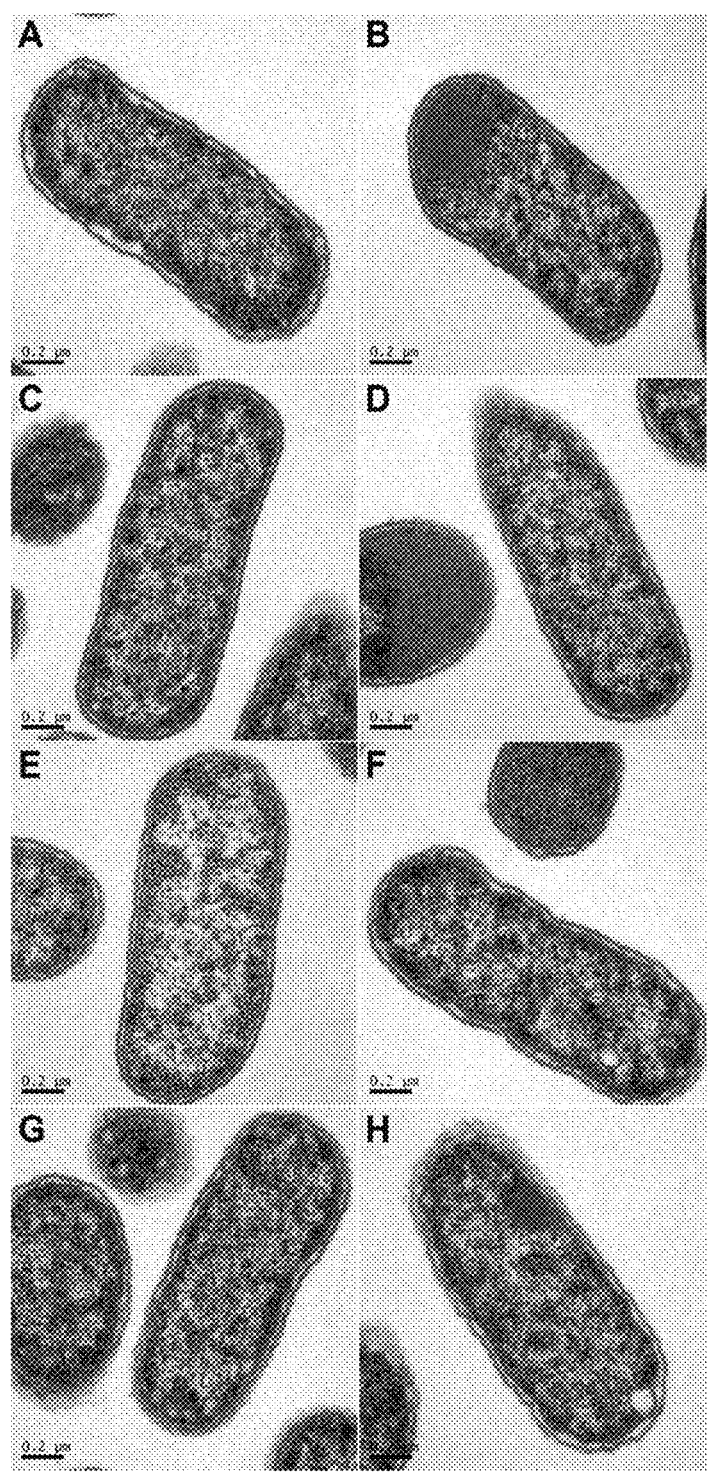

FIG. 8 shows TEM analysis of strains expressing (A) His-tagged GldA (B) P18-tagged GldA (C) His-tagged DhaK (D) P18-tagged DhaK (E) His-tagged MgsA (F) D18-tagged MgsA (G) His-tagged FucO (H) D18-tagged FucO. Scale bar shows 0.2 μM.

EXAMPLES

In this study we are creating fusion proteins between Pdu targeting peptides and the four 1,2-propanediol producing enzymes to target the enzymes to recombinant Pdu microcompartment shells. We explore how the targeting peptides affect the activity of the different enzymes and their properties, particularly solubility. Strains are engineered for the targeting of all enzymes to microcompartments and compared for their 1,2-propanediol production to strains containing the native enzymes and also to a strain containing enzymes with targeting peptides but no shell proteins. The protein solubility of these strains is investigated by TEM analysis and protein aggregation is found to play an unexpected but important role in the efficiency of our pathway. Finally, we propose an alternative pathway engineering approach alongside compartmentalisation in protein shells.

Materials and Methods

Strains

The strains used in this study are shown in Table A below:

TABLE A

| Strain | Genotype | Source |
|---|---|---|
| Strains used in this study | | |
| BL21*(DE3) | F- ompT hsdSB (rB- mB-) gal dcm (DE3) | Novagen |
| BL21*(DE3) pLysS | F- ompT hsdSB(rB- mB-) gal dcm (DE3) pLysS (CamR) | Novagen |

The BL21*(DE3) strain comprises genes encoding Eut BMCs. To ensure that Eut BMCs were not produced by the microorganisms during this study, ethanolamine was not included in any fermentation media. The absence of BMCs was confirmed by TEM.

Plasmid Construction

Plasmids were constructed to include each of the genes of interest with an N-terminal tag comprising a BMC-targeting signal polypeptide ("P18" or "D18") and/or a hexa-histidine tag.

The genes of interest were the four enzymes of the metabolic pathway for the production of 1,2-propanediol from glycerol, as outlined in FIG. 1, i.e. glycerol dehydrogenase (GldA), dihydroxyacetone kinase (DhaK), methylglyoxal synthase (MgsA) and 1,2-propanediol oxidoreductase (FucO).

The BMC-targeting signal polypeptide-containing tags used in the study were as follows:

"D18":
(SEQ ID NO: 64)
MEINEKLLRQIIEDVLSEPMGSSHHHHHHSSGLVPRGSH (N-terminal 18 amino acids of PduD from *Citrobacter freundii* (the BMC-targeting signal polypeptide) followed by flexible linker PMGSS, 6-his linker, flexible linker SSGL, thrombin cleavage site LVPRGS and amino acid linker H)

"P18":
(SEQ ID NO: 65)
MNTSELETLIRNILSEQLAMGSSHHHHHHSSGLVPRGSH (N-terminal 18 amino acids of PduP from *Citrobacter freundii* (the BMC-targeting signal polypeptide) followed by flexible linker AMGSS, 6-his linker, flexible linker SSGL, thrombin cleavage site LVPRGS and amino acid linker H)

All primers used in this study are listed in Table B below.

TABLE B

Oligonucleotide primers used in this study, restriction sites are underlined

| Name | Sequence 5'-3' |
|---|---|
| GldA_NdeI_FW | CAT<u>CATATG</u>GACCGCATTATTC AATCACC (SEQ ID NO: 66) |
| GldA_SpeI_RV | CAT<u>ACTAGT</u>TTATTCCCACTCT TGCAGG (SEQ ID NO: 67) |
| dhaK_NdeI_FW | CGC<u>CATATG</u>TCTCAATTCTTTT TTAACCAACGCACC (SEQ ID NO: 68) |
| dhaK_SpeI_RV | CAT<u>ACTAGT</u>TTAGCCCAGCTCA CTCTCCGC (SEQ ID NO: 69) |
| mgsA_NdeI_FW | CAT<u>CATATG</u>GAACTGACGACTC GCACTTTACC (SEQ ID NO: 70) |
| mgsA_SpeI_RV | CAT<u>ACTAGT</u>TTACTTCAGACGG TCCGCGAG (SEQ ID NO: 71) |
| fucO_NdeI_FW | CCG<u>CATATG</u>GCTAACAGAATGA TTCTG (SEQ ID NO: 72) |
| fucO_SpeI_RV | CCT<u>ACTAGT</u>TTACCAGGCGGTA TGG (SEQ ID NO: 73) |
| GFP_NdeI_FW | GTA<u>CATATG</u>AGCAAAGGAGAAG AACTTTTC (SEQ ID NO: 74) |
| GFP-SsrA_SpeI_RV | GAC<u>ACTAGT</u>TTAAGCTGCTAAA GCGTAGTTTTCGTCGTTTGCTG CTTTGTACAGCTCATCCATGCC (SEQ ID NO: 75) |

All genes were amplified with flanking NdeI and SpeI restriction sites and each was ligated into pET14b, pET14b-D18 and pET14b-P18 vectors using NdeI and SpeI restriction sites.

Plasmids pML-1 to pML-6 as outlined in Table C, were constructed by a 'Link and Lock' approach utilizing the compatible sticky ends formed by digestion with XbaI and SpeI (McGoldrick et al., (2005) *J Biol Chem* 14:1086-1094).

TABLE C

Plasmids used in this study

| Plasmid name | Genotype | Description | Source |
|---|---|---|---|
| pET14b | pET14b | Overexpression vector containing N-terminal polyhistidine-tag | Novagen |
| pET14b-D18 | pET14b-D18 | Overexpression vector containing an N-terminal D18 targeting tag and an N-terminal polyhistidine-tag | This study |
| pET14b-P18 | pET14b-P18 | Overexpression vector containing an N-terminal P18 targeting tag and an N-terminal polyhistidine-tag | This study |
| pLysS | PlysS | Overexpression vector | Novagen |
| pLysS-PduABB'JKNU | pLysS-PduABB'JKNU | Construct for expression of empty Pdu BMC | Parsons et al., 2010 |
| pET14b-gldA | pET14b-gldA | PCR product of gldA ligated into NdeI/SpeI sites of pET14b | This study |
| pET14b-dhaK | pET14b-dhaK | PCR product of dhaK ligated into NdeI/SpeI sites of pET14b | This study |
| pET14b-mgsA | pET14b-mgsA | PCR product of mgsA ligated into NdeI/SpeI sites of pET14b | This study |
| pET14b-fucO | pET14b-fucO | PCR product of fucO ligated into NdeI/SpeI sites of pET14b | This study |
| pET14b-GFP-SsrA | pET14b-GFP-SsrA | PCR product of gfp-ssrA ligated into NdeI/SpeI sites of pET14b | This study |
| pET14b-D18-gldA | pET14b-D18-His-gldA | NdeI/SpeI fragment of pET14b-gldA ligated into NdeI/SpeI sites of pET14b-D18 | This study |
| pET14b-D18-dhaK | pET14b-D18-His-dhaK | NdeI/SpeI fragment of pET14b-dhaK ligated into NdeI/SpeI sites of pET14b-D18 | This study |
| pET14b-D18-mgsA | pET14b-D18-His-mgsA | NdeI/SpeI fragment of pET14b-mgsA ligated into NdeI/SpeI sites of pET14b-D18 | This study |
| pET14b-D18-fucO | pET14b-D18-His-fucO | NdeI/SpeI fragment of pET14b-fucO ligated into NdeI/SpeI sites of pET14b-D18 | This study |
| pET14b-D18-GFP-SsrA | pET14b-D18-His-GFP-SsrA | NdeI/SpeI fragment of pET14b-GFP-SsrA ligated into NdeI/SpeI sites of pET14b-D18 | This study |
| pET14b-P18-gldA | pET14b-P18-His-gldA | NdeI/SpeI fragment of pET14b-gldA ligated into NdeI/SpeI sites of pET14b-P18 | This study |
| pET14b-P18-dhaK | pET14b-P18-His-dhaK | NdeI/SpeI fragment of pET14b-dhaK ligated into NdeI/SpeI sites of pET14b-P18 | This study |
| pET14b-P18-mgsA | pET14b-P18-His-mgsA | NdeI/SpeI fragment of pET14b-mgsA ligated into NdeI/SpeI sites of pET14b-P18 | This study |
| pET14b-P18-fucO | pET14b-P18-His-fucO | NdeI/SpeI fragment of pET14b-fucO ligated into NdeI/SpeI sites of pET14b-P18 | This study |
| pET14b-P18-GFP-SsrA | pET14b-P18-His-GFP-SsrA | NdeI/SpeI fragment of pET14b-GFP-SsrA ligated into NdeI/SpeI sites of pET14b-P18 | This study |

TABLE C-continued

Plasmids used in this study

| Plasmid name | Genotype | Description | Source |
|---|---|---|---|
| pML-1 | pET14b-His-gldA-His-fucO | XbaI/EcoRI fragment from pET14b-His-fucO ligated into XbaI/EcoRI sites of pET14b-His-gldA | This study |
| pML-2 | pET14b-P18-gldA-D18-fucO | XbaI/EcoRI fragment from pET14b-D18-His-fucO ligated into SpeI/EcoRI sites of pET14b-P18-His-gldA | This study |
| pML-3 | pET14b-His-dhaK-His-mgsA | XbaI/HindIII fragment from pET14b-His-mgsA ligated into SpeI/HindIII sites of pET14b-His-dhaK | This study |
| pML-4 | pET14b-P18-dhaK-D18-mgsA | XbaI/HindIII fragment from pET14b-D18-His-mgsA ligated into SpeI/HindIII sites of pET14b-P18-His-dhaK | This study |
| pML-5 | pET14b-His-dhaK-His-mgsA-His-gldA-His-fucO | XbaI/ClaI fragment from pML-3 ligated into SpeI/ClaI sites of pML-1 | This study |
| pML-6 | pET14b-P18-dhaK-D18-mgsA-P18-gldA-D18-fucO | XbaI/ClaI fragment from pML-4 ligated into SpeI/ClaI sites of pML-2 | This study |

Overexpression and Purification of Recombinant Protein

BL21*(DE3) pLysS competent cells were transformed with a plasmid containing the gene(s) of interest. 1 L of LB supplemented with ampicillin (100 mg/L) in baffled flasks was inoculated from an overnight starter culture. The cultures were grown at 37° C. with shaking for 7 hours; protein production was induced by the addition of IPTG to a final concentration of 400 µM. The cultures were then incubated overnight at 19° C. with shaking. Cells were harvested by centrifugation at 3320×g for 15 minutes at 4° C., pellets were resuspended in 20 mM Tris-HCl, pH 8.0, 500 mM NaCl, 5 mM Imidazole. Cells were lysed by sonication and cell debris removed by centrifugation. Recombinant protein was then purified from the soluble fraction by immobilized metal ion affinity chromatography.

Activity Assays

Glycerol Dehydrogenase

The activity of GldA for the oxidation of glycerol to dihydroxyacetone was measured by following the initial rate at 340 nm for the reduction of NAD+ to NADH. Activity assays were carried out in 1 ml reactions containing 0.1 M potassium phosphate buffer pH 8.0, 500 µM NAD+, 2 mM $MgCl_2$ and 200 nM GldA. The activity of GldA for the reduction methylglyoxal to lactaldehyde, was measured by following the initial rate of the oxidation of NADH to NAD+ at 340 nm. Activity assays were carried out in 1 ml reactions containing 0.1 M potassium phosphate buffer pH 8.0, 0.1 mM NADH, 2 mM MgCl2, 200 nM GldA.

Dihydroxyacetone Kinase

The activity of DhaK for the conversion of dihydroxyacetone to dihydroxyacetone phosphate was measured in a coupled reaction with Glyceraldehyde 3-phosphate dehydrogenase (G3PDH) by following the oxidation of NADH to NAD+ at 340 nm. Activity assays were carried out in 1 ml reactions containing 50 mM Tris-HCl, 100 mM NaCl, 1 mM ATP, 0.1 mM NADH, 2.5 mM $MgCl_2$, 7.2 U G3PDH, 125 nM DhaK.

Methylglyoxal Synthase

The activity of MgsA was monitored in a colorimetric assay over a time course. 25 µl 0.5 mM MgsA was incubated in a reaction mixture containing 400 µl 50 mM imidazole pH 7.0, 25 µl 15 mM dihydroxyacetone phosphate, 50 µl dH2O, the reaction mixture was incubated at 30° C. with shaking. At time intervals 50 µl of the reaction mixture was removed and added to a detection mixture containing 450 µl dH2O, 165 µl 0.1% 2,4-Dinitrophenylhydrazine hydrochloric acid solution. The detection mixture was incubated at 30° C. with shaking for 15 minutes. 835 µl of 10% (w/v) NaOH was added to the detection mixture which was incubated at room temperature for 15 minutes. Absorbances were then measured at 550 nm.

1,2-Proanediol Oxidoreductase

The activity of FucO was determined for the NADH dependant reduction of glycolaldehyde to elthylene glycol was measured by following the initial rate of the oxidation of NADH to NAD+ at 340 nm. Activity assays were carried out in 1 ml reactions containing 100 mM Hepes, 10 µM NADH, 100 µM MnCl2, 200 nM FucO.

Embedding of Strains for TEM Analysis 50 ml of LB was inoculated with one colony and grown at 37° C. with shaking to an OD600 of ~0.4, cells were harvested by centrifugation at 3000×g for 10 minutes. The cell pellet was resuspended in 2 ml 2.5% Glutaraldehyde in 100 mM cacodylate pH 7.2 and incubated for 2 hours with gentle spinning. Cells were pelleted by centrifugation at 6000×g for 2 minutes and were washed twice with 100 mM cacodylate pH 7.2. Cells were stained with 1% osmium tetroxide in 100 mM cacodylate pH 7.2 for 2 hours and subsequently washed twice with dH2O. Cells were dehydrated by incubation in an ethanol gradient, 50% EtOH for 10 minutes, 70% EtOH overnight followed by two 10 minute washes in 100% EtOH. Cells were then washed twice with propylene oxide for 15 minutes. Cell pellets were embedded by resuspention in 1 ml of a 1:1 mix of propylene oxide and Agar LV Resin and incubated for 30 minutes with spinning. Cell pellets were washed twice in 100% Agar LV resin. The cell pellet was resuspended in fresh resin and transferred to a 0.5 ml mould, centrifuged for 5 minutes at 3000×g to concentrate the cells to the tip of the mould and incubated for 16 hours at 60° C. to polymerise.

Sectioning and Visualisation of Samples

Samples were thin sectioned on a RMC MT-XL ultramicrotome with a diamond knife (diatome 45°) sections were placed on 300 mesh copper grids. Grids were stained by incubation in 4.5% uranyl acetate in 1% acetic acid solution for 1 hour followed by 2 washes in dH$_2$O. Grids were then stained with 0.1% lead citrate for 8 minutes followed by a wash in ddH$_2$O Electron microscopy was performed using a JEOL-1230 transmission electron microscope.

Culture Medium and Conditions for 1,2-Propanediol Production

The culture medium designed by Neidhardt et al., 1974 was supplemented with 30 g/L glycerol, 10 g/L tryptone, 5 g/L yeast extract and appropriate antibiotics. Strains were cultured in sealed serum bottles with a working volume of 100 ml at 28° C. with shaking. Cultures were inoculated from starter cultures to starting OD$_{600}$ of 0.05. During growth 1 ml samples were removed at 0, 6, 12, 24, 48, 72 and 96 hours.

Western Blot Analysis

Nitrocellulose membranes following transfer and blocking were incubated in primary antibody (mouse anti-GFP) followed by incubation in a secondary coupled antibody (Anti-mouse IgG AP). Bands were visualised by incubation in substrate 5-Bromo-4-chloro-3-indolyl phosphate/Nitro blue tetrazolium (BCIP/NBT).

Analysis of 1,2-Propanediol Production

In-vivo 1,2-propanediol production was determined by GC/MS analysis of the growth medium at time intervals (0, 6, 12, 24, 48, 72 and 96 hours). The supernatant after centrifugation, was boiled for 10 minutes at 100° C. followed by centrifugation at 19,750×g. The sample was then acidified with trifluoroacetic acid to a final concentration of 0.01% followed by a second centrifugation at 19,750×g. The supernatant following centrifugation was diluted 1:4 in acetonitrile for GC/MS analysis.

Visualisation of Engineered Strains

Embedding of Strains for Immunolabeling

Strains were grown as described previously ("Culture medium and conditions for 1,2-propanediol production", above) overnight, cells were harvested by centrifugation for 10 minutes at 3000×g. The cell pellet was resuspended in 2% formaldehyde, 0.5% gluteraldehyde in 100 mM sodium cacodolate buffer pH 7.2 and incubated for 2 hours with gentle spinning. Cells were pelleted by centrifugation at 6000×g for 2 minutes and were washed twice with 100 mM sodium cacodylate pH 7.2. Cells were dehydrated by incubation in an ethanol gradient, 50% EtOH for 10 minutes, 70% EtOH for 10 minutes, 90% EtOH for 10 minutes, followed by three 15 minute washes in 100% EtOH. Cell pellets were then resuspended in 2 ml LR white resin and incubated overnight with spinning at room temperature after which the resin was changed and incubated for a further 6 hours. Cell pellets were resuspended in fresh resin and transferred to 1 ml embedding tubes and centrifuged at 4000×g to pellet the cells at the tip and incubated for 24 hours at 60° C. to polymerize.

Samples were thin sectioned on a RMC MT-XL ultramicrotome with a diamond knife (diatome 45°) sections were placed on 300 mesh gold grids.

Immunolabeling of Sections

Grids were equilibrated in one drop of TBST (20 mM Tris-HCl pH 7.2, 500 mM NaCl, 0.05% Tween (RTM) 20, 0.1% BSA) before being transferred into a drop of 2% BSA in TBST and incubated at room temperature for 30 minutes. Grids were then immediately transferred into primary antibody (Anti-His) and incubated for 1 hour. Grids were washed in a fresh drop of TBST followed by washing in a stream of TBST. Grids were equilibrated in a drop of secondary antibody (Goat anti-mouse IgG 10 nm) then incubated for 30 minutes in a fresh drop. Excess antibody was removed by washing in two drops of TBST before washing in a stream of ddH$_2$O and dried.

Staining

Grids were stained for 15 minutes in 4.5% uranyl acetate in 1% acetic acid solution followed by 2 washes in dH$_2$O. Grids were then stained with 0.1% lead citrate for 3 minutes followed by a wash in ddH$_2$O.

Electron microscopy was performed using a JEOL-1230 transmission electron microscope.

Results

Effect of Fusing Enzymes to BMC-Targeting Peptides on Enzyme Specific Activities The effect of fusing either of the two targeting peptides P18 and D18 to heterologous enzymes on the functionality of those enzyme had not previously been investigated in detail. In this study the enzymes involved in the microbial synthesis of 1,2-propanediol from glycerol, namely glycerol dehydrogenase (GldA), dihydroxy acetone kinase (DhaK), methylglyoxal synthase (MgsA) and 1,2-propanediol oxidoreductase (FucO) were cloned with both N-terminal targeting peptides (P18 or D18) followed by a hexa-histidine tag. Proteins of interest were purified by IMAC and the kinetic parameters of each of the protein fusions were subsequently determined and compared to enzymes containing only the N-terminal hexa-histidine tag. In this Example, the term "tagged proteins" refers to P18-his and D18-his containing proteins, while the his-only containing proteins as referred to as "untagged" proteins.

It was found that the targeting peptides effect the specific activities of some of the proteins studied (FIG. 2). For instance, tagging GldA (the enzyme that catalyses the oxidation of glycerol) with the D18 targeting peptide resulted in a reduction of its specific activity by 90% compared to un-tagged GldA. Tagging GldA with the P18 targeting peptide reduced the activity of the protein by approximately half (55% reduction) compared to un-tagged GldA (FIG. 2A). GldA's ability to reduce methylglyoxal to lactaldehyde was similarly affected, with D18 having the greatest negative effect (83% reduction compared to un-tagged GldA) and P18 causing a loss of 53% of specific activity compared to untagged GldA. The activity of DhaK for the ATP dependant phosphorylation of dihydroxyacetone phosphate was determined by a coupled reaction involving a second enzyme, glyceraldehyde 3-phosphate dehydrogenase, in excess. In contrast to GldA, kinetic analysis of DhaK fused with either a P18 or D18 targeting peptide had no significant effect on the enzyme's activity (FIG. 2B).

Tagging MgsA with either a P18 or D18 targeting peptide had a negative effect on enzyme activity, reducing the activity by 18% and 15% respectively in comparison to untagged MgsA, as shown in FIG. 2C. When fused to D18, FucO's specific activity decreased by 58% in comparison to untagged FucO and when fused to P18, FucO's specific activity decreased by 76% in comparison to untagged FucO (FIG. 2D).

It is concluded that the fusion of targeting peptides to the N-termini of proteins is likely to have an effect on the specific activities of a significant proportion of said proteins. Without wishing to be bound by theory, the inventors consider this is most likely due to changes in structural and chemical properties and potential changes in protein folding as a result of the fusion.

Targeting Peptides Cause Protein Aggregation that can be Visualised by TEM

The production levels and solubility of GldA, DhaK, MgsA and FucO with and without targeting peptides fused thereto were investigated by subjecting samples of the purification process, including the soluble and insoluble fractions after clarification of the crude cell lysate as well as the final purified protein samples, to denaturing polyacrylamide gel analysis (data not shown). DhaK and MgsA were well produced and soluble irrespective of the presence of a P18 or D18 tag. The solubility of FucO was not affected by targeting peptides, but the yield of un-tagged FucO appeared slightly lower compared to FucO containing the targeting peptides. In contrast, although, both P18 and D18-tagged GldA appeared to be produced, the protein bands were predominantly detected in the insoluble fractions of the SDS gels.

This suggests that the fusion proteins D18-GldA and P18-GldA were aggregating compared to GldA. P18-GldA was also found to be eluted from the IMAC column with an additional band of smaller molecular weight, indicative of protein degradation.

In order to investigate the aggregation behaviour of the tagged proteins further, the most active protein fusions (P18-GldA, P18-DhaK, D18-MgsA and D18-FucO), the candidates for the construction of the 1,2-propanediol production pathway targeted to microcompartments, were chosen to be visualised by TEM.

Strains encoding each of the tagged proteins and strains encoding the un-tagged proteins were cultured overnight without induction. Subsequently, the cells were harvested, embedded in low viscosity resin, thin sectioned and visualized using TEM. For each strain 100 cells were examined for protein aggregation, statistical analysis of each of the strains is shown in FIG. 3 and representative TEM micrographs were compiled (FIG. 8).

Control strains producing un-tagged proteins (GldA, DhaK, MgsA, FucO) displayed a 'normal' phenotype, with only 1% of observed cells containing electron dense areas indicative of aggregated proteins. In contrast, half of all observed cells (52%) producing P18-GldA showed protein aggregates located at the pole of the cells (FIG. 8). The addition of the P18 targeting peptide to the N-terminus of DhaK resulted in aggregate formation in 8% of the observed cells. Fusion of the D18 targeting peptide to MgsA and FucO resulted in the presence of protein aggregates in 12% and 4% of cells respectively.

These results confirm that the fusions between the enzymes of the 1,2-propanediol production pathway and targeting peptides cause protein aggregation.

Enzymes Fused to BMC-Targeting Peptides are Recruited to BMCs

It was investigated whether fusion proteins comprising an enzyme of interest fused to either the P18 or D18 targeting peptide were targeted to bacterial microcompartments.

Strains co-expressing the individual genes of the 1,2-propanediol pathway (P18-gldA, P18-mgsA, D18-dhaK, D18-fucO) and the construct for empty shell formation (pLysS-PduABB'JKNU) were cultured and the recombinant microcompartments were purified as described previously (Lawrence et al., (2014) ACS Synth. Biol. 3: 454-465). Samples were taken throughout the purification and analysed on 15% denaturing polyacrylamide gels for the protein profile. Analysis of the resulting SDS-PAGE gels reveals that tagging each of the proteins with a targeting peptide facilitates their co-purification with the microcompartment proteins. This was further confirmed by kinetic assays of the final purified BMC fraction.

Further evidence of protein targeting to microcompartments was provided by a protease protection assay that was previously reported by Sargent et al., (2013) Microbiology 159: 2427-2436.

Plasmids were constructed containing GFP fused to an N-terminal P18 or D18 tag and a C-terminal SsrA proteolysis tag (AANDENYALAA*). The C-terminal SsrA tag targets proteins for degradation by the E. coli proteases ClpAP and ClpXP. E. coli competent cells were transformed with plasmids encoding the protein fusions with and without shell proteins and the resulting strains were cultured for 24 hours, samples were taken and run on a 15% denaturing polyacrylamide gel, adjusted to cell number as determined by $OD_{600}$ measurements. Gels were subsequently submitted to Western blotting using an anti-GFP primary antibody.

The results show that the co-expression of GFP-SsrA fused to targeting peptides and produced with shell proteins have the highest amount of GFP (FIG. 4 lane 7+8). In the absence of a targeting peptide GFP is effectively degraded as represented by only a faint band present in lane 6 of FIG. 4. In the absence of shell proteins, all GFP fusion proteins are present to a much lesser extent than fusion proteins in the presence of microcompartments. The faint bands seen could be a result of protein aggregation, which would protect the GFP fusions from proteolytic cleavage. The band seen in lane 1 of FIG. 4 (shell only) most likely represents unspecific binding of the antibody. The difference seen in band intensity between lanes 3 and 6 of FIG. 4 is likely due to differences in expression levels as a result of the co-expression of shell proteins.

These results are consistent with microcompartments providing protection from cytosolic proteases for proteins internalised therein.

Construction of 1,2-Propanediol Producing Strains and Comparative Analysis of Bacterial Growth For the in vivo production of 1,2-propanediol, single plasmids were engineered by using link and lock cloning combining firstly the genes coding for the most active protein fusions (pML-6 containing P18-his-gldA, P18-his-dhaK, D18-his-mgsA, D18-his-fucO) and secondly the same genes but without targeting sequences (pML-5 containing his-gldA, his-dhaK, his-mgsA, his-fucO). Both plasmids were used to transform the E. coli strain BL21*(DE3).

With the aim of targeting the 1,2-propanediol producing enzymes to recombinant microcompartments, strains were engineered to co-express the 1,2-propanediol production plasmids with the genes coding for the protein shell (pLysS-PduABB'JKNU). The shell protein construct allows for the formation of a microcompartment shell to which the fusion enzymes are recruited by virtue of their BMC-targeting peptide. Additionally, the following control strains were set up: firstly BL21*(DE3) transformed with pET14b and pLysS; and secondly, a shell only strain transformed with pET14b and pLysS-PduABB'JKNU. All strains were compared for the production of 1,2-propanediol.

The culture medium designed by Neidhardt et al., 1974 (Neidhardt F C, Bloch P L, Smith D F. Culture Medium for Enterobacteria. Journal of Bacteriology. 1974; 119(3):736-747) was supplemented with 30 g/L glycerol, 10 g/L tryptone and 5 g/L yeast extract and appropriate antibiotics. Strains were cultured in sealed serum bottles with a working volume of 100 ml at 28° C. with shaking The cultures were started with an initial $OD_{600}$ of 0.05 by inoculation from 5 ml starter cultures. During growth, 1 ml samples were collected at 0, 6, 12, 24, 48, 72 and 96 hours and optical densities at 600 nm were measured. The resulting growth curves (not shown) indicate that strains encoding proteins with targeting peptides (either with shell proteins or without) grow slower and reach a lower final optical density in comparison to strains expressing un-tagged proteins and control strains. Furthermore, cell densities declined from 24 hours in strains producing un-tagged enzymes whereas the cell densities of the strains with tagged enzymes remained constant, which indicates that cells with tagged enzymes cells are being protected from a toxic intermediate.

In Vivo 1,2-Propanediol Production is Elevated in Strains Producing Enzymes with Targeting Sequences The 1,2-propanediol content in the growth media of the various strains was quantified by gas chromatography-mass spectrometry (GC-MS). Whole cell samples were collected at 0, 6, 12, 24, 48, 72 and 96 hours and the supernatant following centrifugation was prepared for GC-MS analysis as described in materials and methods. The measured 1,2-propanediol content as shown in FIG. 5 is expressed for a cell density of $OD_{600}=1$. FIG. 6 shows the measured 1,2-propanediol content not adjusted for a cell density of $OD_{600}=1$.

Strains encoding un-tagged 1,2-propanediol producing enzymes with and without shell proteins showed low 1,2-propanediol production despite growing well and reaching the highest cell densities at 96 hours. Both strains reached the maximum product concentration (at 96 hours) of 3.59 mM/$OD_{600}=1$ in the absence of shell proteins and 1.95 mM/$OD_{600}=1$ in the presence of shell proteins.

The highest product concentrations were detected in the growth media of strains producing proteins tagged with targeting peptides. Although both of these strains (with and without shell proteins) grew to lower density than the strains harbouring un-tagged proteins, and despite the negative effect the targeting peptide has on the specific activities of the individual enzymes, they produced significantly more 1,2-propanediol (FIG. 5) than the strains lacking the targeting peptides. The strain containing tagged 1,2-propanediol enzymes and shell proteins reached a final yield of 7.10 mM/$OD_{600}=1$. However, the highest final yield of 11.56 mM/$OD_{600}=1$ was observed when the shell proteins were not present. 1,2-propanediol was not detected in control stains (wild type *E. coli* and a strain producing shell proteins only).

A comparison of FIG. 5 and FIG. 6 shows that the increase in 1,2-propanediol production levels is not simply an effect of differences in cell densities i.e. even though the strains with tagged enzymes don't grow as well as the strains without tagged enzymes, they still produce more 1,2-propanediol.

The higher product yield exhibited by the strain producing tagged enzymes in the absence of shell proteins was unexpected.

To investigate if aggregation of the proteins were causing this effect, electron microscopy and immunolabeling were used to visualise the subcellular organisation and location of the recombinant proteins in the various strains. Sections of the strains were labelled with anti-histidine primary antibody designed to bind to the hexa-histidine tag on the N-terminus of proteins in our pathway thereby revealing the intracellular location. A secondary antibody conjugated to 10 nm gold particles was used to bind to the primary antibody thereby revealing the intracellular location of 1,2-propanediol producing enzymes.

Control strains (wild type and shell only) showed a small amount of antibody binding around the membrane of the cells (FIGS. 7A and 7B); this is likely due to unspecific binding. Aggregates are visible in approximately 100% of observed cells expressing P18/D18-tagged proteins, regardless of the presence or absence of shell proteins, and it is in these areas that the vast majority of antibody binding occurs (FIGS. 7C and D). Such structures cannot be seen in cells expressing un-tagged enzymes (FIGS. 7E and F), suggesting that it is the presence of the targeting peptides that facilitates the aggregation of proteins.

It is concluded that aggregation occurs due to tagging proteins of interest with targeting peptides and it is this aggregation that results in a significant increase in product yield despite the reduction in specific activities of the individual tagged pathway enzymes.

It has been determined that the fusion of BMC-targeting peptides to the individual enzymes in the pathway for the production of 1,2-propanediol lowers the specific activities of the enzymes in some (most) cases. The solubility of each enzyme was also affected to varying degrees, with GldA forming large inclusion bodies in the majority of cells observed by TEM when fused with a targeting peptide compared to un-tagged GldA. It has also been demonstrated that the addition of a BMC-targeting tag recruited the enzymes to BMCs and that purified samples thereof remained metabolically active.

Despite the significant decrease of enzyme activity seen with the addition of targeting peptides to both GldA and FucO, expression of the complete tagged pathway enzymes led to an increase in product formation as compared to strains in which untagged enzymes were expressed. Rather unexpectedly, the presence of the microcompartment shell was not required for the increased product formation and, furthermore, the strain generating the most 1,2-propanediol produced tagged 1,2-propanediol pathway enzymes, but no shell proteins. This strain showed an increase in product formation of 245% OD-adjusted in comparison to the strain producing un-tagged enzymes; despite the lower in vitro activity of the individual tagged proteins compared to the un-tagged proteins.

TEM analysis showed that co-production of all four tagged enzymes resulted in protein aggregation and deposition at the poles of nearly all cells observed and it is this aggregation that appears to provide a significant benefit to the efficiency of the pathway. Aggregation of our proteins of interest is likely due to the amphipathic helical nature of the BMC-targeting sequences and/or by their coiled coil structure. Without wishing to be bound by theory, it can be considered that the aggregation creates a scaffolding effect that result in increased channeling of substrates and products between enzymes, similarly to the environment inside a microcompartment.

This study is the first to demonstrate that the presence of short targeting peptides can not only convert individual fusion proteins but also whole pathways into active aggregates that allow for increased product yield in vivo. These aggregations of multiple enzymes allow for increased localised concentrations of enzymes and intermediates and possibly channeling between them thereby resulting in a higher product yield. This is the first study to demonstrate that increased product yields can result from tagging enzymes in a metabolic pathway for the production of said product with a BMC targeting sequence in a cell lacking BMCs themselves.

The invention claimed is:

1. A genetically modified microorganism comprising one or more heterologous nucleic acid molecules together encoding at least three different proteins, each protein comprising an enzymatic domain and a bacterial microcompartment-targeting signal polypeptide,
   wherein said enzymatic domains each catalyse a different substrate to product conversion in the same metabolic pathway,
   wherein each of said proteins is a fusion protein comprising an enzymatic domain and a bacterial microcompartment-targeting signal polypeptide that are not present in the same protein in nature,
   wherein said microorganism is lacking bacterial microcompartments (BMCs), and
   wherein either (i) said microorganism does not naturally comprise the genes necessary for the expression of BMCs and has not been genetically engineered to provide BMC production capability, or (ii) said microorganism naturally comprises the genes necessary for the expression of BMCs but wherein said microorganism is a BMC null mutant.

2. The genetically modified microorganism of claim 1, wherein said microorganism comprises one or more heterologous nucleic acid molecules together encoding at least four different proteins, each protein comprising an enzymatic domain and a bacterial microcompartment-targeting signal polypeptide,
   wherein said enzymatic domains each catalyse a different substrate to product conversion in the same metabolic pathway.

3. The genetically modified microorganism of claim 1, wherein each of said heterologous nucleic acid molecules encodes only one of said proteins.

4. The genetically modified microorganism of claim 1, wherein each protein is over-expressed relative to the level of expression of said protein in a microorganism of the same strain which lacks said one or more heterologous nucleic acid molecules.

5. The genetically modified microorganism of claim 1, wherein said microorganism comprises aggregates comprising said at least three proteins.

6. The genetically modified microorganism of claim 1, wherein each protein comprises an enzymatic domain and a BMC-targeting signal polypeptide linked by an amino acid linker, preferably wherein said amino acid linker lacks stable secondary structure.

7. The genetically modified microorganism of claim 1, wherein each BMC-targeting signal polypeptide comprises an amphipathic alpha helix.

8. The genetically modified microorganism of claim 1, wherein each BMC-targeting signal polypeptide comprises the following amino acid sequence: $X_1X_2X_3X_4X_5X_6X_7X_8X_9$ (SEQ ID NO: 76), wherein:
   $X_1$, $X_4$, $X_5$, $X_8$, and $X_9$ are each independently hydrophobic amino acids selected from the group consisting of I, L, V, M, F, Y, A and W;
   $X_2$, $X_3$ and $X_6$ are each independently polar or charged amino acids selected from the group consisting of Q, N, T, S, C, D, E, R, K and H; and
   $X_7$ is any amino acid.

9. The genetically modified microorganism of claim 1, wherein each BMC-targeting signal polypeptide comprises a sequence selected from the group consisting of LEQIIRDVL (SEQ ID NO:1), LETLIRTIL (SEQ ID NO:2), LETLIRNIL (SEQ ID NO:3), LRQIIEDVL (SEQ ID NO:4), IEEIVRSVM (SEQ ID NO:5), IEQVVKAVL (SEQ ID NO:6), VEKLVRQAI (SEQ ID NO:7), IQEIVRTLI (SEQ ID NO:8), VEEIVKRIM (SEQ ID NO:9), IESMVRDVL (SEQ ID NO:10), VQDIIKNVV (SEQ ID NO:11), IRQVVQEVL (SEQ ID NO:12), VRSVVEEVV (SEQ ID NO:13) and ARDLLKQIL (SEQ ID NO:14) or a variant sequence thereof.

10. The genetically modified microorganism of claim 1, wherein said microorganism is a bacterium.

11. The genetically modified microorganism of claim 1, wherein said microorganism does not naturally comprise the genes necessary for the expression of BMCs and has not been genetically engineered to provide BMC production capability.

12. The genetically modified microorganism of claim 1, wherein said microorganism naturally comprises the genes necessary for the expression of BMCs but wherein said microorganism is a BMC null mutant.

13. The genetically modified microorganism of claim 12, wherein said microorganism comprises a mutation in the regulatory region of the BMC operon(s), preferably in the operon's promoter.

* * * * *

```
                         SEQUENCE LISTING

<160> NUMBER OF SEQ ID NOS: 79

<210> SEQ ID NO 1
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 1

Leu Glu Gln Ile Ile Arg Asp Val Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 2

Leu Glu Thr Leu Ile Arg Thr Ile Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 3

Leu Glu Thr Leu Ile Arg Asn Ile Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 4

Leu Arg Gln Ile Ile Glu Asp Val Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 5

Ile Glu Glu Ile Val Arg Ser Val Met
1               5

<210> SEQ ID NO 6
<211> LENGTH: 9
<212> TYPE: PRT
```

```
<213> ORGANISM: Artificial Sequence
<220> FEATURE:
<223> OTHER INFORMATION: Synthetic Sequence

<400> SEQUENCE: 6

Ile Glu Gln Val Val Lys Ala Val Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 7

Val Glu Lys Leu Val Arg Gln Ala Ile
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 8

Ile Gln Glu Ile Val Arg Thr Leu Ile
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 9

Val Glu Glu Ile Val Lys Arg Ile Met
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 10

Ile Glu Ser Met Val Arg Asp Val Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 11

Val Gln Asp Ile Ile Lys Asn Val Val
1               5

<210> SEQ ID NO 12
<211> LENGTH: 9
<212> TYPE: PRT
<213> ORGANISM: Artificial Sequence
```

```
<220> FEATURE:
<223> OTHER INFORMATION: Synthetic Sequence

<400> SEQUENCE: 12

Ile Arg Gln Val Val Gln Glu Val Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 13

Val Arg Ser Val Val Glu Glu Val Val
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 14

Ala Arg Asp Leu Leu Lys Gln Ile Leu
1               5

<210> SEQ ID NO 15
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(1)
<223> OTHER INFORMATION: /replace="Ile"
<220> FEATURE:
<221> NAME/KEY: VARIANT
<222> LOCATION: (2)..(2)
<223> OTHER INFORMATION: /replace="Tyr"
<220> FEATURE:
<221> NAME/KEY: VARIANT
<222> LOCATION: (4)..(4)
<223> OTHER INFORMATION: /replace="Lys"
<220> FEATURE:
<221> NAME/KEY: VARIANT
<222> LOCATION: (5)..(5)
<223> OTHER INFORMATION: /replace="Ala"
      /replace="Gly"
      /replace="Glu"
<220> FEATURE:
<221> NAME/KEY: VARIANT
<222> LOCATION: (6)..(6)
<223> OTHER INFORMATION: /replace="Ser"
      /replace="Gln"
<220> FEATURE:
<221> NAME/KEY: VARIANT
<222> LOCATION: (7)..(7)
<223> OTHER INFORMATION: /replace="Val"
      /replace="Leu"
      /replace="Phe"
<220> FEATURE:
<221> NAME/KEY: VARIANT
<222> LOCATION: (8)..(8)
<223> OTHER INFORMATION: /replace="Gln"
      /replace="Ser"
      /replace="Leu"
<220> FEATURE:
<221> NAME/KEY: VARIANT
<222> LOCATION: (9)..(9)
```

```
<223> OTHER INFORMATION: /replace="Gln"
      /replace="Arg"
<220> FEATURE:
<221> NAME/KEY: VARIANT
<222> LOCATION: (10)..(10)
<223> OTHER INFORMATION: /replace="Leu"
<220> FEATURE:
<221> NAME/KEY: VARIANT
<222> LOCATION: (11)..(11)
<223> OTHER INFORMATION: /replace="Met"
      /replace="Arg"
<220> FEATURE:
<221> NAME/KEY: VARIANT
<222> LOCATION: (12)..(12)
<223> OTHER INFORMATION: /replace="Leu"
      /replace="Cys"
      /replace="Gln"
<220> FEATURE:
<221> NAME/KEY: VARIANT
<222> LOCATION: (13)..(13)
<223> OTHER INFORMATION: /replace="Ser"
<220> FEATURE:
<221> NAME/KEY: VARIANT
<222> LOCATION: (14)..(14)
<223> OTHER INFORMATION: /replace="Met"
<220> FEATURE:
<221> NAME/KEY: VARIANT
<222> LOCATION: (17)..(17)
<223> OTHER INFORMATION: /replace="Asp"
      /replace="Glu"
<220> FEATURE:
<221> NAME/KEY: VARIANT
<222> LOCATION: (18)..(18)
<223> OTHER INFORMATION: /replace="Asn"
      /replace="Gln"

<400> SEQUENCE: 15

Val Val Gly Gln Val Tyr Ile Asn Lys Met Leu Val Thr Leu Phe Pro
1               5                   10                  15

His Arg

<210> SEQ ID NO 16
<211> LENGTH: 13
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(1)
<223> OTHER INFORMATION: /replace="Phe"
<220> FEATURE:
<221> NAME/KEY: VARIANT
<222> LOCATION: (2)..(2)
<223> OTHER INFORMATION: /replace="Pro"
      /replace="Ala"
<220> FEATURE:
<221> NAME/KEY: VARIANT
<222> LOCATION: (3)..(3)
<223> OTHER INFORMATION: /replace="Val"
<220> FEATURE:
<221> NAME/KEY: VARIANT
<222> LOCATION: (4)..(4)
<223> OTHER INFORMATION: /replace="Gln"
<220> FEATURE:
<221> NAME/KEY: VARIANT
<222> LOCATION: (6)..(6)
<223> OTHER INFORMATION: /replace="Ser"
      /replace="Gln"
      /replace="Trp"
<220> FEATURE:
<221> NAME/KEY: VARIANT
<222> LOCATION: (7)..(7)
<223> OTHER INFORMATION: /replace="Glu"
      /replace="Arg"
<220> FEATURE:
```

```
<221> NAME/KEY: VARIANT
<222> LOCATION: (11)..(11)
<223> OTHER INFORMATION: /replace="Gln"
<220> FEATURE:
<221> NAME/KEY: VARIANT
<222> LOCATION: (13)..(13)
<223> OTHER INFORMATION: /replace="Asn"

<400> SEQUENCE: 16

Leu Ser Pro Glu Gln Ala Gln Arg Ile Tyr Arg Gly Ser
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (2)..(2)
<223> OTHER INFORMATION: /replace="Asn"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (4)..(4)
<223> OTHER INFORMATION: /replace="Gln"
<220> FEATURE:
<221> NAME/KEY: VARIANT
<222> LOCATION: (5)..(5)
<223> OTHER INFORMATION: /replace="Glu"
<220> FEATURE:
<221> NAME/KEY: VARIANT
<222> LOCATION: (6)..(6)
<223> OTHER INFORMATION: /replace="Ile"
<220> FEATURE:
<221> NAME/KEY: VARIANT
<222> LOCATION: (7)..(7)
<223> OTHER INFORMATION: /replace="Arg"
      /replace="Glu"
<220> FEATURE:
<221> NAME/KEY: VARIANT
<222> LOCATION: (8)..(8)
<223> OTHER INFORMATION: /replace="Asp"
<220> FEATURE:
<221> NAME/KEY: VARIANT
<222> LOCATION: (9)..(9)
<223> OTHER INFORMATION: /replace="Met"
<220> FEATURE:
<221> NAME/KEY: VARIANT
<222> LOCATION: (10)..(10)
<223> OTHER INFORMATION: /replace="Ile"
<220> FEATURE:
<221> NAME/KEY: VARIANT
<222> LOCATION: (11)..(11)
<223> OTHER INFORMATION: /replace="Glu"
<220> FEATURE:
<221> NAME/KEY: VARIANT
<222> LOCATION: (12)..(12)
<223> OTHER INFORMATION: /replace="Gln"
<220> FEATURE:
<221> NAME/KEY: VARIANT
<222> LOCATION: (13)..(13)
<223> OTHER INFORMATION: /replace="Ile"
<220> FEATURE:
<221> NAME/KEY: VARIANT
<222> LOCATION: (14)..(14)
<223> OTHER INFORMATION: /replace="Met"
<220> FEATURE:
<221> NAME/KEY: VARIANT
<222> LOCATION: (16)..(16)
<223> OTHER INFORMATION: /replace="Gln"
      /replace="Ser"
```

```
<400> SEQUENCE: 17

Met Asp Glu Lys Gln Leu Lys Glu Ile Val Arg Ser Val Leu Ala Glu
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(1)
<223> OTHER INFORMATION: /replace="Lys"
      /replace="Ser"
<220> FEATURE:
<221> NAME/KEY: VARIANT
<222> LOCATION: (2)..(2)
<223> OTHER INFORMATION: /replace="Asp"
<220> FEATURE:
<221> NAME/KEY: VARIANT
<222> LOCATION: (3)..(3)
<223> OTHER INFORMATION: /replace="Glu"
<220> FEATURE:
<221> NAME/KEY: VARIANT
<222> LOCATION: (5)..(5)
<223> OTHER INFORMATION: /replace="Val"
<220> FEATURE:
<221> NAME/KEY: VARIANT
<222> LOCATION: (6)..(6)
<223> OTHER INFORMATION: /replace="Asp"
      /replace="Asn"
<220> FEATURE:
<221> NAME/KEY: VARIANT
<222> LOCATION: (7)..(7)
<223> OTHER INFORMATION: /replace="glu"
      /replace="Ser"
<220> FEATURE:
<221> NAME/KEY: VARIANT
<222> LOCATION: (8)..(8)
<223> OTHER INFORMATION: /replace="Leu"
<220> FEATURE:
<221> NAME/KEY: VARIANT
<222> LOCATION: (9)..(9)
<223> OTHER INFORMATION: /replace="Ile"
<220> FEATURE:
<221> NAME/KEY: VARIANT
<222> LOCATION: (10)..(10)
<223> OTHER INFORMATION: /replace="Lys"
      /replace="Glu"
      /replace="Gln"
<220> FEATURE:
<221> NAME/KEY: VARIANT
<222> LOCATION: (11)..(11)
<223> OTHER INFORMATION: /replace="Arg"
<220> FEATURE:
<221> NAME/KEY: VARIANT
<222> LOCATION: (14)..(14)
<223> OTHER INFORMATION: /replace="Ala"
<220> FEATURE:
<221> NAME/KEY: VARIANT
<222> LOCATION: (15)..(15)
<223> OTHER INFORMATION: /replace="Lys"

<400> SEQUENCE: 18

Ala Glu Ala Leu Ile Glu Leu Ile Val Arg Lys Val Leu Glu Glu Leu
1               5                   10                  15

<210> SEQ ID NO 19
<211> LENGTH: 18
<212> TYPE: PRT
<213> ORGANISM: Artificial Sequence
<220> FEATURE:
<223> OTHER INFORMATION: Synthetic Sequence
<220> FEATURE:
```

```
<221> NAME/KEY: VARIANT
<222> LOCATION: (4)..(4)
<223> OTHER INFORMATION: /replace="Asp"
       /replace="Thr"
<220> FEATURE:
<221> NAME/KEY: VARIANT
<222> LOCATION: (6)..(6)
<223> OTHER INFORMATION: /replace="Glu"
<220> FEATURE:
<221> NAME/KEY: VARIANT
<222> LOCATION: (7)..(7)
<223> OTHER INFORMATION: /replace="Val"
<220> FEATURE:
<221> NAME/KEY: VARIANT
<222> LOCATION: (8)..(8)
<223> OTHER INFORMATION: /replace="Val"
<220> FEATURE:
<221> NAME/KEY: VARIANT
<222> LOCATION: (9)..(9)
<223> OTHER INFORMATION: /replace="Glu"
<220> FEATURE:
<221> NAME/KEY: VARIANT
<222> LOCATION: (11)..(11)
<223> OTHER INFORMATION: /replace="Val"
<220> FEATURE:
<221> NAME/KEY: VARIANT
<222> LOCATION: (12)..(12)
<223> OTHER INFORMATION: /replace="Val"
<220> FEATURE:
<221> NAME/KEY: VARIANT
<222> LOCATION: (13)..(13)
<223> OTHER INFORMATION: /replace="Lys"
       /replace="Ala"
<220> FEATURE:
<221> NAME/KEY: VARIANT
<222> LOCATION: (14)..(14)
<223> OTHER INFORMATION: /replace="Glu"
<220> FEATURE:
<221> NAME/KEY: VARIANT
<222> LOCATION: (17)..(17)
<223> OTHER INFORMATION: /replace="Ser"
       /replace="Arg"
       /replace="Ala"
<220> FEATURE:
<221> NAME/KEY: VARIANT
<222> LOCATION: (18)..(18)
<223> OTHER INFORMATION: /replace="Asp"

<400> SEQUENCE: 19

Met Glu Ile Asn Glu Lys Leu Leu Arg Gln Ile Ile Glu Asp Val Leu
1               5                   10                  15

Lys Glu

<210> SEQ ID NO 20
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(1)
<223> OTHER INFORMATION: /replace="Ile"
<220> FEATURE:
<221> NAME/KEY: VARIANT
<222> LOCATION: (2)..(2)
<223> OTHER INFORMATION: /replace="Asp"
<220> FEATURE:
<221> NAME/KEY: VARIANT
<222> LOCATION: (3)..(3)
<223> OTHER INFORMATION: /replace="Glu"
<220> FEATURE:
<221> NAME/KEY: VARIANT
<222> LOCATION: (4)..(4)
<223> OTHER INFORMATION: /replace="Lys"
<220> FEATURE:
```

```
<221> NAME/KEY: VARIANT
<222> LOCATION: (5)..(5)
<223> OTHER INFORMATION: /replace="Leu"
<220> FEATURE:
<221> NAME/KEY: VARIANT
<222> LOCATION: (6)..(6)
<223> OTHER INFORMATION: /replace="Leu"
<220> FEATURE:
<221> NAME/KEY: VARIANT
<222> LOCATION: (8)..(8)
<223> OTHER INFORMATION: /replace="Glu"
<220> FEATURE:
<221> NAME/KEY: VARIANT
<222> LOCATION: (9)..(9)
<223> OTHER INFORMATION: /replace="Ile"
<220> FEATURE:
<221> NAME/KEY: VARIANT
<222> LOCATION: (11)..(11)
<223> OTHER INFORMATION: /replace="Lys"
<220> FEATURE:
<221> NAME/KEY: VARIANT
<222> LOCATION: (12)..(12)
<223> OTHER INFORMATION: /replace="Glu"
      /replace="Gln"
<220> FEATURE:
<221> NAME/KEY: VARIANT
<222> LOCATION: (15)..(15)
<223> OTHER INFORMATION: /replace="Asn"
<220> FEATURE:
<221> NAME/KEY: VARIANT
<222> LOCATION: (16)..(16)
<223> OTHER INFORMATION: /replace="Leu"
<220> FEATURE:
<221> NAME/KEY: VARIANT
<222> LOCATION: (17)..(17)
<223> OTHER INFORMATION: /replace="Glu"
      /replace="Gly"

<400> SEQUENCE: 20

Met Asn Thr Asp Ala Ile Glu Ser Met Val Arg Asp Val Leu Ser Met
1               5                   10                  15

Asn Ser

<210> SEQ ID NO 21
<211> LENGTH: 16
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (2)..(2)
<223> OTHER INFORMATION: /replace="Asp"
      /replace="Glu"
<220> FEATURE:
<221> NAME/KEY: VARIANT
<222> LOCATION: (3)..(3)
<223> OTHER INFORMATION: /replace="Ser"
      /replace="Glu"
<220> FEATURE:
<221> NAME/KEY: VARIANT
<222> LOCATION: (4)..(4)
<223> OTHER INFORMATION: /replace="Leu"
<220> FEATURE:
<221> NAME/KEY: VARIANT
<222> LOCATION: (6)..(6)
<223> OTHER INFORMATION: /replace="Val"
<220> FEATURE:
<221> NAME/KEY: VARIANT
<222> LOCATION: (8)..(8)
<223> OTHER INFORMATION: /replace="Gln"
      /replace="Lys"
      /replace="Asp"
<220> FEATURE:
<221> NAME/KEY: VARIANT
<222> LOCATION: (9)..(9)
```

```
<223> OTHER INFORMATION: /replace="Ile"
<220> FEATURE:
<221> NAME/KEY: VARIANT
<222> LOCATION: (10)..(10)
<223> OTHER INFORMATION: /replace="Val"
<220> FEATURE:
<221> NAME/KEY: VARIANT
<222> LOCATION: (11)..(11)
<223> OTHER INFORMATION: /replace="Lys"
<220> FEATURE:
<221> NAME/KEY: VARIANT
<222> LOCATION: (12)..(12)
<223> OTHER INFORMATION: /replace="Asn"
      /replace="Lys"
<220> FEATURE:
<221> NAME/KEY: VARIANT
<222> LOCATION: (13)..(13)
<223> OTHER INFORMATION: /replace="Val"
<220> FEATURE:
<221> NAME/KEY: VARIANT
<222> LOCATION: (14)..(14)
<223> OTHER INFORMATION: /replace="Ile"
<220> FEATURE:
<221> NAME/KEY: VARIANT
<222> LOCATION: (15)..(15)
<223> OTHER INFORMATION: /replace="Leu"
      /replace="Arg"
      /replace="Asn"

<400> SEQUENCE: 21

Met Asn Thr Ser Glu Leu Glu Thr Leu Ile Arg Thr Ile Leu Ser Glu
1               5                   10                  15

<210> SEQ ID NO 22
<211> LENGTH: 26
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(1)
<223> OTHER INFORMATION: /replace="Pro"
<220> FEATURE:
<221> NAME/KEY: VARIANT
<222> LOCATION: (2)..(2)
<223> OTHER INFORMATION: /replace="Gly"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (4)..(4)
<223> OTHER INFORMATION: /replace="Asp"
<220> FEATURE:
<221> NAME/KEY: VARIANT
<222> LOCATION: (5)..(5)
<223> OTHER INFORMATION: /replace="Ala"
<220> FEATURE:
<221> NAME/KEY: VARIANT
<222> LOCATION: (6)..(6)
<223> OTHER INFORMATION: /replace="Asn"
<220> FEATURE:
<221> NAME/KEY: VARIANT
<222> LOCATION: (8)..(8)
<223> OTHER INFORMATION: /replace="Gln"
<220> FEATURE:
<221> NAME/KEY: VARIANT
<222> LOCATION: (9)..(9)
<223> OTHER INFORMATION: /replace="Gln"
<220> FEATURE:
<221> NAME/KEY: VARIANT
<222> LOCATION: (10)..(10)
<223> OTHER INFORMATION: /replace="Val"
<220> FEATURE:
<221> NAME/KEY: VARIANT
```

```
<222> LOCATION: (12)..(12)
<223> OTHER INFORMATION: /replace="Glu"
<220> FEATURE:
<221> NAME/KEY: VARIANT
<222> LOCATION: (16)..(16)
<223> OTHER INFORMATION: /replace="Arg"
<220> FEATURE:
<221> NAME/KEY: VARIANT
<222> LOCATION: (17)..(17)
<223> OTHER INFORMATION: /replace="Ile"
<220> FEATURE:
<221> NAME/KEY: VARIANT
<222> LOCATION: (18)..(18)
<223> OTHER INFORMATION: /replace="Ile"
<220> FEATURE:
<221> NAME/KEY: VARIANT
<222> LOCATION: (19)..(19)
<223> OTHER INFORMATION: /replace="Gly"
<220> FEATURE:
<221> NAME/KEY: VARIANT
<222> LOCATION: (20)..(20)
<223> OTHER INFORMATION: /replace="Glu"
      /replace="Ser"
<220> FEATURE:
<221> NAME/KEY: VARIANT
<222> LOCATION: (21)..(21)
<223> OTHER INFORMATION: /replace="Ser"
<220> FEATURE:
<221> NAME/KEY: VARIANT
<222> LOCATION: (23)..(23)
<223> OTHER INFORMATION: /replace="Ser"
<220> FEATURE:
<221> NAME/KEY: VARIANT
<222> LOCATION: (26)..(26)
<223> OTHER INFORMATION: /replace="Val"

<400> SEQUENCE: 22

Ala Lys Ser Ser Leu Thr Glu Glu Asp Ile Tyr Asp Ala Val Lys Lys
1               5                   10                  15

Val Leu Glu Gln His Gly Ala Leu Asp Pro
            20                  25

<210> SEQ ID NO 23
<211> LENGTH: 19
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (3)..(3)
<223> OTHER INFORMATION: /replace="Thr"
<220> FEATURE:
<221> NAME/KEY: VARIANT
<222> LOCATION: (4)..(4)
<223> OTHER INFORMATION: /replace="Thr"
<220> FEATURE:
<221> NAME/KEY: VARIANT
<222> LOCATION: (5)..(5)
<223> OTHER INFORMATION: /replace="Gln"
<220> FEATURE:
<221> NAME/KEY: VARIANT
<222> LOCATION: (6)..(6)
<223> OTHER INFORMATION: /replace="Leu"
<220> FEATURE:
<221> NAME/KEY: VARIANT
<222> LOCATION: (7)..(7)
<223> OTHER INFORMATION: /replace="Glu"
<220> FEATURE:
<221> NAME/KEY: VARIANT
<222> LOCATION: (8)..(8)
<223> OTHER INFORMATION: /replace="Asn"
<220> FEATURE:
<221> NAME/KEY: VARIANT
<222> LOCATION: (9)..(9)
<223> OTHER INFORMATION: /replace="Met"
```

```
<220> FEATURE:
<221> NAME/KEY: VARIANT
<222> LOCATION: (10)..(10)
<223> OTHER INFORMATION: /replace="Ile"
<220> FEATURE:
<221> NAME/KEY: VARIANT
<222> LOCATION: (11)..(11)
<223> OTHER INFORMATION: /replace="Arg"
      /replace="Ala"
<220> FEATURE:
<221> NAME/KEY: VARIANT
<222> LOCATION: (12)..(12)
<223> OTHER INFORMATION: /replace="Lys"
      /replace="Asn"
<220> FEATURE:
<221> NAME/KEY: VARIANT
<222> LOCATION: (15)..(15)
<223> OTHER INFORMATION: /replace="Ala"
      /replace="Glu"
      /replace="Arg"
<220> FEATURE:
<221> NAME/KEY: VARIANT
<222> LOCATION: (16)..(16)
<223> OTHER INFORMATION: /replace="Lys"
<220> FEATURE:
<221> NAME/KEY: VARIANT
<222> LOCATION: (17)..(17)
<223> OTHER INFORMATION: /replace="Phe"
      /replace="Tyr"
<220> FEATURE:
<221> NAME/KEY: VARIANT
<222> LOCATION: (18)..(18)
<223> OTHER INFORMATION: /replace="Leu"
      /replace="Gly"

<400> SEQUENCE: 23

Met Asn Asp Ile Glu Ile Ala Gln Ala Val Ser Thr Ile Leu Ser Asp
1               5                   10                  15

Asn Thr Lys

<210> SEQ ID NO 24
<211> LENGTH: 21
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (3)..(3)
<223> OTHER INFORMATION: /replace="Glu"
<220> FEATURE:
<221> NAME/KEY: VARIANT
<222> LOCATION: (6)..(6)
<223> OTHER INFORMATION: /replace="Val"
<220> FEATURE:
<221> NAME/KEY: VARIANT
<222> LOCATION: (7)..(7)
<223> OTHER INFORMATION: /replace="Gly"
<220> FEATURE:
<221> NAME/KEY: VARIANT
<222> LOCATION: (9)..(9)
<223> OTHER INFORMATION: /replace="Ile"
<220> FEATURE:
<221> NAME/KEY: VARIANT
<222> LOCATION: (10)..(10)
<223> OTHER INFORMATION: /replace="Ala"
<220> FEATURE:
<221> NAME/KEY: VARIANT
<222> LOCATION: (12)..(12)
<223> OTHER INFORMATION: /replace="Gln"
<220> FEATURE:
<221> NAME/KEY: VARIANT
<222> LOCATION: (14)..(14)
<223> OTHER INFORMATION: /replace="Leu"
<220> FEATURE:
<221> NAME/KEY: VARIANT
```

```
<222> LOCATION: (16)..(16)
<223> OTHER INFORMATION: /replace="Gly"
<220> FEATURE:
<221> NAME/KEY: VARIANT
<222> LOCATION: (17)..(17)
<223> OTHER INFORMATION: /replace="Met"
<220> FEATURE:
<221> NAME/KEY: VARIANT
<222> LOCATION: (18)..(18)
<223> OTHER INFORMATION: /replace="Gln"
<220> FEATURE:
<221> NAME/KEY: VARIANT
<222> LOCATION: (19)..(19)
<223> OTHER INFORMATION: /replace="Asp"

<400> SEQUENCE: 24

Leu Asp Ala Glu Ser Ala Ala Asp Met Thr Glu Met Ile Ala Lys Glu
1               5                   10                  15

Leu Lys Glu Ala Gly
            20

<210> SEQ ID NO 25
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(1)
<223> OTHER INFORMATION: /replace="Pro"
<220> FEATURE:
<221> NAME/KEY: VARIANT
<222> LOCATION: (2)..(2)
<223> OTHER INFORMATION: /replace="Asn"
<220> FEATURE:
<221> NAME/KEY: VARIANT
<222> LOCATION: (3)..(3)
<223> OTHER INFORMATION: /replace="Glu"
<220> FEATURE:
<221> NAME/KEY: VARIANT
<222> LOCATION: (4)..(4)
<223> OTHER INFORMATION: /replace="Glu"
      /replace="Ala"
<220> FEATURE:
<221> NAME/KEY: VARIANT
<222> LOCATION: (6)..(6)
<223> OTHER INFORMATION: /replace="Ile"
<220> FEATURE:
<221> NAME/KEY: VARIANT
<222> LOCATION: (8)..(8)
<223> OTHER INFORMATION: /replace="Ala"
      /replace="Ser"
<220> FEATURE:
<221> NAME/KEY: VARIANT
<222> LOCATION: (11)..(11)
<223> OTHER INFORMATION: /replace="Arg"
<220> FEATURE:
<221> NAME/KEY: VARIANT
<222> LOCATION: (12)..(12)
<223> OTHER INFORMATION: /replace="Arg"
      /replace="Gln"
<220> FEATURE:
<221> NAME/KEY: VARIANT
<222> LOCATION: (14)..(14)
<223> OTHER INFORMATION: /replace="Leu"
<220> FEATURE:
<221> NAME/KEY: VARIANT
<222> LOCATION: (15)..(15)
<223> OTHER INFORMATION: /replace="Glu"
<220> FEATURE:
<221> NAME/KEY: VARIANT
<222> LOCATION: (18)..(18)
<223> OTHER INFORMATION: /replace="Lys"

<400> SEQUENCE: 25
```

```
Asp Asp Ala Asp Leu Val Ala Glu Ile Thr Lys Lys Val Met Ala Gln
1               5                   10                  15

Leu Gly

<210> SEQ ID NO 26
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (5)..(5)
<223> OTHER INFORMATION: /replace="Met"
<220> FEATURE:
<221> NAME/KEY: VARIANT
<222> LOCATION: (11)..(11)
<223> OTHER INFORMATION: /replace="Arg"
      /replace="Lys"
<220> FEATURE:
<221> NAME/KEY: VARIANT
<222> LOCATION: (16)..(16)
<223> OTHER INFORMATION: /replace="Arg"
<220> FEATURE:
<221> NAME/KEY: VARIANT
<222> LOCATION: (20)..(20)
<223> OTHER INFORMATION: /replace="Thr"

<400> SEQUENCE: 26

Val Asn Glu Gln Leu Val Gln Asp Ile Val Gln Glu Val Val Ala Lys
1               5                   10                  15

Met Gln Ile Ser
            20

<210> SEQ ID NO 27
<211> LENGTH: 19
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (4)..(4)
<223> OTHER INFORMATION: /replace="Gln"
<220> FEATURE:
<221> NAME/KEY: VARIANT
<222> LOCATION: (7)..(7)
<223> OTHER INFORMATION: /replace="Gln"
<220> FEATURE:
<221> NAME/KEY: VARIANT
<222> LOCATION: (8)..(8)
<223> OTHER INFORMATION: /replace="Leu"
<220> FEATURE:
<221> NAME/KEY: VARIANT
<222> LOCATION: (11)..(11)
<223> OTHER INFORMATION: /replace="Glu"
<220> FEATURE:
<221> NAME/KEY: VARIANT
<222> LOCATION: (12)..(12)
<223> OTHER INFORMATION: /replace="Arg"
      /replace="Glu"
<220> FEATURE:
<221> NAME/KEY: VARIANT
<222> LOCATION: (16)..(16)
<223> OTHER INFORMATION: /replace="Glu"
<220> FEATURE:
<221> NAME/KEY: VARIANT
<222> LOCATION: (18)..(18)
<223> OTHER INFORMATION: /replace="Ser"

<400> SEQUENCE: 27

Asp Gln Glu Ala Leu Val Lys Ala Ile Thr Asp Gln Val Met Ala Ala
```

Leu Lys Lys

<210> SEQ ID NO 28
<211> LENGTH: 20
<212> TYPE: PRT
<213> ORGANISM: Artificial Sequence
<220> FEATURE:
<223> OTHER INFORMATION: Artificial Sequence
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (4)..(4)
<223> OTHER INFORMATION: /replace="Thr"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: VARIANT
<222> LOCATION: (13)..(13)
<223> OTHER INFORMATION: /replace="Gln"
<220> FEATURE:
<221> NAME/KEY: VARIANT
<222> LOCATION: (14)..(14)
<223> OTHER INFORMATION: /replace="Glu"
<220> FEATURE:
<221> NAME/KEY: VARIANT
<222> LOCATION: (17)..(17)
<223> OTHER INFORMATION: /replace="Ser"
<220> FEATURE:
<221> NAME/KEY: VARIANT
<222> LOCATION: (18)..(18)
<223> OTHER INFORMATION: /replace="Gln"
<220> FEATURE:
<221> NAME/KEY: VARIANT
<222> LOCATION: (19)..(19)
<223> OTHER INFORMATION: /replace="Leu"
<220> FEATURE:
<221> NAME/KEY: VARIANT
<222> LOCATION: (20)..(20)
<223> OTHER INFORMATION: /replace="Asn"

<400> SEQUENCE: 28

Met Gln Ile Asp Glu Glu Leu Ile Arg Ser Val Val Ala Gln Val Leu
1               5                   10                  15

Ala Glu Val Gly
            20

<210> SEQ ID NO 29
<211> LENGTH: 15
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(1)
<223> OTHER INFORMATION: /replace="Gln"
      /replace="Asp"
<220> FEATURE:
<221> NAME/KEY: VARIANT
<222> LOCATION: (2)..(2)
<223> OTHER INFORMATION: /replace="Glu"
      /replace="Asp"
<220> FEATURE:
<221> NAME/KEY: VARIANT
<222> LOCATION: (3)..(3)
<223> OTHER INFORMATION: /replace="Ile"
      /replace="Leu"
<220> FEATURE:

```
<221> NAME/KEY: VARIANT
<222> LOCATION: (4)..(4)
<223> OTHER INFORMATION: /replace="Gln"
      /replace="Ala"
<220> FEATURE:
<221> NAME/KEY: VARIANT
<222> LOCATION: (5)..(5)
<223> OTHER INFORMATION: /replace="Gln"
      /replace="Asp"
<220> FEATURE:
<221> NAME/KEY: VARIANT
<222> LOCATION: (6)..(6)
<223> OTHER INFORMATION: /replace="Leu"
      /replace="Val"
<220> FEATURE:
<221> NAME/KEY: VARIANT
<222> LOCATION: (7)..(7)
<223> OTHER INFORMATION: /replace="Leu"
      /replace="Val"
<220> FEATURE:
<221> NAME/KEY: VARIANT
<222> LOCATION: (8)..(8)
<223> OTHER INFORMATION: /replace="Arg"
      /replace="Asn"
<220> FEATURE:
<221> NAME/KEY: VARIANT
<222> LOCATION: (9)..(9)
<223> OTHER INFORMATION: /replace="Gln"
      /replace="Lys"
<220> FEATURE:
<221> NAME/KEY: VARIANT
<222> LOCATION: (10)..(10)
<223> OTHER INFORMATION: /replace="Ile"
      /replace="Leu"
<220> FEATURE:
<221> NAME/KEY: VARIANT
<222> LOCATION: (11)..(11)
<223> OTHER INFORMATION: /replace="Ile"
      /replace="Val"
<220> FEATURE:
<221> NAME/KEY: VARIANT
<222> LOCATION: (12)..(12)
<223> OTHER INFORMATION: /replace="Gln"
      /replace="Gly"
<220> FEATURE:
<221> NAME/KEY: VARIANT
<222> LOCATION: (13)..(13)
<223> OTHER INFORMATION: /replace="Arg"
      /replace="Ala"
<220> FEATURE:
<221> NAME/KEY: VARIANT
<222> LOCATION: (14)..(14)
<223> OTHER INFORMATION: /replace="Met"
<220> FEATURE:
<221> NAME/KEY: VARIANT
<222> LOCATION: (15)..(15)
<223> OTHER INFORMATION: /replace="Gly"
      /replace="Ser"

<400> SEQUENCE: 29

Glu Asn Val Glu Arg Ile Ile Lys Glu Val Leu Glu Gln Leu Lys
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (2)..(2)
<223> OTHER INFORMATION: /replace="Asp"
<220> FEATURE:
<221> NAME/KEY: VARIANT
<222> LOCATION: (3)..(3)
<223> OTHER INFORMATION: /replace="Ile"
```

```
      /replace="Asn"
      /replace="Leu"
<220> FEATURE:
<221> NAME/KEY: VARIANT
<222> LOCATION: (4)..(4)
<223> OTHER INFORMATION: /replace="Tyr"
<220> FEATURE:
<221> NAME/KEY: VARIANT
<222> LOCATION: (5)..(5)
<223> OTHER INFORMATION: /replace="Asn"
      /replace="Ser"
      /replace="Leu"
      /replace="Phe"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (7)..(7)
<223> OTHER INFORMATION: /replace="Asn"
<220> FEATURE:
<221> NAME/KEY: VARIANT
<222> LOCATION: (8)..(8)
<223> OTHER INFORMATION: /replace="Lys"
<220> FEATURE:
<221> NAME/KEY: VARIANT
<222> LOCATION: (9)..(9)
<223> OTHER INFORMATION: /replace="Leu"
      /replace="Phe"
<220> FEATURE:
<221> NAME/KEY: VARIANT
<222> LOCATION: (10)..(10)
<223> OTHER INFORMATION: /replace="Ala"
<220> FEATURE:
<221> NAME/KEY: VARIANT
<222> LOCATION: (11)..(11)
<223> OTHER INFORMATION: /replace="Val"
      /replace="Met"
<220> FEATURE:
<221> NAME/KEY: VARIANT
<222> LOCATION: (12)..(12)
<223> OTHER INFORMATION: /replace="Ala"
<220> FEATURE:
<221> NAME/KEY: VARIANT
<222> LOCATION: (13)..(13)
<223> OTHER INFORMATION: /replace="Thr"
<220> FEATURE:
<221> NAME/KEY: VARIANT
<222> LOCATION: (14)..(14)
<223> OTHER INFORMATION: /replace="Lys"
<220> FEATURE:
<221> NAME/KEY: VARIANT
<222> LOCATION: (15)..(15)
<223> OTHER INFORMATION: /replace="Asn"
<220> FEATURE:
<221> NAME/KEY: VARIANT
<222> LOCATION: (16)..(16)
<223> OTHER INFORMATION: /replace="Met"

<400> SEQUENCE: 30

Met Ala Lys Arg Glu Thr Pro Arg Val Lys Glu Leu Ala Glu Arg Leu
1               5                   10                  15

<210> SEQ ID NO 31
<211> LENGTH: 22
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (2)..(2)
<223> OTHER INFORMATION: /replace="Asp"
      /replace="Gly"
<220> FEATURE:
<221> NAME/KEY: VARIANT
```

```
<222> LOCATION: (5)..(5)
<223> OTHER INFORMATION: /replace="Gle"
      /replace="Asp"
<220> FEATURE:
<221> NAME/KEY: VARIANT
<222> LOCATION: (10)..(10)
<223> OTHER INFORMATION: /replace="Arg"
<220> FEATURE:
<221> NAME/KEY: VARIANT
<222> LOCATION: (12)..(12)
<223> OTHER INFORMATION: /replace="Ile"
<220> FEATURE:
<221> NAME/KEY: VARIANT
<222> LOCATION: (13)..(13)
<223> OTHER INFORMATION: /replace="Ala"
<220> FEATURE:
<221> NAME/KEY: VARIANT
<222> LOCATION: (17)..(17)
<223> OTHER INFORMATION: /replace="Arg"
<220> FEATURE:
<221> NAME/KEY: VARIANT
<222> LOCATION: (18)..(18)
<223> OTHER INFORMATION: /replace="Glu"
<220> FEATURE:
<221> NAME/KEY: VARIANT
<222> LOCATION: (20)..(20)
<223> OTHER INFORMATION: /replace="Asn"
      /replace="Gly"
<220> FEATURE:
<221> NAME/KEY: VARIANT
<222> LOCATION: (21)..(21)
<223> OTHER INFORMATION: /replace="Arg"
<220> FEATURE:
<221> NAME/KEY: VARIANT
<222> LOCATION: (22)..(22)
<223> OTHER INFORMATION: /replace="Gln"

<400> SEQUENCE: 31

Ile Glu Ala Leu Arg Ala Glu Leu Arg Ala Leu Val Val Glu Glu Leu
1               5                   10                  15

Ala Gln Leu Ile Lys Arg
            20

<210> SEQ ID NO 32
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(1)
<223> OTHER INFORMATION: /replace="Ile"
<220> FEATURE:
<221> NAME/KEY: VARIANT
<222> LOCATION: (2)..(2)
<223> OTHER INFORMATION: /replace="Tyr"
<220> FEATURE:
<221> NAME/KEY: VARIANT
<222> LOCATION: (4)..(4)
<223> OTHER INFORMATION: /replace="Lys"
<220> FEATURE:
<221> NAME/KEY: VARIANT
<222> LOCATION: (5)..(5)
<223> OTHER INFORMATION: /replace="Ala"
      /replace="Gly"
      /replace="Glu"
<220> FEATURE:
<221> NAME/KEY: VARIANT
<222> LOCATION: (6)..(6)
<223> OTHER INFORMATION: /replace="Ser"
      /replace="Gln"
<220> FEATURE:
<221> NAME/KEY: VARIANT
<222> LOCATION: (7)..(7)
<223> OTHER INFORMATION: /replace="Val"
```

```
      /replace="Leu"
      /replace="Phe"
<220> FEATURE:
<221> NAME/KEY: VARIANT
<222> LOCATION: (8)..(8)
<223> OTHER INFORMATION: /replace="Gln"
      /replace="Ser"
<220> FEATURE:
<221> NAME/KEY: VARIANT
<222> LOCATION: (9)..(9)
<223> OTHER INFORMATION: /replace="Gln"
      /replace="Arg"
<220> FEATURE:
<221> NAME/KEY: VARIANT
<222> LOCATION: (10)..(10)
<223> OTHER INFORMATION: /replace="Leu"
<220> FEATURE:
<221> NAME/KEY: VARIANT
<222> LOCATION: (11)..(11)
<223> OTHER INFORMATION: /replace="Met"
<220> FEATURE:
<221> NAME/KEY: VARIANT
<222> LOCATION: (12)..(12)
<223> OTHER INFORMATION: /replace="Gln"
<220> FEATURE:
<221> NAME/KEY: VARIANT
<222> LOCATION: (13)..(13)
<223> OTHER INFORMATION: /replace="Ser"
<220> FEATURE:
<221> NAME/KEY: VARIANT
<222> LOCATION: (14)..(14)
<223> OTHER INFORMATION: /replace="Met"
<220> FEATURE:
<221> NAME/KEY: VARIANT
<222> LOCATION: (17)..(17)
<223> OTHER INFORMATION: /replace="Asp"
      /replace="Glu"
<220> FEATURE:
<221> NAME/KEY: VARIANT
<222> LOCATION: (18)..(18)
<223> OTHER INFORMATION: /replace="Asn"
      /replace="Gln"

<400> SEQUENCE: 32

Val Val Gly Gln Val Tyr Ile Asn Lys Met Leu Cys Thr Leu Phe Pro
1               5                   10                  15

His Arg

<210> SEQ ID NO 33
<211> LENGTH: 16
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(1)
<223> OTHER INFORMATION: /replace="Lys"
      /replace="Ser"
<220> FEATURE:
<221> NAME/KEY: VARIANT
<222> LOCATION: (2)..(2)
<223> OTHER INFORMATION: /replace="Asp"
<220> FEATURE:
<221> NAME/KEY: VARIANT
<222> LOCATION: (3)..(3)
<223> OTHER INFORMATION: /replace="Glu"
<220> FEATURE:
<221> NAME/KEY: VARIANT
<222> LOCATION: (5)..(5)
<223> OTHER INFORMATION: /replace="Val"
<220> FEATURE:
<221> NAME/KEY: VARIANT
<222> LOCATION: (6)..(6)
<223> OTHER INFORMATION: /replace="Asp"
      /replace="Asn"
```

```
<220> FEATURE:
<221> NAME/KEY: VARIANT
<222> LOCATION: (7)..(7)
<223> OTHER INFORMATION: /replace="Ser"
<220> FEATURE:
<221> NAME/KEY: VARIANT
<222> LOCATION: (8)..(8)
<223> OTHER INFORMATION: /replace="Leu"
<220> FEATURE:
<221> NAME/KEY: VARIANT
<222> LOCATION: (9)..(9)
<223> OTHER INFORMATION: /replace="Ile"
<220> FEATURE:
<221> NAME/KEY: VARIANT
<222> LOCATION: (10)..(10)
<223> OTHER INFORMATION: /replace="Lys"
     /replace="Glu"
     /replace="Gln"
<220> FEATURE:
<221> NAME/KEY: VARIANT
<222> LOCATION: (11)..(11)
<223> OTHER INFORMATION: /replace="Arg"
<220> FEATURE:
<221> NAME/KEY: VARIANT
<222> LOCATION: (14)..(14)
<223> OTHER INFORMATION: /replace="Ala"
<220> FEATURE:
<221> NAME/KEY: VARIANT
<222> LOCATION: (15)..(15)
<223> OTHER INFORMATION: /replace="Lys"

<400> SEQUENCE: 33

Ala Glu Ala Leu Ile Glu Glu Ile Val Arg Lys Val Leu Glu Glu Leu
1               5                   10                  15

<210> SEQ ID NO 34
<211> LENGTH: 19
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (3)..(3)
<223> OTHER INFORMATION: /replace="Asp"
     /replace="Thr"
<220> FEATURE:
<221> NAME/KEY: VARIANT
<222> LOCATION: (6)..(6)
<223> OTHER INFORMATION: /replace="Glu"
<220> FEATURE:
<221> NAME/KEY: VARIANT
<222> LOCATION: (7)..(7)
<223> OTHER INFORMATION: /replace="Val"
<220> FEATURE:
<221> NAME/KEY: VARIANT
<222> LOCATION: (8)..(8)
<223> OTHER INFORMATION: /replace="Val"
<220> FEATURE:
<221> NAME/KEY: VARIANT
<222> LOCATION: (9)..(9)
<223> OTHER INFORMATION: /replace="Glu"
<220> FEATURE:
<221> NAME/KEY: VARIANT
<222> LOCATION: (11)..(11)
<223> OTHER INFORMATION: /replace="Val"
<220> FEATURE:
<221> NAME/KEY: VARIANT
<222> LOCATION: (12)..(12)
<223> OTHER INFORMATION: /replace="Val"
<220> FEATURE:
<221> NAME/KEY: VARIANT
<222> LOCATION: (13)..(13)
<223> OTHER INFORMATION: /replace="Lys"
<220> FEATURE:
<221> NAME/KEY: VARIANT
<222> LOCATION: (14)..(14)
```

```
<223> OTHER INFORMATION: /replace="Glu"
<220> FEATURE:
<221> NAME/KEY: VARIANT
<222> LOCATION: (17)..(17)
<223> OTHER INFORMATION: /replace="Ser"
      /replace="Arg"
      /replace="Ala"
<220> FEATURE:
<221> NAME/KEY: VARIANT
<222> LOCATION: (18)..(18)
<223> OTHER INFORMATION: /replace="Asp"
<220> FEATURE:
<221> NAME/KEY: VARIANT
<222> LOCATION: (19)..(19)
<223> OTHER INFORMATION: /replace="Leu"

<400> SEQUENCE: 34

Met Glu Ile Asn Glu Lys Leu Leu Arg Gln Ile Ile Glu Asp Val Leu
1               5                   10                  15

Lys Glu Met

<210> SEQ ID NO 35
<211> LENGTH: 19
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (3)..(3)
<223> OTHER INFORMATION: /replace="Thr"
<220> FEATURE:
<221> NAME/KEY: VARIANT
<222> LOCATION: (4)..(4)
<223> OTHER INFORMATION: /replace="Thr"
<220> FEATURE:
<221> NAME/KEY: VARIANT
<222> LOCATION: (5)..(5)
<223> OTHER INFORMATION: /replace="Gln"
<220> FEATURE:
<221> NAME/KEY: VARIANT
<222> LOCATION: (6)..(6)
<223> OTHER INFORMATION: /replace="Leu"
<220> FEATURE:
<221> NAME/KEY: VARIANT
<222> LOCATION: (8)..(8)
<223> OTHER INFORMATION: /replace="Asn"
<220> FEATURE:
<221> NAME/KEY: VARIANT
<222> LOCATION: (9)..(9)
<223> OTHER INFORMATION: /replace="Met"
<220> FEATURE:
<221> NAME/KEY: VARIANT
<222> LOCATION: (10)..(10)
<223> OTHER INFORMATION: /replace="Ile"
<220> FEATURE:
<221> NAME/KEY: VARIANT
<222> LOCATION: (11)..(11)
<223> OTHER INFORMATION: /replace="Arg"
<220> FEATURE:
<221> NAME/KEY: VARIANT
<222> LOCATION: (12)..(12)
<223> OTHER INFORMATION: /replace="Lys"
      /replace="Asn"
<220> FEATURE:
<221> NAME/KEY: VARIANT
<222> LOCATION: (15)..(15)
<223> OTHER INFORMATION: /replace="Ala"
      /replace="Glu"
      /replace="Arg"
<220> FEATURE:
<221> NAME/KEY: VARIANT
<222> LOCATION: (16)..(16)
<223> OTHER INFORMATION: /replace="Lys"
<220> FEATURE:
<221> NAME/KEY: VARIANT
```

```
<222> LOCATION: (17)..(17)
<223> OTHER INFORMATION: /replace="Phe"
      /replace="Tyr"
<220> FEATURE:
<221> NAME/KEY: VARIANT
<222> LOCATION: (18)..(18)
<223> OTHER INFORMATION: /replace="Leu"
      /replace="Gly"

<400> SEQUENCE: 35

Met Asn Asp Ile Glu Ile Glu Gln Ala Val Ser Thr Ile Leu Ser Asp
1               5                   10                  15

Asn Thr Lys

<210> SEQ ID NO 36
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (4)..(4)
<223> OTHER INFORMATION: /replace="Thr"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: VARIANT
<222> LOCATION: (14)..(14)
<223> OTHER INFORMATION: /replace="Glu"
<220> FEATURE:
<221> NAME/KEY: VARIANT
<222> LOCATION: (17)..(17)
<223> OTHER INFORMATION: /replace="Ser"
<220> FEATURE:
<221> NAME/KEY: VARIANT
<222> LOCATION: (18)..(18)
<223> OTHER INFORMATION: /replace="Gln"
<220> FEATURE:
<221> NAME/KEY: VARIANT
<222> LOCATION: (19)..(19)
<223> OTHER INFORMATION: /replace="Leu"
<220> FEATURE:
<221> NAME/KEY: VARIANT
<222> LOCATION: (20)..(20)
<223> OTHER INFORMATION: /replace="Asn"

<400> SEQUENCE: 36

Met Gln Ile Asp Glu Glu Leu Ile Arg Ser Val Val Gln Gln Val Leu
1               5                   10                  15

Ala Glu Val Gly
            20

<210> SEQ ID NO 37
<211> LENGTH: 15
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(1)
<223> OTHER INFORMATION: /replace="Gln"
      /replace="Asp"
<220> FEATURE:
<221> NAME/KEY: VARIANT
<222> LOCATION: (2)..(2)
```

```
<223> OTHER INFORMATION: /replace="Glu"
     /replace="Asp"
<220> FEATURE:
<221> NAME/KEY: VARIANT
<222> LOCATION: (3)..(3)
<223> OTHER INFORMATION: /replace="Ile"
     /replace="Leu"
<220> FEATURE:
<221> NAME/KEY: VARIANT
<222> LOCATION: (4)..(4)
<223> OTHER INFORMATION: /replace="Gln"
<220> FEATURE:
<221> NAME/KEY: VARIANT
<222> LOCATION: (5)..(5)
<223> OTHER INFORMATION: /replace="Gln"
     /replace="Asp"
<220> FEATURE:
<221> NAME/KEY: VARIANT
<222> LOCATION: (6)..(6)
<223> OTHER INFORMATION: /replace="Leu"
     /replace="Val"
<220> FEATURE:
<221> NAME/KEY: VARIANT
<222> LOCATION: (7)..(7)
<223> OTHER INFORMATION: /replace="Leu"
     /replace="Val"
<220> FEATURE:
<221> NAME/KEY: VARIANT
<222> LOCATION: (8)..(8)
<223> OTHER INFORMATION: /replace="Arg"
     /replace="Asn"
<220> FEATURE:
<221> NAME/KEY: VARIANT
<222> LOCATION: (9)..(9)
<223> OTHER INFORMATION: /replace="Gln"
     /replace="Lys"
<220> FEATURE:
<221> NAME/KEY: VARIANT
<222> LOCATION: (10)..(10)
<223> OTHER INFORMATION: /replace="Ile"
     /replace="Leu"
<220> FEATURE:
<221> NAME/KEY: VARIANT
<222> LOCATION: (11)..(11)
<223> OTHER INFORMATION: /replace="Ile"
     /replace="Val"
<220> FEATURE:
<221> NAME/KEY: VARIANT
<222> LOCATION: (12)..(12)
<223> OTHER INFORMATION: /replace="Gln"
     /replace="Gly"
<220> FEATURE:
<221> NAME/KEY: VARIANT
<222> LOCATION: (13)..(13)
<223> OTHER INFORMATION: /replace="Arg"
     /replace="Ala"
<220> FEATURE:
<221> NAME/KEY: VARIANT
<222> LOCATION: (14)..(14)
<223> OTHER INFORMATION: /replace="Met"
<220> FEATURE:
<221> NAME/KEY: VARIANT
<222> LOCATION: (15)..(15)
<223> OTHER INFORMATION: /replace="Gly"
     /replace="Ser"

<400> SEQUENCE: 37

Glu Asn Val Glu Arg Ile Ile Lys Glu Val Leu Glu Gln Leu Lys
1               5                   10                  15

<210> SEQ ID NO 38
<211> LENGTH: 18
<212> TYPE: PRT
<213> ORGANISM: Synechococcus elongatus

<400> SEQUENCE: 38
```

```
Val Tyr Gly Lys Glu Gln Phe Leu Arg Met Arg Gln Ser Met Phe Pro
1               5                   10                  15

Asp Arg

<210> SEQ ID NO 39
<211> LENGTH: 13
<212> TYPE: PRT
<213> ORGANISM: Synechococcus elongatus

<400> SEQUENCE: 39

Leu Ala Pro Glu Gln Gln Gln Arg Ile Tyr Arg Gly Asn
1               5                   10

<210> SEQ ID NO 40
<211> LENGTH: 16
<212> TYPE: PRT
<213> ORGANISM: Salmonella typhimurium

<400> SEQUENCE: 40

Met Asp Gln Lys Gln Ile Glu Glu Ile Val Arg Ser Val Met Ala Ser
1               5                   10                  15

<210> SEQ ID NO 41
<211> LENGTH: 17
<212> TYPE: PRT
<213> ORGANISM: Clostridium phytofermentans

<400> SEQUENCE: 41

Met Asn Gln Gln Asp Ile Glu Gln Val Val Lys Ala Val Leu Leu Lys
1               5                   10                  15

Met

<210> SEQ ID NO 42
<211> LENGTH: 16
<212> TYPE: PRT
<213> ORGANISM: Clostridium phytofermentans

<400> SEQUENCE: 42

Asn Thr Glu Leu Val Glu Glu Ile Val Lys Arg Ile Met Lys Gln Leu
1               5                   10                  15

<210> SEQ ID NO 43
<211> LENGTH: 19
<212> TYPE: PRT
<213> ORGANISM: Salmonella typhimurium

<400> SEQUENCE: 43

Met Glu Ile Asn Glu Lys Leu Leu Arg Gln Ile Ile Glu Asp Val Leu
1               5                   10                  15

Arg Asp Met

<210> SEQ ID NO 44
<211> LENGTH: 18
<212> TYPE: PRT
<213> ORGANISM: Salmonella typhimurium

<400> SEQUENCE: 44

Met Glu Ile Asn Glu Lys Leu Leu Arg Gln Ile Ile Glu Asp Val Leu
1               5                   10                  15

Arg Asp

<210> SEQ ID NO 45
```

```
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 45

Met Glu Ile Asn Glu Lys Leu Leu Arg Gln Ile Ile Glu Asp Val Leu
1               5                   10                  15

Ser Glu

<210> SEQ ID NO 46
<211> LENGTH: 19
<212> TYPE: PRT
<213> ORGANISM: Salmonella typhimurium

<400> SEQUENCE: 46

Met Asn Thr Asp Ala Ile Glu Ser Met Val Arg Asp Val Leu Ser Arg
1               5                   10                  15

Met Asn Ser

<210> SEQ ID NO 47
<211> LENGTH: 16
<212> TYPE: PRT
<213> ORGANISM: Salmonella typhimurium

<400> SEQUENCE: 47

Met Asn Thr Ser Glu Leu Glu Thr Leu Ile Arg Thr Ile Leu Ser Glu
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 48

Met Asn Thr Ser Glu Leu Glu Thr Leu Ile Arg Asn Ile Leu Ser Glu
1               5                   10                  15

<210> SEQ ID NO 49
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 49

Met Asn Thr Ser Glu Leu Glu Thr Leu Ile Arg Asn Ile Leu Ser Glu
1               5                   10                  15

Gln Leu

<210> SEQ ID NO 50
<211> LENGTH: 26
<212> TYPE: PRT
<213> ORGANISM: Rhodopseudomonas palustris

<400> SEQUENCE: 50

Ala Gly Thr Asn Tyr Thr Glu Glu Gln Val Phe Ala Ala Val Lys Lys
1               5                   10                  15

Val Leu Asn Ser Ser Gly Ser Thr Asp Val
            20                  25
```

<210> SEQ ID NO 51
<211> LENGTH: 19
<212> TYPE: PRT
<213> ORGANISM: Rhodopseudomonas palustris

<400> SEQUENCE: 51

Met Val Ala Lys Ala Ile Arg Asp His Ala Gly Thr Ala Gln Pro Ser
1               5                   10                  15

Gly Asn Ala

<210> SEQ ID NO 52
<211> LENGTH: 21
<212> TYPE: PRT
<213> ORGANISM: Clostridium phytofermentans

<400> SEQUENCE: 52

Ile Asp Ile Ile Leu Ala Gln Gln Ile Thr Val Gln Ile Val Lys Glu
1               5                   10                  15

Leu Lys Glu Arg Gly
            20

<210> SEQ ID NO 53
<211> LENGTH: 18
<212> TYPE: PRT
<213> ORGANISM: Clostridium phytofermentans

<400> SEQUENCE: 53

Asp Asn Ala Asp Leu Val Ala Ser Ile Thr Arg Lys Val Met Glu Gln
1               5                   10                  15

Leu Gly

<210> SEQ ID NO 54
<211> LENGTH: 20
<212> TYPE: PRT
<213> ORGANISM: Clostridium phytofermentans

<400> SEQUENCE: 54

Val Asn Glu Gln Leu Val Gln Asp Ile Ile Lys Asn Val Val Ala Ser
1               5                   10                  15

Met Gln Leu Thr
            20

<210> SEQ ID NO 55
<211> LENGTH: 21
<212> TYPE: PRT
<213> ORGANISM: Clostridium kluyveri

<400> SEQUENCE: 55

Glu Pro Glu Asp Asn Glu Asp Val Gln Ala Ile Val Lys Ala Ile Met
1               5                   10                  15

Ala Lys Leu Asn Leu
            20

<210> SEQ ID NO 56
<211> LENGTH: 19
<212> TYPE: PRT
<213> ORGANISM: Planctomyces limnophilus

<400> SEQUENCE: 56

Asp Thr Glu Met Leu Val Lys Met Ile Thr Glu Gln Val Met Ala Ala
1               5                   10                  15

Leu Lys Lys

<210> SEQ ID NO 57
<211> LENGTH: 20
<212> TYPE: PRT
<213> ORGANISM: Planctomyces limnophilus

<400> SEQUENCE: 57

Met Gln Ala Thr Glu Gln Ala Ile Arg Gln Val Val Gln Glu Val Leu
1               5                   10                  15

Ala Gln Leu Asn
            20

<210> SEQ ID NO 58
<211> LENGTH: 18
<212> TYPE: PRT
<213> ORGANISM: Opitutus terrae

<400> SEQUENCE: 58

Glu Val Glu Ala Leu Val Gln Arg Leu Thr Glu Glu Ile Leu Arg Gln
1               5                   10                  15

Leu Gln

<210> SEQ ID NO 59
<211> LENGTH: 17
<212> TYPE: PRT
<213> ORGANISM: Opitutus terrae

<400> SEQUENCE: 59

Ile Asp Glu Thr Leu Val Arg Ser Val Val Glu Val Val Arg Ala
1               5                   10                  15

Phe

<210> SEQ ID NO 60
<211> LENGTH: 15
<212> TYPE: PRT
<213> ORGANISM: Clostridium phytofermentans

<400> SEQUENCE: 60

Glu Asp Ala Arg Asp Leu Leu Lys Gln Ile Leu Gln Ala Leu Ser
1               5                   10                  15

<210> SEQ ID NO 61
<211> LENGTH: 17
<212> TYPE: PRT
<213> ORGANISM: Clostridium phytofermentans

<400> SEQUENCE: 61

Met Asp Ile Arg Glu Phe Ser Asn Lys Phe Val Glu Ala Thr Lys Asn
1               5                   10                  15

Met

<210> SEQ ID NO 62
<211> LENGTH: 22
<212> TYPE: PRT
<213> ORGANISM: Mycobacterium smegmatis

<400> SEQUENCE: 62

Leu Asp Ala Leu Arg Ala Glu Leu Arg Ala Leu Val Val Glu Glu Leu
1               5                   10                  15

Ala Gln Leu Ile Lys Arg
            20

<210> SEQ ID NO 63
<211> LENGTH: 19
<212> TYPE: PRT
<213> ORGANISM: Haliangium ochraceum

<400> SEQUENCE: 63

Met Ala Leu Arg Glu Asp Arg Ile Ala Glu Ile Val Glu Arg Val Leu
1               5                   10                  15

Ala Arg Leu

<210> SEQ ID NO 64
<211> LENGTH: 39
<212> TYPE: PRT
<213> ORGANISM: Artificial sequence
<220> FEATURE:
<223> OTHER INFORMATION: Synthetic Sequence

<400> SEQUENCE: 64

Met Glu Ile Asn Glu Lys Leu Leu Arg Gln Ile Ile Glu Asp Val Leu
1               5                   10                  15

Ser Glu Pro Met Gly Ser Ser His His His His His His Ser Ser Gly
            20                  25                  30

Leu Val Pro Arg Gly Ser His
        35

<210> SEQ ID NO 65
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 65

Met Asn Thr Ser Glu Leu Glu Thr Leu Ile Arg Asn Ile Leu Ser Glu
1               5                   10                  15

Gln Leu Ala Met Gly Ser Ser His His His His His His Ser Ser Gly
            20                  25                  30

Leu Val Pro Arg Gly Ser His
        35

<210> SEQ ID NO 66
<211> LENGTH: 29
<212> TYPE: DNA
<213> ORGANISM: Artificial Sequence
<220> FEATURE:
<223> OTHER INFORMATION: Primer GldA_NdeI_FW

<400> SEQUENCE: 66
catcatatgg accgcattat tcaatcacc                                    29

<210> SEQ ID NO 67
<211> LENGTH: 28
<212> TYPE: DNA
<213> ORGANISM: Artificial Sequence
<220> FEATURE:
<223> OTHER INFORMATION: Primer GldA_SpeI_RV

<400> SEQUENCE: 67
catactagtt tattcccact cttgcagg                                     28

<210> SEQ ID NO 68
<211> LENGTH: 36

<212> TYPE: DNA
<213> ORGANISM: Artificial Sequence
<220> FEATURE:
<223> OTHER INFORMATION: Primer dhaK_NdeI_FW

<400> SEQUENCE: 68
cgccatatgt ctcaattctt ttttaaccaa cgcacc                              36

<210> SEQ ID NO 69
<211> LENGTH: 30
<212> TYPE: DNA
<213> ORGANISM: Artificial Sequence
<220> FEATURE:
<223> OTHER INFORMATION: Primer dhaK_SpeI_RV

<400> SEQUENCE: 69
catactagtt tagcccagct cactctccgc                                    30

<210> SEQ ID NO 70
<211> LENGTH: 32
<212> TYPE: DNA
<213> ORGANISM: Artificial Sequence
<220> FEATURE:
<223> OTHER INFORMATION: Primer mgsA_NdeI_FW

<400> SEQUENCE: 70
catcatatgg aactgacgac tcgcacttta cc                                 32

<210> SEQ ID NO 71
<211> LENGTH: 30
<212> TYPE: DNA
<213> ORGANISM: Artificial Sequence
<220> FEATURE:
<223> OTHER INFORMATION: Primer mgsA_SpeI_RV

<400> SEQUENCE: 71
catactagtt tacttcagac ggtccgcgag                                    30

<210> SEQ ID NO 72
<211> LENGTH: 27
<212> TYPE: DNA
<213> ORGANISM: Artificial Sequence
<220> FEATURE:
<223> OTHER INFORMATION: Primer fucO_NdeI_FW

<400> SEQUENCE: 72
ccgcatatgg ctaacagaat gattctg                                       27

<210> SEQ ID NO 73
<211> LENGTH: 25
<212> TYPE: DNA
<213> ORGANISM: Artificial Sequence
<220> FEATURE:
<223> OTHER INFORMATION: Primer fucO_SpeI_RV

<400> SEQUENCE: 73
cctactagtt taccaggcgg tatgg                                         25

<210> SEQ ID NO 74
<211> LENGTH: 30
<212> TYPE: DNA
<213> ORGANISM: Artificial Sequence
<220> FEATURE:
<223> OTHER INFORMATION: Primer GFP_NdeI_FW

<400> SEQUENCE: 74

```
gtacatatga gcaaaggaga agaacttttc                                    30
```

```
<210> SEQ ID NO 75
<211> LENGTH: 66
<212> TYPE: DNA
<213> ORGANISM: Artificial Sequence
<220> FEATURE:
<223> OTHER INFORMATION: Primer GFP-SsrA_SpeI_RV

<400> SEQUENCE: 75
```

```
gacactagtt taagctgcta aagcgtagtt ttcgtcgttt gctgctttgt acagctcatc   60
catgcc                                                              66
```

```
<210> SEQ ID NO 76
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: hydrophobic amino acid
<220> FEATURE:
<221> NAME/KEY: MISC_FEATURE
<222> LOCATION: (2)..(2)
<223> OTHER INFORMATION: polar or charged amino acid
<220> FEATURE:
<221> NAME/KEY: MISC_FEATURE
<222> LOCATION: (3)..(3)
<223> OTHER INFORMATION: polar or charged amino acid
<220> FEATURE:
<221> NAME/KEY: MISC_FEATURE
<222> LOCATION: (4)..(4)
<223> OTHER INFORMATION: hydrophobic amino acid
<220> FEATURE:
<221> NAME/KEY: MISC_FEATURE
<222> LOCATION: (5)..(5)
<223> OTHER INFORMATION: hydrophobic amino acid
<220> FEATURE:
<221> NAME/KEY: MISC_FEATURE
<222> LOCATION: (6)..(6)
<223> OTHER INFORMATION: polar or charged amino acid
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: hydrophobic amino acid
<220> FEATURE:
<221> NAME/KEY: MISC_FEATURE
<222> LOCATION: (9)..(9)
<223> OTHER INFORMATION: hydrophobic amino acid

<400> SEQUENCE: 76

Xaa Xaa Xaa Xaa Xaa Xaa Xaa Xaa Xaa
1               5
```

```
<210> SEQ ID NO 77
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(1)
<223> OTHER INFORMATION: /replace="Leu"
      /replace="Val"
      /replace="Met"
      /replace="Phe"
```

```
      /replace="Tyr"
      /replace="Ala"
      /replace="Trp"
<220> FEATURE:
<221> NAME/KEY: VARIANT
<222> LOCATION: (2)..(2)
<223> OTHER INFORMATION: /replace="Asn"
      /replace="Thr"
      /replace="Ser"
      /replace="Cys"
      /replace="Asp"
      /replace="Glu"
      /replace="Arg"
      /replace="Lys"
      /replace="His"
<220> FEATURE:
<221> NAME/KEY: VARIANT
<222> LOCATION: (3)..(3)
<223> OTHER INFORMATION: /replace="Asn"
      /replace="Thr"
      /replace="Ser"
      /replace="Cys"
      /replace="Asp"
      /replace="Glu"
      /replace="Arg"
      /replace="Lys"
      /replace="His"
<220> FEATURE:
<221> NAME/KEY: VARIANT
<222> LOCATION: (4)..(4)
<223> OTHER INFORMATION: /replace="Leu"
      /replace="Val"
      /replace="Met"
      /replace="Phe"
      /replace="Tyr"
      /replace="Ala"
      /replace="Trp"
<220> FEATURE:
<221> NAME/KEY: VARIANT
<222> LOCATION: (5)..(5)
<223> OTHER INFORMATION: /replace="Leu"
      /replace="Val"
      /replace="Met"
      /replace="Phe"
      /replace="Tyr"
      /replace="Ala"
      /replace="Trp"
<220> FEATURE:
<221> NAME/KEY: VARIANT
<222> LOCATION: (6)..(6)
<223> OTHER INFORMATION: /replace="Asn"
      /replace="Thr"
      /replace="Ser"
      /replace="Cys"
      /replace="Asp"
      /replace="Glu"
      /replace="Arg"
      /replace="Lys"
      /replace="His"
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: VARIANT
<222> LOCATION: (8)..(8)
<223> OTHER INFORMATION: /replace="Leu"
      /replace="Val"
      /replace="Met"
      /replace="Phe"
      /replace="Tyr"
      /replace="Ala"
      /replace="Trp"
<220> FEATURE:
<221> NAME/KEY: VARIANT
<222> LOCATION: (9)..(9)
<223> OTHER INFORMATION: /replace="Leu"
      /replace="Val"
      /replace="Met"
```

/replace="Phe"
       /replace="Tyr"
       /replace="Ala"
       /replace="Trp"

<400> SEQUENCE: 77

Ile Gln Gln Ile Ile Gln Xaa Ile Ile
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(1)
<223> OTHER INFORMATION: /replace="Leu"
       /replace="Val"
       /replace="Met"
       /replace="Ala"
<220> FEATURE:
<221> NAME/KEY: VARIANT
<222> LOCATION: (2)..(2)
<223> OTHER INFORMATION: /replace="Thr"
       /replace="Glu"
       /replace="Arg"
       /replace="Ser"
       /replace="Asp"
       /replace="Lys"
<220> FEATURE:
<221> NAME/KEY: VARIANT
<222> LOCATION: (3)..(3)
<223> OTHER INFORMATION: /replace="Thr"
       /replace="Glu"
       /replace="Arg"
       /replace="Ser"
       /replace="Asp"
       /replace="Lys"
<220> FEATURE:
<221> NAME/KEY: VARIANT
<222> LOCATION: (4)..(4)
<223> OTHER INFORMATION: /replace="Leu"
       /replace="Val"
       /replace="Met"
       /replace="Ala"
<220> FEATURE:
<221> NAME/KEY: VARIANT
<222> LOCATION: (5)..(5)
<223> OTHER INFORMATION: /replace="Leu"
       /replace="Val"
       /replace="Met"
       /replace="Ala"
<220> FEATURE:
<221> NAME/KEY: VARIANT
<222> LOCATION: (6)..(6)
<223> OTHER INFORMATION: /replace="Thr"
       /replace="Glu"
       /replace="Arg"
       /replace="Ser"
       /replace="Asp"
       /replace="Lys"
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: VARIANT
<222> LOCATION: (8)..(8)
<223> OTHER INFORMATION: /replace="Leu"
       /replace="Val"
       /replace="Met"
       /replace="Ala"
<220> FEATURE:
<221> NAME/KEY: VARIANT
<222> LOCATION: (9)..(9)

```
<223> OTHER INFORMATION: /replace="Leu"
     /replace="Val"
     /replace="Met"
     /replace="Ala"

<400> SEQUENCE: 78

Ile Gln Gln Ile Ile Gln Xaa Ile Ile
1               5

<210> SEQ ID NO 79
<211> LENGTH: 9
<212> TYPE: PRT
<213> ORGANISM: Artificial Sequence
<220> FEATURE:
<223> OTHER INFORMATION: Artificial Sequence
<220> FEATURE:
<221> NAME/KEY: VARIANT
<222> LOCATION: (1)..(1)
<223> OTHER INFORMATION: /replace="Leu"
     /replace="Val"
     /replace="Ala"
<220> FEATURE:
<221> NAME/KEY: VARIANT
<222> LOCATION: (2)..(2)
<223> OTHER INFORMATION: /replace="Glu"
     /replace="Arg"
<220> FEATURE:
<221> NAME/KEY: VARIANT
<222> LOCATION: (3)..(3)
<223> OTHER INFORMATION: /replace="Thr"
     /replace="Glu"
     /replace="Ser"
     /replace="Asp"
     /replace="Lys"
<220> FEATURE:
<221> NAME/KEY: VARIANT
<222> LOCATION: (4)..(4)
<223> OTHER INFORMATION: /replace="Leu"
     /replace="Val"
     /replace="Met"
<220> FEATURE:
<221> NAME/KEY: VARIANT
<222> LOCATION: (5)..(5)
<223> OTHER INFORMATION: /replace="Leu"
     /replace="Val"
<220> FEATURE:
<221> NAME/KEY: VARIANT
<222> LOCATION: (6)..(6)
<223> OTHER INFORMATION: /replace="Arg"
     /replace="Lys"
     /replace="Glu"
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: VARIANT
<222> LOCATION: (8)..(8)
<223> OTHER INFORMATION: /replace="Leu"
     /replace="Val"
     /replace="Ala"
<220> FEATURE:
<221> NAME/KEY: VARIANT
<222> LOCATION: (9)..(9)
<223> OTHER INFORMATION: /replace="Leu"
     /replace="Val"
     /replace="Met"

<400> SEQUENCE: 79

Ile Gln Gln Ile Ile Gln Xaa Ile Ile
1               5
```